US005747239A

United States Patent [19]
Wang et al.

[11] Patent Number: 5,747,239
[45] Date of Patent: May 5, 1998

[54] SYNTHETIC PEPTIDES SPECIFIC FOR THE DETECTION OF ANTIBODIES TO HCV, DIAGNOSIS OF HCV INFECTION AND PREVENTIONS THEREOF AS VACCINES

[75] Inventors: Chang Yi Wang, Great Neck; Barbara Hosein, New York, both of N.Y.

[73] Assignee: United Biomedical, Inc., Hauppauge, N.Y.

[21] Appl. No.: 262,037

[22] Filed: Jun. 17, 1994

Related U.S. Application Data

[63] Continuation of Ser. No. 719,819, Jun. 24, 1991, abandoned, which is a continuation-in-part of Ser. No. 667,275, Mar. 11, 1991, abandoned, which is a continuation-in-part of Ser. No. 651,735, Feb. 7, 1991, abandoned, which is a continuation-in-part of Ser. No. 558,799, Jul. 26, 1990, Pat. No. 5,106,726, which is a continuation-in-part of Ser. No. 510,153, Apr. 16, 1990, abandoned, which is a continuation-in-part of Ser. No. 481,348, Feb. 16, 1990, abandoned.

[51] Int. Cl.$^6$ .................. C12Q 1/70; C07K 14/18
[52] U.S. Cl. .................................... 435/5; 530/324
[58] Field of Search ........................ 435/5; 530/324

[56] References Cited

U.S. PATENT DOCUMENTS

| 4,356,164 | 10/1982 | Tabor et al. | 435/5 |
|---|---|---|---|
| 4,395,395 | 7/1983 | Tabor et al. | 424/89 |
| 4,464,474 | 8/1984 | Coursaget et al. | 436/513 |
| 4,542,016 | 9/1985 | Trepo | 424/86 |
| 4,554,101 | 11/1985 | Hopp | 530/324 |
| 4,673,634 | 6/1987 | Seto et al. | 435/5 |
| 4,702,909 | 10/1987 | Villarejos et al. | 424/89 |
| 4,735,893 | 4/1988 | Wang et al. | 435/5 |
| 4,777,245 | 10/1988 | Foung et al. | 530/388.3 |
| 4,833,071 | 5/1989 | Wang et al. | 435/5 |
| 4,871,659 | 10/1989 | Pillot | 435/5 |
| 4,879,212 | 11/1989 | Wang et al. | 435/5 |
| 5,106,726 | 4/1992 | Wang | 735/5 |
| 5,350,671 | 9/1994 | Houghton et al. | 435/5 |

FOREIGN PATENT DOCUMENTS

| 263761 | 4/1988 | European Pat. Off. |
| 293274 | 11/1988 | European Pat. Off. |
| 318216 | of 1989 | European Pat. Off. |
| 328403 | of 1989 | European Pat. Off. |
| 335135 | 10/1989 | European Pat. Off. |
| 363025 | 4/1990 | European Pat. Off. |
| 388232 | 9/1990 | European Pat. Off. |
| 2609807 | 7/1988 | France |
| WO9000597 | 1/1990 | WIPO |
| WO90022206 | 3/1990 | WIPO |

OTHER PUBLICATIONS

Atessi et al, in "Antigen Specific T cell receptors and factors", CRC Press, Boca Rotan FlA. 1987, pp. 7–63.
Printout Pom Dialog Search, File 155, Performed Aug. 24, 1993.
MacCullum FO, et al.:*Lancet*, 1:6222 (1944).
Havens WP: *Proc Soc Exp Biol Med*, 59:148 (1945).
Krugman S, et al.: *JAMA*, 200:365 (1967).
Prince AM: *Lancet*, 2:241 (1974).
Alter HJ, et al: *Lancet*, 2:838 (1975).
Galbraith RM, et al: *Lancet*, 2:886 (1975).
Mosley JW, et al: *N. Engl J Med*, 296:75 (1977).
Dienstag JL: *Rush–Presbyterian–St. Luke's Med Bull*, 15:104 (1976).
Aach RD, et al: *N. Engl J Med* 304:989 (1981).
Hollinger FB, et al: *Viral Hepatitis: 1981 International Symposium*, Szmuness W, Alter HJ, Maynard JE, (eds), Philadelphia: Franklin Institute Press, p. 361 (1982).
Alter HJ, et al.: *JAMA*, 246:630 (1981).
Stevens CE, et al: *Ann Int Med*, 101:733 (1984).
Koziol DE, et al: *Ann Int Med*, 104:488 (1986).
Sugg U, et al.: *Transfusion*, 28:386 (1988).
Choo Q–L, et al: *Science*, 244:359 (1989).
Kuo G, et al: *Science*, 244:362 (1989).
Wang CY: *Synthetic Peptides in Biotechnology*, A. Mizrahi (ed), *Adv in Biotechnological Processes*, 10:131 (1988).
Wang JG, et al.: *Proc Natl Acad Sci USA*, 83:6159 (1986).
UBI–Olympus HIV-1 EIA Product Insert, Jun. 1, 1989. License No. 1079, approved by US FDA.
Okamoto, H., et al.: *Jpn. J. Exp. Med.* 1990 (in press).
Schlesinger, S., et al.: The Togaviridae and Flaviviridae. In: The Viruses. Plenum Press, New York, 1986, pp. 278–326.
Kubo, Y., et al: *Nucleu Acid Res*. 17:10367–10372 (1989).
Slide Presentation by Abbot Laboratories to American Association of Blood Banks (Oct. 1989).
Weiner et al., *Lancet*, 335: 1–3 (Jan. 1990).
McClelland et al., *Lancet*, pp. 36–37 (Jul. 1987).
Feinman et al., *CMA Journal*, 123: 181–184 (Aug. 1980).
T.H. Maugh II, *Science*, 210: 999–1000 (Nov. 1980).
Hantz et al., *J. Med. Virol.*, 5: 73–86 (1980).
Tabor et al., *N. Engl. J. of Med.*, 303: 139–143 (1980).
Letters to Editor, *Lancet*, pp. 796–799 (Sep. 30, 1989).
Lynn et al., *MMWR*, 38: 529–531 (Aug. 1989).
Polesky et al., *Arch. Pathol. Lab. Med.*, 113: 232–235 (Mar. 1989).
G. Kolata, *Science*, 23: 149–150 (Jul. 1986).
Troisi et al., *Transfusion*, 27: 438–440 (1987).
Schumacher et al., *The Ligand Quart.*, 5: 12–27 (Nov. 1982).
Arima T. et al., *Gastroenterologia Jap.*, 24:540–544 (1989).
Arima T. et al., *Gastroenterologia Jap.*, 24:545–548 (1989).
Arima T. et al., *Gastroenterologia Jap.*, 24:685–691 (1989).
Arima T. et al., *Gastroenterologia Jap.*, 25:2218–232 (1990).
Chou, P. Y. and Fasman, G.D., *Biochemisty*, 13:222–245 (1974).

*Primary Examiner*—Michael P. Woodward
*Attorney, Agent, or Firm*—Morgan & Finnegan, L.L.P.

[57] ABSTRACT

The present invention relates to peptides which are immunoreactive to antibodies to HCV or NANBHV and a method of detecting the presence of HCV or NANBHV antibodies in body fluids by using the peptides as the antigen. The peptides are selected from both the envelope and non-structural protein regions of the HCV or NANBHV. The detection method includes enzyme linked immunosorbent assay or other immunoassay procedures. The peptides and conjugates or polymers thereof are also useful as immunogens in generating high titer antibodies to HCV or in vaccines.

3 Claims, 1 Drawing Sheet

SEQUENCE LISTING ( 1 ) GENERAL INFORMATION:

( i i i ) NUMBER OF SEQUENCES: 136

( 2 ) INFORMATION FOR SEQ ID NO:1:

( i ) SEQUENCE CHARACTERISTICS:
        ( A ) LENGTH: 42 amino acids
        ( B ) TYPE: Amino acid
        ( C ) STRANDEDNESS:
        ( D ) TOPOLOGY: Unknown ( i i ) MOLECULE TYPE: Peptide ( i i i ) HYPOTHETICAL: No ( i v ) ANTI-SENSE: No ( x i ) SEQUENCE DESCRIPTION:SEQ ID NO: 1:

```
Gln  Gly  Trp  Gly  Pro  Ile  Ser  Tyr  Ala  Asn  Gly  Ser  Gly  Pro  Asp
 1                  5                         10                        15

Gln  Arg  Pro  Tyr  Cys  Trp  His  Tyr  Pro  Pro  Lys  Pro  Cys  Gly  Ile
```

```
                                  20                        25                        30
Val  Pro  Ala  Lys  Ser  Val  Cys  Gly  Pro  Val  Tyr  Cys
                        35                        40
```

( 2 ) INFORMATION FOR SEQ ID NO: 2:

( i ) SEQUENCE CHARACTERISTICS:
        ( A ) LENGTH: 26 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 2:

```
Pro  Pro  Leu  Gly  Asn  Trp  Phe  Gly  Cys  Thr  Trp  Met  Asn  Ser  Thr
1                        5                        10                       15

Gly  Phe  Thr  Lys  Val  Cys  Gly  Ala  Pro  Pro  Cys
                        20                        25
```

( 2 ) INFORMATION FOR SEQ ID NO: 3:

( i ) SEQUENCE CHARACTERISTICS:
        ( A ) LENGTH: 37 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 3:

```
Gly  Cys  Ser  Gly  Gly  Ala  Tyr  Asp  Ile  Ile  Ile  Cys  Asp  Glu  Leu
1                        5                        10                       15

His  Ser  Thr  Asp  Ala  Thr  Ser  Ile  Leu  Gly  Ile  Gly  Thr  Val  Leu
                        20                        25                       30

Asp  Gln  Ala  Glu  Thr  Ala  Gly
                        35
```

( 2 ) INFORMATION FOR SEQ ID NO: 4:

( i ) SEQUENCE CHARACTERISTICS:
        ( A ) LENGTH: 46 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 4:

```
Asp  Pro  Ser  His  Ile  Thr  Ala  Glu  Ala  Ala  Gly  Arg  Arg  Leu  Ala
1                        5                        10                       15

Arg  Gly  Ser  Pro  Pro  Ser  Val  Ala  Ser  Ser  Ser  Ala  Ser  Gln  Leu
  20                          25                        30

Ser  Ala  Pro  Ser  Leu  Lys  Ala  Thr  Cys  Thr  Ala  Asn  His  Asp  Ser
  35                          40                        45

Pro
```

( 2 ) INFORMATION FOR SEQ ID NO: 5:

( i ) SEQUENCE CHARACTERISTICS:
        ( A ) LENGTH: 44 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 5:

```
Asp  Ala  Glu  Leu  Ile  Glu  Ala  Asn  Leu  Leu  Trp  Arg  Gln  Glu  Met
1                        5                        10                       15

Gly  Gly  Asn  Ile  Thr  Arg  Val  Glu  Ser  Glu  Asn  Lys  Val  Val  Ile
                        20                        25                       30
```

-continued

```
Leu  Asp  Ser  Phe  Asp  Pro  Leu  Val  Ala  Glu  Glu  Asp  Glu  Arg
               35                      40
```

( 2 ) INFORMATION FOR SEQ ID NO: 6:

( i ) SEQUENCE CHARACTERISTICS:
      ( A ) LENGTH: 37 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 6:

```
Asp  Pro  Gln  Ala  Arg  Val  Ala  Ile  Lys  Ser  Leu  Thr  Glu  Arg  Leu
 1              5                        10                       15

Thr  Val  Gly  Gly  Pro  Leu  Thr  Asn  Ser  Arg  Gly  Glu  Asn  Cys  Gly
              20                        25                       30

Tyr  Arg  Arg  Cys  Arg  Ala  Ser
              35
```

( 2 ) INFORMATION FOR SEQ ID NO: 7:

( i ) SEQUENCE CHARACTERISTICS:
      ( A ) LENGTH: 55 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 7:

```
Cys  Leu  Thr  Val  Pro  Ala  Ser  Ala  Tyr  Gln  Val  Arg  Asn  Ser  Thr
 1              5                        10                       15

Gly  Leu  Tyr  His  Val  Thr  Asn  Asp  Cys  Pro  Asn  Ser  Ser  Ile  Val
              20                        25                       30

Tyr  Glu  Ala  His  Asp  Ala  Ile  Leu  His  Thr  Pro  Gly  Cys  Val  Pro
              35                        40                       45

Cys  Val  Arg  Glu  Gly  Asn  Val  Ser  Arg  Cys
              50                        55
```

( 2 ) INFORMATION FOR SEQ ID NO: 8:

( i ) SEQUENCE CHARACTERISTICS:
      ( A ) LENGTH: 40 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 8:

```
Phe  Thr  Phe  Ser  Pro  Arg  Arg  His  Trp  Thr  Thr  Gln  Gly  Cys  Asn
 1              5                        10                       15

Cys  Ser  Ile  Tyr  Pro  Gly  His  Ile  Thr  Gly  His  Arg  Met  Ala  Trp
              20                        25                       30

Asp  Met  Met  Met  Asn  Trp  Ser  Pro  Thr  Ala
              35                        40
```

( 2 ) INFORMATION FOR SEQ ID NO: 9:

( i ) SEQUENCE CHARACTERISTICS:
      ( A ) LENGTH: 35 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 9:

```
Val  Asp  Ala  Glu  Thr  Ile  Val  Ser  Gly  Gly  Gln  Ala  Ala  Arg  Ala
 1              5                        10                       15
```

```
Met  Ser  Gly  Leu  Val  Ser  Leu  Phe  Thr  Pro  Gly  Ala  Lys  Gln  Asn
                    20                     25                     30

Ile  Gln  Leu  Ile  Asn
                    35
```

( 2 ) INFORMATION FOR SEQ ID NO: 10:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 10:

```
Trp  His  Ile  Asn  Ser  Thr  Ala  Leu  Asn  Cys  Asn  Glu  Ser  Leu  Asn
 1                   5                    10                         15

Thr  Gly  Trp  Leu  Ala  Gly  Leu  Ile  Tyr  Glu  His  Lys  Phe  Asn  Ser
                    20                    25                         30

Ser  Gly  Cys  Pro  Glu  Arg  Leu  Ala  Ser  Cys
                    35                    40
```

( 2 ) INFORMATION FOR SEQ ID NO: 11:

( i ) SEQUENCE CHARACTERISTICS:
        ( A ) LENGTH: 60 amino acids
        ( B ) TYPE: Amino acids
        ( C ) STRANDEDNESS:
        ( D ) TOPOLOGY: Unknown ( x i ) SEQUENCE DESCRIPTION:SEQ ID NO: 11:

```
Glu  Ile  Leu  Arg  Lys  Ser  Arg  Arg  Phe  Ala  Gln  Ala  Leu  Pro  Val
 1                   5                    10                         15

Trp  Ala  Arg  Pro  Asp  Tyr  Asn  Pro  Pro  Leu  Val  Glu  Thr  Trp  Lys
                    20                    25                         30

Lys  Pro  Asp  Tyr  Glu  Pro  Pro  Val  Val  His  Gly  Cys  Pro  Leu  Pro
                    35                    40                         45

Pro  Pro  Lys  Ser  Pro  Pro  Val  Pro  Pro  Pro  Arg  Lys  Lys  Arg  Thr
                    50                    55                         60
```

( 2 ) INFORMATION FOR SEQ ID NO: 12:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 12:

```
Lys  Ala  Thr  Cys  Thr  Ala  Asn  His  Asp  Ser  Pro  Asp  Ala  Glu  Leu
 1                   5                    10                         15

Ile  Glu  Ala  Asn  Leu  Leu  Trp  Arg  Gln  Glu  Met  Gly  Gly  Asn  Ile
                    20                    25                         30

Thr  Arg  Val  Glu  Ser  Glu  Asn  Lys  Val  Val  Ile  Leu  Asp  Ser  Phe
                    35                    40                         45

Asp  Pro  Leu  Val  Ala  Glu  Glu  Asp  Glu  Arg
                    50                    55
```

( 2 ) INFORMATION FOR SEQ ID NO: 13:

( i ) SEQUENCE CHARACTERISTICS:
        ( A ) LENGTH: 47 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 13:

Arg Gln Glu Met Gly Gly Asn Ile Thr Arg Val Glu Ser Glu Asn
1               5                   10                  15

Lys Val Val Ile Leu Asp Ser Phe Asp Pro Leu Val Ala Glu Glu
            20                  25                  30

Asp Glu Arg Glu Ile Ser Val Pro Ala Glu Ile Leu Arg Lys Ser
            35                  40                  45

Arg Arg ( 2 ) INFORMATION FOR SEQ ID NO: 14:

( i ) SEQUENCE CHARACTERISTICS:
        ( A ) LENGTH: 31 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 14:

Cys Lys Pro Leu Leu Arg Glu Glu Val Ser Phe Arg Val Gly Leu
1               5                   10                  15

His Glu Tyr Pro Val Gly Ser Gln Leu Pro Cys Glu Pro Glu Pro
            20                  25                  30

Asp ( 2 ) INFORMATION FOR SEQ ID NO: 15:

( i ) SEQUENCE CHARACTERISTICS:
        ( A ) LENGTH: 32 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 15:

Glu Glu Tyr Val Glu Ile Arg Gln Val Gly Asp Phe His Tyr Val
1               5                   10                  15

Thr Gly Met Thr Thr Asp Asn Leu Lys Cys Pro Cys Gln Val Pro
            20                  25                  30

Ser Pro ( 2 ) INFORMATION FOR SEQ ID NO: 16:

( i ) SEQUENCE CHARACTERISTICS:
        ( A ) LENGTH: 30 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 16:

Gly Ser Trp Leu Arg Asp Ile Trp Asp Trp Ile Cys Glu Val Leu
1               5                   10                  15

Ser Asp Phe Lys Thr Trp Leu Lys Ala Lys Leu Met Pro Gln Leu
            20                  25                  30

( 2 ) INFORMATION FOR SEQ ID NO: 17:

( i ) SEQUENCE CHARACTERISTICS:
        ( A ) LENGTH: 45 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 17:

```
Gly Pro Ala Asp Gly Met Val Ser Lys Gly Trp Arg Leu Leu Ala
 1               5                  10                  15

Pro Ile Thr Ala Tyr Ala Gln Gln Thr Arg Gly Leu Leu Gly Cys
                 20                  25                  30

Ile Ile Thr Ser Leu Thr Gly Arg Asp Lys Asn Gln Val Glu Gly
                 35                  40                  45
```

( 2 ) INFORMATION FOR SEQ ID NO: 18:

( i ) SEQUENCE CHARACTERISTICS:
        ( A ) LENGTH: 39 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 18:

```
Glu Ile Pro Phe Tyr Gly Lys Ala Ile Pro Leu Glu Val Ile Lys
 1               5                  10                  15

Gly Gly Arg His Leu Ile Phe Cys His Ser Lys Lys Lys Cys Asp
                 20                  25                  30

Glu Leu Ala Ala Lys Leu Val Ala Leu
                 35
```

( 2 ) INFORMATION FOR SEQ ID NO: 19:

( i ) SEQUENCE CHARACTERISTICS:
        ( A ) LENGTH: 44 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 19:

```
Cys Val Arg Glu Gly Asn Val Ser Arg Cys Trp Val Ala Met Thr
 1               5                  10                  15

Pro Thr Val Ala Thr Arg Asp Gly Lys Leu Pro Ala Thr Gln Leu
                 20                  25                  30

Arg Arg His Ile Asp Leu Leu Val Gly Ser Ala Thr Leu Cys
                 35                  40
```

( 2 ) INFORMATION FOR SEQ ID NO: 20:

( i ) SEQUENCE CHARACTERISTICS:
        ( A ) LENGTH: 61 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 20:

```
Ser Thr Ile Pro Lys Pro Gln Arg Lys Thr Lys Arg His Thr Asn
 1               5                  10                  15

Arg Arg Pro Gln Asp Val Lys Phe Pro Gly Gly Gly Gln Ile Val
                 20                  25                  30

Gly Gly Val Tyr Leu Leu Pro Arg Arg Gly Pro Arg Leu Gly Val
                 35                  40                  45

Arg Ala Thr Arg Lys Thr Ser Glu Arg Ser Gln Pro Arg Gly Arg
                 50                  55                  60

Arg
```

( 2 ) INFORMATION FOR SEQ ID NO: 21:

( i ) SEQUENCE CHARACTERISTICS:
        ( A ) LENGTH: 47 amino acids
        ( B ) TYPE: Amino acid (C) STRANDEDNESS:
(D) TOPOLOGY: Unknown (xi) SEQUENCE DESCRIPTION:SEQ ID NO: 21:

| Ser | Gly | Lys | Pro | Ala | Ile | Ile | Pro | Asp | Arg | Glu | Val | Leu | Tyr | Arg |
|---|---|---|---|---|---|---|---|---|---|---|---|---|---|---|
| 1 | | | | 5 | | | | | 10 | | | | | 15 |

| Glu | Phe | Asp | Glu | Met | Glu | Glu | Cys | Ser | Gln | His | Leu | Pro | Tyr | Ile |
|---|---|---|---|---|---|---|---|---|---|---|---|---|---|---|
| | | | | 20 | | | | | 25 | | | | | 30 |

| Glu | Gln | Gly | Met | Met | Leu | Ala | Glu | Gln | Phe | Lys | Gln | Lys | Ala | Leu |
|---|---|---|---|---|---|---|---|---|---|---|---|---|---|---|
| | | | | 35 | | | | | 40 | | | | | 45 |

Gly Leu (2) INFORMATION FOR SEQ ID NO: 22:

(i) SEQUENCE CHARACTERISTICS:
(A) LENGTH: 40 amino acids
(B) TYPE: Amino acid
(C) STRANDEDNESS:
(D) TOPOLOGY: Unknown (xi) SEQUENCE DESCRIPTION:SEQ ID NO: 22:

| Lys | Gln | Lys | Ala | Leu | Gly | Leu | Leu | Gln | Thr | Ala | Ser | Arg | Gln | Ala |
|---|---|---|---|---|---|---|---|---|---|---|---|---|---|---|
| 1 | | | | 5 | | | | | 10 | | | | | 15 |

| Glu | Val | Ile | Ala | Pro | Ala | Val | Gln | Thr | Asn | Trp | Gln | Lys | Leu | Glu |
|---|---|---|---|---|---|---|---|---|---|---|---|---|---|---|
| | | | | 20 | | | | | 25 | | | | | 30 |

| Thr | Phe | Trp | Ala | Lys | His | Met | Trp | Asn | Phe |
|---|---|---|---|---|---|---|---|---|---|
| | | | | 35 | | | | | 40 |

(2) INFORMATION FOR SEQ ID NO: 23:

(i) SEQUENCE CHARACTERISTICS:
(A) LENGTH: 36 amino acids
(B) TYPE: Amino acid
(C) STRANDEDNESS:
(D) TOPOLOGY: Unknown (xi) SEQUENCE DESCRIPTION:SEQ ID NO: 23:

| Arg | Arg | Gly | Pro | Arg | Leu | Gly | Val | Arg | Ala | Thr | Arg | Lys | Thr | Ser |
|---|---|---|---|---|---|---|---|---|---|---|---|---|---|---|
| 1 | | | | 5 | | | | | 10 | | | | | 15 |

| Glu | Arg | Ser | Gln | Pro | Arg | Gly | Arg | Arg | Gln | Pro | Ile | Pro | Lys | Val |
|---|---|---|---|---|---|---|---|---|---|---|---|---|---|---|
| | | | | 20 | | | | | 25 | | | | | 30 |

| Arg | Arg | Pro | Glu | Gly | Arg |
|---|---|---|---|---|---|
| | | | | 35 | |

(2) INFORMATION FOR SEQ ID NO: 24:

(i) SEQUENCE CHARACTERISTICS:
(A) LENGTH: 22 amino acids
(B) TYPE: Amino acid
(C) STRANDEDNESS:
(D) TOPOLOGY: Unknown (xi) SEQUENCE DESCRIPTION:SEQ ID NO: 24:

| Gly | Pro | Arg | Leu | Gly | Val | Arg | Ala | Thr | Arg | Lys | Thr | Ser | Glu | Arg |
|---|---|---|---|---|---|---|---|---|---|---|---|---|---|---|
| 1 | | | | 5 | | | | | 10 | | | | | 15 |

| Ser | Gln | Pro | Arg | Gly | Arg | Arg |
|---|---|---|---|---|---|---|
| | | | | 20 | | |

(2) INFORMATION FOR SEQ ID NO: 25:

(i) SEQUENCE CHARACTERISTICS:
(A) LENGTH: 32 amino acids
(B) TYPE: Amino acid
(C) STRANDEDNESS:

( D ) TOPOLOGY: Unknown ( x i ) SEQUENCE DESCRIPTION:SEQ ID NO: 25:

| Val | Gly | Gly | Val | Tyr | Leu | Leu | Pro | Arg | Arg | Gly | Pro | Arg | Leu | Gly |
|---|---|---|---|---|---|---|---|---|---|---|---|---|---|---|
| 1 | | | | 5 | | | | | 10 | | | | | 15 |

| Val | Arg | Ala | Thr | Arg | Lys | Thr | Ser | Glu | Arg | Ser | Gln | Pro | Arg | Gly |
|---|---|---|---|---|---|---|---|---|---|---|---|---|---|---|
| | | | | 20 | | | | | 25 | | | | | 30 |

Arg Arg ( 2 ) INFORMATION FOR SEQ ID NO: 26:

( i ) SEQUENCE CHARACTERISTICS:
        ( A ) LENGTH: 61 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 26:

| Ser | Thr | Ile | Pro | Lys | Pro | Gln | Arg | Lys | Thr | Lys | Arg | Asn | Thr | Asn |
|---|---|---|---|---|---|---|---|---|---|---|---|---|---|---|
| 1 | | | | 5 | | | | | 10 | | | | | 15 |

| Arg | Arg | Pro | Gln | Asp | Val | Lys | Phe | Pro | Gly | Gly | Gly | Gln | Ile | Val |
|---|---|---|---|---|---|---|---|---|---|---|---|---|---|---|
| | | | | 20 | | | | | 25 | | | | | 30 |

| Gly | Gly | Val | Tyr | Leu | Leu | Pro | Arg | Arg | Gly | Pro | Arg | Leu | Gly | Val |
|---|---|---|---|---|---|---|---|---|---|---|---|---|---|---|
| | | | | 35 | | | | | 40 | | | | | 45 |

| Arg | Ala | Thr | Arg | Lys | Thr | Ser | Glu | Arg | Ser | Gln | Pro | Arg | Gly | Arg |
|---|---|---|---|---|---|---|---|---|---|---|---|---|---|---|
| | | | | 50 | | | | | 55 | | | | | 60 |

Arg ( 2 ) INFORMATION FOR SEQ ID NO: 27:

( i ) SEQUENCE CHARACTERISTICS:
        ( A ) LENGTH: 46 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 27:

| Thr | Trp | Ala | Gln | Pro | Gly | Tyr | Pro | Trp | Pro | Leu | Tyr | Gly | Asn | Glu |
|---|---|---|---|---|---|---|---|---|---|---|---|---|---|---|
| 1 | | | | 5 | | | | | 10 | | | | | 15 |

| Gly | Cys | Gly | Trp | Ala | Gly | Trp | Leu | Leu | Ser | Pro | Arg | Gly | Ser | Arg |
|---|---|---|---|---|---|---|---|---|---|---|---|---|---|---|
| | | | | 20 | | | | | 25 | | | | | 30 |

| Pro | Ser | Trp | Gly | Pro | Thr | Asp | Pro | Arg | Arg | Arg | Ser | Arg | Asn | Leu |
|---|---|---|---|---|---|---|---|---|---|---|---|---|---|---|
| | | | | 35 | | | | | 40 | | | | | 45 |

Gly ( 2 ) INFORMATION FOR SEQ ID NO: 28:

( i ) SEQUENCE CHARACTERISTICS:
        ( A ) LENGTH: 56 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 28:

| Ile | Pro | Lys | Val | Arg | Arg | Pro | Glu | Gly | Arg | Thr | Trp | Ala | Gln | Pro |
|---|---|---|---|---|---|---|---|---|---|---|---|---|---|---|
| 1 | | | | 5 | | | | | 10 | | | | | 15 |

| Gly | Tyr | Pro | Trp | Pro | Leu | Tyr | Gly | Asn | Glu | Gly | Cys | Gly | Trp | Ala |
|---|---|---|---|---|---|---|---|---|---|---|---|---|---|---|
| | | | | 20 | | | | | 25 | | | | | 30 |

| Gly | Trp | Leu | Leu | Ser | Pro | Arg | Gly | Ser | Arg | Pro | Ser | Trp | Gly | Pro |
|---|---|---|---|---|---|---|---|---|---|---|---|---|---|---|
| | | | | 35 | | | | | 40 | | | | | 45 |

| Thr | Asp | Pro | Arg | Arg | Arg | Ser | Arg | Asn | Leu | Gly |
|---|---|---|---|---|---|---|---|---|---|---|
| | | | | 50 | | | | | 55 | |

( 2 ) INFORMATION FOR SEQ ID NO: 29:

( i ) SEQUENCE CHARACTERISTICS:
        ( A ) LENGTH: 61 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 29:

```
Gly Arg Arg Gln Pro Ile Pro Lys Val Arg Arg Pro Glu Gly Arg
 1               5                  10                   15

Thr Trp Ala Gln Pro Gly Tyr Pro Trp Pro Leu Tyr Gly Asn Glu
                20                  25                   30

Gly Cys Gly Trp Ala Gly Trp Leu Leu Ser Pro Arg Gly Ser Arg
                35                  40                   45

Pro Ser Trp Gly Pro Thr Asp Pro Arg Arg Arg Ser Arg Asn Leu
                50                  55                   60

Gly
```

( 2 ) INFORMATION FOR SEQ ID NO: 30:

( i ) SEQUENCE CHARACTERISTICS:
        ( A ) LENGTH: 30 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 30:

```
Pro Gly Lys Asn Lys Lys Pro Arg Val Gly Arg Ile Lys Asn Trp
 1               5                  10                   15

Asn Arg Glu Gly Arg Lys Asp Ala Tyr Gln Ile Arg Lys Arg Arg
                20                  25                   30
```

( 2 ) INFORMATION FOR SEQ ID NO: 31:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 31:

```
Lys Glu Lys Glu Lys Thr Ala Thr Asn Asn Pro Gly Lys Asn Lys
 1               5                  10                   15

Lys Pro Arg Val Gly Arg Ile Lys Asn Trp Asn Arg Glu Gly Arg
                20                  25                   30

Lys Asp Ala Tyr Gln Ile Arg Lys Arg Arg
                35                  40
```

( 2 ) INFORMATION FOR SEQ ID NO: 32:

( i ) SEQUENCE CHARACTERISTICS:
        ( A ) LENGTH: 50 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 32:

```
Asn Asp Thr His Lys Lys Gln Arg Arg Tyr Lys Glu Lys Glu Lys
 1               5                  10                   15

Thr Ala Thr Asn Asn Pro Gly Lys Asn Lys Lys Pro Arg Val Gly
                20                  25                   30
```

Arg Ile Lys Asn Trp Asn Arg Glu Gly Arg Lys Asp Ala Tyr Gln
              35                  40                  45

Ile Arg Lys Arg Arg
                50

( 2 ) INFORMATION FOR SEQ ID NO: 33:

( i ) SEQUENCE CHARACTERISTICS:
        ( A ) LENGTH: 61 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 33:

Lys Lys Gly Glu Ala Ser Asn Gly Glu Ala Glu Asn Asp Thr His
 1               5                  10                  15

Lys Lys Gln Arg Arg Tyr Lys Glu Lys Glu Lys Thr Ala Thr Asn
              20                  25                  30

Asn Pro Gly Lys Asn Lys Lys Pro Arg Val Gly Arg Ile Lys Asn
              35                  40                  45

Trp Asn Arg Glu Gly Arg Lys Asp Ala Tyr Gln Ile Arg Lys Arg
              50                  55                  60

Arg ( 2 ) INFORMATION FOR SEQ ID NO: 34:

( i ) SEQUENCE CHARACTERISTICS:
        ( A ) LENGTH: 37 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 34:

Gln Gly Trp Gly Pro Ile Ser Tyr Ala Asn Gly Ser Gly Pro Asp
 1               5                  10                  15

Gln Arg Pro Tyr Cys Trp His Tyr Pro Pro Lys Pro Cys Gly Ile
              20                  25                  30

Val Pro Ala Lys Ser Val Cys
              35

( 2 ) INFORMATION FOR SEQ ID NO: 35:

( i ) SEQUENCE CHARACTERISTICS:
        ( A ) LENGTH: 45 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 35:

Cys Arg Pro Leu Thr Asp Phe Asp Gln Gly Trp Gly Pro Ile Ser
 1               5                  10                  15

Tyr Ala Asn Gly Ser Gly Pro Asp Gln Arg Pro Tyr Cys Trp His
              20                  25                  30

Tyr Pro Pro Lys Pro Cys Gly Ile Val Pro Ala Lys Ser Val Cys
              35                  40                  45

( 2 ) INFORMATION FOR SEQ ID NO: 36:

( i ) SEQUENCE CHARACTERISTICS:
        ( A ) LENGTH: 52 amino acids
        ( B ) TYPE: Amino acid
        ( C ) STRANDEDNESS:
        ( D ) TOPOLOGY: Unknown (x i) SEQUENCE DESCRIPTION:SEQ ID NO: 36:

```
Cys Pro Glu Arg Leu Ala Ser Cys Arg Pro Leu Thr Asp Phe Asp
 1               5                  10                  15

Gln Gly Trp Gly Pro Ile Ser Tyr Ala Asn Gly Ser Gly Pro Asp
                20                  25                  30

Gln Arg Pro Tyr Cys Trp His Tyr Pro Pro Lys Pro Cys Gly Ile
                35                  40                  45

Val Pro Ala Lys Ser Val Cys
                50
```

(2) INFORMATION FOR SEQ ID NO: 37:

(i) SEQUENCE CHARACTERISTICS:
        (A) LENGTH: 26 amino acids
        (B) TYPE: Amino acid
        (C) STRANDEDNESS:
        (D) TOPOLOGY: Unknown (x i) SEQUENCE DESCRIPTION:SEQ ID NO: 37:

```
Arg Pro Tyr Cys Trp His Tyr Pro Pro Lys Pro Cys Gly Ile Val
 1               5                  10                  15

Pro Ala Lys Ser Val Cys Gly Pro Val Tyr Cys
                20                  25
```

(2) INFORMATION FOR SEQ ID NO: 38:

(i) SEQUENCE CHARACTERISTICS:
        (A) LENGTH: 34 amino acids
        (B) TYPE: Amino acid
        (C) STRANDEDNESS:
        (D) TOPOLOGY: Unknown (x i) SEQUENCE DESCRIPTION:SEQ ID NO: 38:

```
Ala Asn Gly Ser Gly Pro Asp Gln Arg Pro Tyr Cys Trp His Tyr
 1               5                  10                  15

Pro Pro Lys Pro Cys Gly Ile Val Pro Ala Lys Ser Val Cys Gly
                20                  25                  30

Pro Val Tyr Cys
```

(2) INFORMATION FOR SEQ ID NO: 39:

(i) SEQUENCE CHARACTERISTICS:
        (A) LENGTH: 50 amino acids
        (B) TYPE: Amino acid
        (C) STRANDEDNESS:
        (D) TOPOLOGY: Unknown (x i) SEQUENCE DESCRIPTION:SEQ ID NO: 39:

```
Cys Arg Pro Leu Thr Asp Phe Asp Gln Gly Trp Gly Pro Ile Ser
 1               5                  10                  15

Tyr Ala Asn Gly Ser Gly Pro Asp Gln Arg Pro Tyr Cys Trp His
                20                  25                  30

Tyr Pro Pro Lys Pro Cys Gly Ile Val Pro Ala Lys Ser Val Cys
                35                  40                  45

Gly Pro Val Tyr Cys
                50
```

(2) INFORMATION FOR SEQ ID NO: 40:

(i) SEQUENCE CHARACTERISTICS:
        (A) LENGTH: 57 amino acids
        (B) TYPE: Amino acid
        (C) STRANDEDNESS:

( D ) TOPOLOGY: Unknown ( x i ) SEQUENCE DESCRIPTION:SEQ ID NO: 40:

| Cys | Pro | Glu | Arg | Leu | Ala | Ser | Cys | Arg | Pro | Leu | Thr | Asp | Phe | Asp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gln | Gly | Trp | Gly | Pro | Ile | Ser | Tyr | Ala | Asn | Gly | Ser | Gly | Pro | Asp |
|-----|-----|-----|-----|-----|-----|-----|-----|-----|-----|-----|-----|-----|-----|-----|
|     |     |     |     | 20  |     |     |     |     | 25  |     |     |     |     | 30  |

| Gln | Arg | Pro | Tyr | Cys | Trp | His | Tyr | Pro | Pro | Lys | Pro | Cys | Gly | Ile |
|-----|-----|-----|-----|-----|-----|-----|-----|-----|-----|-----|-----|-----|-----|-----|
|     |     |     |     | 35  |     |     |     |     | 40  |     |     |     |     | 45  |

| Val | Pro | Ala | Lys | Ser | Val | Cys | Gly | Pro | Val | Tyr | Cys |
|-----|-----|-----|-----|-----|-----|-----|-----|-----|-----|-----|-----|
|     |     |     |     | 50  |     |     |     |     | 55  |     |     |

( 2 ) INFORMATION FOR SEQ ID NO: 41:

( i ) SEQUENCE CHARACTERISTICS:
      ( A ) LENGTH: 34 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 41:

| Val | Phe | Val | Leu | Asn | Asn | Thr | Arg | Pro | Pro | Leu | Gly | Asn | Trp | Phe |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gly | Cys | Thr | Trp | Met | Asn | Ser | Thr | Gly | Phe | Thr | Lys | Val | Cys | Gly |
|-----|-----|-----|-----|-----|-----|-----|-----|-----|-----|-----|-----|-----|-----|-----|
|     |     |     |     | 20  |     |     |     |     | 25  |     |     |     |     | 30  |

| Ala | Pro | Pro | Cys |
|-----|-----|-----|-----|

( 2 ) INFORMATION FOR SEQ ID NO: 42:

( i ) SEQUENCE CHARACTERISTICS:
      ( A ) LENGTH: 42 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 42:

| Ser | Trp | Gly | Glu | Asn | Asp | Thr | Asp | Val | Phe | Val | Leu | Asn | Asn | Thr |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Arg | Pro | Pro | Leu | Gly | Asn | Trp | Phe | Gly | Cys | Thr | Trp | Met | Asn | Ser |
|-----|-----|-----|-----|-----|-----|-----|-----|-----|-----|-----|-----|-----|-----|-----|
|     |     |     |     | 20  |     |     |     |     | 25  |     |     |     |     | 30  |

| Thr | Gly | Phe | Thr | Lys | Val | Cys | Gly | Ala | Pro | Pro | Cys |
|-----|-----|-----|-----|-----|-----|-----|-----|-----|-----|-----|-----|
|     |     |     |     | 35  |     |     |     |     | 40  |     |     |

( 2 ) INFORMATION FOR SEQ ID NO: 43:

( i ) SEQUENCE CHARACTERISTICS:
      ( A ) LENGTH: 50 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 43:

| Asp | Arg | Ser | Gly | Ala | Pro | Thr | Tyr | Ser | Trp | Gly | Glu | Asn | Asp | Thr |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Asp | Val | Phe | Val | Leu | Asn | Asn | Thr | Arg | Pro | Pro | Leu | Gly | Asn | Trp |
|-----|-----|-----|-----|-----|-----|-----|-----|-----|-----|-----|-----|-----|-----|-----|
|     |     |     |     | 20  |     |     |     |     | 25  |     |     |     |     | 30  |

| Phe | Gly | Cys | Thr | Trp | Met | Asn | Ser | Thr | Gly | Phe | Thr | Lys | Val | Cys |
|-----|-----|-----|-----|-----|-----|-----|-----|-----|-----|-----|-----|-----|-----|-----|
|     |     |     |     | 35  |     |     |     |     | 40  |     |     |     |     | 45  |

| Gly | Ala | Pro | Pro | Cys |
|-----|-----|-----|-----|-----|
|     |     |     |     | 50  |

( 2 ) INFORMATION FOR SEQ ID NO: 44:

( i ) SEQUENCE CHARACTERISTICS:
   ( A ) LENGTH: 42 amino acids
   ( B ) TYPE: Amino acid
   ( C ) STRANDEDNESS:
   ( D ) TOPOLOGY: Unknown ( x i ) SEQUENCE DESCRIPTION:SEQ ID NO: 44:

```
Leu His Cys Pro Thr Asp Cys Phe Arg Lys His Pro Asp Ala Thr
1               5                   10                  15

Tyr Ser Arg Cys Gly Ser Gly Pro Trp Ile Thr Pro Arg Cys Leu
                20                  25                  30

Val Asp Tyr Pro Tyr Arg Leu Trp His Trp Pro Cys
                35                  40
```

( 2 ) INFORMATION FOR SEQ ID NO: 45:

( i ) SEQUENCE CHARACTERISTICS:
      ( A ) LENGTH: 23 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 45:

```
Glu Ala Ala Cys Asn Trp Thr Arg Gly Glu Arg Cys Asp Leu Glu
1               5                   10                  15

Asp Arg Asp Arg Ser Glu Leu Ser
                20
```

( 2 ) INFORMATION FOR SEQ ID NO: 46:

( i ) SEQUENCE CHARACTERISTICS:
      ( A ) LENGTH: 31 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 46:

```
Val Gly Gly Val Glu His Arg Leu Glu Ala Ala Cys Asn Trp Thr
1               5                   10                  15

Arg Gly Glu Arg Cys Asp Leu Glu Asp Arg Asp Arg Ser Glu Leu
                20                  25                  30

Ser
```

( 2 ) INFORMATION FOR SEQ ID NO: 47:

( i ) SEQUENCE CHARACTERISTICS:
      ( A ) LENGTH: 39 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 47:

```
Thr Ile Phe Lys Ile Arg Met Tyr Val Gly Gly Val Glu His Arg
1               5                   10                  15

Leu Glu Ala Ala Cys Asn Trp Thr Arg Gly Glu Arg Cys Asp Leu
                20                  25                  30

Glu Asp Arg Asp Arg Ser Glu Leu Ser
                35
```

( 2 ) INFORMATION FOR SEQ ID NO: 48:

( i ) SEQUENCE CHARACTERISTICS:
      ( A ) LENGTH: 41 amino acids
      ( B ) TYPE: Amino acid ( C ) STRANDEDNESS:
( D ) TOPOLOGY: Unknown ( x i ) SEQUENCE DESCRIPTION:SEQ ID NO: 48:

| Pro | Val | Val | Pro | Gln | Ser | Phe | Gln | Val | Ala | His | Leu | His | Ala | Pro |
|---|---|---|---|---|---|---|---|---|---|---|---|---|---|---|
| 1 | | | | 5 | | | | | 10 | | | | | 15 |
| Thr | Gly | Ser | Gly | Lys | Ser | Thr | Lys | Val | Pro | Ala | Ala | Tyr | Ala | Ala |
| | | | | 20 | | | | | 25 | | | | | 30 |
| Gln | Gly | Tyr | Lys | Val | Leu | Val | Leu | Asn | Pro | Ser | | | | |
| | | | | 35 | | | | | 40 | | | | | |

( 2 ) INFORMATION FOR SEQ ID NO: 49:

( i ) SEQUENCE CHARACTERISTICS:
( A ) LENGTH: 55 amino acids
( B ) TYPE: Amino acid
( C ) STRANDEDNESS:
( D ) TOPOLOGY: Unknown ( x i ) SEQUENCE DESCRIPTION:SEQ ID NO: 49:

| Thr | Thr | Met | Arg | Ser | Pro | Val | Phe | Thr | Asp | Asn | Ser | Ser | Pro | Pro |
|---|---|---|---|---|---|---|---|---|---|---|---|---|---|---|
| 1 | | | | 5 | | | | | 10 | | | | | 15 |
| Val | Val | Pro | Gln | Ser | Phe | Gln | Val | Ala | His | Leu | His | Ala | Pro | Thr |
| | | | | 20 | | | | | 25 | | | | | 30 |
| Gly | Ser | Gly | Lys | Ser | Thr | Lys | Val | Pro | Ala | Ala | Tyr | Ala | Ala | Gln |
| | | | | 35 | | | | | 40 | | | | | 45 |
| Gly | Tyr | Lys | Val | Leu | Val | Leu | Asn | Pro | Ser | | | | | |
| | | | | 50 | | | | | 55 | | | | | |

( 2 ) INFORMATION FOR SEQ ID NO: 50:

( i ) SEQUENCE CHARACTERISTICS:
( A ) LENGTH: 66 amino acids
( B ) TYPE: Amino acid
( C ) STRANDEDNESS:
( D ) TOPOLOGY: Unknown ( x i ) SEQUENCE DESCRIPTION:SEQ ID NO: 50:

| Ala | Val | Asp | Phe | Ile | Pro | Val | Glu | Asn | Leu | Glu | Thr | Thr | Met | Arg |
|---|---|---|---|---|---|---|---|---|---|---|---|---|---|---|
| 1 | | | | 5 | | | | | 10 | | | | | 15 |
| Ser | Pro | Val | Phe | Thr | Asp | Asn | Ser | Ser | Pro | Pro | Val | Val | Pro | Gln |
| | | | | 20 | | | | | 25 | | | | | 30 |
| Ser | Phe | Gln | Val | Ala | His | Leu | His | Ala | Pro | Thr | Gly | Ser | Gly | Lys |
| | | | | 35 | | | | | 40 | | | | | 45 |
| Ser | Thr | Lys | Val | Pro | Ala | Ala | Tyr | Ala | Ala | Gln | Gly | Tyr | Lys | Val |
| | | | | 50 | | | | | 55 | | | | | 60 |
| Leu | Val | Leu | Asn | Pro | Ser | | | | | | | | | |
| | | | | 65 | | | | | | | | | | |

( 2 ) INFORMATION FOR SEQ ID NO: 51:

( i ) SEQUENCE CHARACTERISTICS:
( A ) LENGTH: 29 amino acids
( B ) TYPE: Amino acid
( C ) STRANDEDNESS:
( D ) TOPOLOGY: Unknown ( x i ) SEQUENCE DESCRIPTION:SEQ ID NO: 51:

| Pro | Val | Val | Pro | Gln | Ser | Phe | Gln | Val | Ala | His | Leu | His | Ala | Pro |
|---|---|---|---|---|---|---|---|---|---|---|---|---|---|---|
| 1 | | | | 5 | | | | | 10 | | | | | 15 |
| Thr | Gly | Ser | Gly | Lys | Ser | Thr | Lys | Val | Pro | Ala | Ala | Tyr | Ala | |
| | | | | 20 | | | | | 25 | | | | | |

( 2 ) INFORMATION FOR SEQ ID NO: 52:

( i ) SEQUENCE CHARACTERISTICS:
        ( A ) LENGTH: 36 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 52:

```
Phe Thr Asp Asn Ser Ser Pro Pro Val Val Pro Gln Ser Phe Gln
 1               5                  10                  15

Val Ala His Leu His Ala Pro Thr Gly Ser Gly Lys Ser Thr Lys
                 20                  25                  30

Val Pro Ala Ala Tyr Ala
                 35
```

( 2 ) INFORMATION FOR SEQ ID NO: 53:

( i ) SEQUENCE CHARACTERISTICS:
        ( A ) LENGTH: 48 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 53:

```
Val Glu Asn Leu Glu Thr Thr Met Arg Ser Pro Val Phe Thr Asp
 1               5                  10                  15

Asn Ser Ser Pro Pro Val Val Pro Gln Ser Phe Gln Val Ala His
                 20                  25                  30

Leu His Ala Pro Thr Gly Ser Gly Lys Ser Thr Lys Val Pro Ala
                 35                  40                  45

Ala Tyr Ala
```

( 2 ) INFORMATION FOR SEQ ID NO: 54:

( i ) SEQUENCE CHARACTERISTICS:
        ( A ) LENGTH: 54 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 54:

```
Ala Val Asp Phe Ile Pro Val Glu Asn Leu Glu Thr Thr Met Arg
 1               5                  10                  15

Ser Pro Val Phe Thr Asp Asn Ser Ser Pro Pro Val Val Pro Gln
                 20                  25                  30

Ser Phe Gln Val Ala His Leu His Ala Pro Thr Gly Ser Gly Lys
                 35                  40                  45

Ser Thr Lys Val Pro Ala Ala Tyr Ala
                 50
```

( 2 ) INFORMATION FOR SEQ ID NO: 55:

( i ) SEQUENCE CHARACTERISTICS:
        ( A ) LENGTH: 38 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 55:

```
Arg Thr Ile Thr Thr Gly Ser Pro Ile Thr Tyr Ser Thr Tyr Gly
 1               5                  10                  15

Lys Phe Leu Ala Asp Gly Gly Cys Ser Gly Gly Ala Tyr Asp Ile
```

Ile Ile Cys Asp Glu Cys His Ser
              35

( 2 ) INFORMATION FOR SEQ ID NO: 56:

( i ) SEQUENCE CHARACTERISTICS:
    ( A ) LENGTH: 71 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 56:

Lys Val Leu Val Leu Asn Pro Ser Val Ala Ala Thr Leu Gly Phe
1               5                  10                 15

Gly Ala Tyr Met Ser Lys Ala His Gly Ile Asp Pro Asn Ile Arg
                20                  25                 30

Thr Gly Val Arg Thr Ile Thr Thr Gly Ser Pro Ile Thr Tyr Ser
                35                  40                 45

Thr Tyr Gly Lys Phe Leu Ala Asp Gly Gly Cys Ser Gly Gly Ala
                50                  55                 60

Tyr Asp Ile Ile Ile Cys Asp Glu Cys His Ser
                65                  70

( 2 ) INFORMATION FOR SEQ ID NO: 57:

( i ) SEQUENCE CHARACTERISTICS:
    ( A ) LENGTH: 94 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 57:

His Leu His Ala Pro Thr Gly Ser Gly Lys Ser Thr Lys Val Pro
1               5                  10                 15

Ala Ala Tyr Ala Ala Gln Gly Tyr Lys Val Leu Val Leu Asn Pro
                20                  25                 30

Ser Val Ala Ala Thr Leu Gly Phe Gly Ala Tyr Met Ser Lys Ala
                35                  40                 45

His Gly Ile Asp Pro Asn Ile Arg Thr Gly Val Arg Thr Ile Thr
                50                  55                 60

Thr Gly Ser Pro Ile Thr Tyr Ser Thr Tyr Gly Lys Phe Leu Ala
                65                  70                 75

Asp Gly Gly Cys Ser Gly Gly Ala Tyr Asp Ile Ile Ile Cys Asp
                80                  85                 90

Glu Cys His Ser ( 2 ) INFORMATION FOR SEQ ID NO: 58:

( i ) SEQUENCE CHARACTERISTICS:
    ( A ) LENGTH: 117 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 58:

Thr Met Arg Ser Pro Val Phe Thr Asp Asn Ser Ser Pro Pro Val
1               5                  10                 15

Val Pro Gln Ser Phe Gln Val Ala His Leu His Ala Pro Thr Gly
                20                  25                 30

Ser Gly Lys Ser Thr Lys Val Pro Ala Ala Tyr Ala Ala Gln Gly

|       |       |       |       | 35    |       |       |       |       | 40    |       |       |       |       | 45    |
|-------|-------|-------|-------|-------|-------|-------|-------|-------|-------|-------|-------|-------|-------|-------|
| Tyr   | Lys   | Val   | Leu   | Val   | Leu   | Asn   | Pro   | Ser   | Val   | Ala   | Ala   | Thr   | Leu   | Gly   |
|       |       |       |       | 50    |       |       |       |       | 55    |       |       |       |       | 60    |
| Phe   | Gly   | Ala   | Tyr   | Met   | Ser   | Lys   | Ala   | His   | Gly   | Ile   | Asp   | Pro   | Asn   | Ile   |
|       |       |       |       | 65    |       |       |       |       | 70    |       |       |       |       | 75    |
| Arg   | Thr   | Gly   | Val   | Arg   | Thr   | Ile   | Thr   | Thr   | Gly   | Ser   | Pro   | Ile   | Thr   | Tyr   |
|       |       |       |       | 80    |       |       |       |       | 85    |       |       |       |       | 90    |
| Ser   | Thr   | Tyr   | Gly   | Lys   | Phe   | Leu   | Ala   | Asp   | Gly   | Gly   | Cys   | Ser   | Gly   | Gly   |
|       |       |       |       | 95    |       |       |       |       | 100   |       |       |       |       | 105   |
| Ala   | Tyr   | Asp   | Ile   | Ile   | Ile   | Cys   | Asp   | Glu   | Cys   | His   | Ser   |       |       |       |
|       |       |       |       | 110   |       |       |       |       | 115   |       |       |       |       |       |

( 2 ) INFORMATION FOR SEQ ID NO: 59:

( i ) SEQUENCE CHARACTERISTICS:
        ( A ) LENGTH: 37 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 59:

| Thr | Val | Leu | Asp | Gln | Ala | Glu | Thr | Ala | Gly | Ala | Arg | Leu | Val | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Leu | Ala | Thr | Ala | Thr | Pro | Pro | Gly | Ser | Val | Thr | Val | Pro | His | Pro |
|     |     |     |     | 20  |     |     |     |     | 25  |     |     |     |     | 30  |
| Asn | Ile | Glu | Glu | Val | Ala | Leu |     |     |     |     |     |     |     |     |
|     |     |     |     | 35  |     |     |     |     |     |     |     |     |     |     |

( 2 ) INFORMATION FOR SEQ ID NO: 60:

( i ) SEQUENCE CHARACTERISTICS:
        ( A ) LENGTH: 64 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 60:

| Gly | Cys | Ser | Gly | Gly | Ala | Tyr | Asp | Ile | Ile | Ile | Cys | Asp | Glu | Cys |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| His | Ser | Thr | Asp | Ala | Thr | Ser | Ile | Leu | Gly | Ile | Gly | Thr | Val | Leu |
|     |     |     |     | 20  |     |     |     |     | 25  |     |     |     |     | 30  |
| Asp | Gln | Ala | Glu | Thr | Ala | Gly | Ala | Arg | Leu | Val | Val | Leu | Ala | Thr |
|     |     |     |     | 35  |     |     |     |     | 40  |     |     |     |     | 45  |
| Ala | Thr | Pro | Pro | Gly | Ser | Val | Thr | Val | Pro | His | Pro | Asn | Ile | Glu |
|     |     |     |     | 50  |     |     |     |     | 55  |     |     |     |     | 60  |
| Glu | Val | Ala | Leu |     |     |     |     |     |     |     |     |     |     |     |

( 2 ) INFORMATION FOR SEQ ID NO: 61:

( i ) SEQUENCE CHARACTERISTICS:
        ( A ) LENGTH: 97 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 61:

| Ala | His | Gly | Ile | Asp | Pro | Asn | Ile | Arg | Thr | Gly | Val | Arg | Thr | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Thr | Thr | Gly | Ser | Pro | Ile | Thr | Tyr | Ser | Thr | Tyr | Gly | Lys | Phe | Leu |
|     |     |     |     | 20  |     |     |     |     | 25  |     |     |     |     | 30  |
| Ala | Asp | Gly | Gly | Cys | Ser | Gly | Gly | Ala | Tyr | Asp | Ile | Ile | Ile | Cys |

```
                          35                    40                           45
Asp  Glu  Cys  His  Ser  Thr  Asp  Ala  Thr  Ser  Ile  Leu  Gly  Ile  Gly
                    50                    55                           60

Thr  Val  Leu  Asp  Gln  Ala  Glu  Thr  Ala  Gly  Ala  Arg  Leu  Val  Val
                    65                    70                           75

Leu  Ala  Thr  Ala  Thr  Pro  Pro  Gly  Ser  Val  Thr  Val  Pro  His  Pro
                    80                    85                           90

Asn  Ile  Glu  Glu  Val  Ala  Leu
                    95
```

( 2 ) INFORMATION FOR SEQ ID NO: 62:

( i ) SEQUENCE CHARACTERISTICS:
        ( A ) LENGTH: 120 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 62:

```
Gly  Tyr  Lys  Val  Leu  Val  Leu  Asn  Pro  Ser  Val  Ala  Ala  Thr  Leu
 1                   5                    10                           15

Gly  Phe  Gly  Ala  Tyr  Met  Ser  Lys  Ala  His  Gly  Ile  Asp  Pro  Asn
                    20                    25                           30

Ile  Arg  Thr  Gly  Val  Arg  Thr  Ile  Thr  Thr  Gly  Ser  Pro  Ile  Thr
                    35                    40                           45

Tyr  Ser  Thr  Tyr  Gly  Lys  Phe  Leu  Ala  Asp  Gly  Gly  Cys  Ser  Gly
                    50                    55                           60

Gly  Ala  Tyr  Asp  Ile  Ile  Ile  Cys  Asp  Glu  Cys  His  Ser  Thr  Asp
                    65                    70                           75

Ala  Thr  Ser  Ile  Leu  Gly  Ile  Gly  Thr  Val  Leu  Asp  Gln  Ala  Glu
                    80                    85                           90

Thr  Ala  Gly  Ala  Arg  Leu  Val  Val  Leu  Ala  Thr  Ala  Thr  Pro  Pro
                    95                    100                          105

Gly  Ser  Val  Thr  Val  Pro  His  Pro  Asn  Ile  Glu  Glu  Val  Ala  Leu
                    110                   115                          120
```

( 2 ) INFORMATION FOR SEQ ID NO: 63:

( i ) SEQUENCE CHARACTERISTICS:
        ( A ) LENGTH: 29 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 63:

```
Tyr  Gly  Lys  Phe  Leu  Ala  Asp  Gly  Gly  Cys  Ser  Gly  Gly  Ala  Tyr
 1                   5                    10                           15

Asp  Ile  Ile  Ile  Cys  Asp  Glu  Cys  His  Ser  Thr  Asp  Ala  Thr
                    20                    25
```

( 2 ) INFORMATION FOR SEQ ID NO: 64:

( i ) SEQUENCE CHARACTERISTICS:
        ( A ) LENGTH: 39 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 64:

```
Thr  Thr  Gly  Ser  Pro  Ile  Thr  Tyr  Ser  Thr  Tyr  Gly  Lys  Phe  Leu
 1                   5                    10                           15
```

| Ala | Asp | Gly | Gly | Cys | Ser | Gly | Gly | Ala | Tyr | Asp | Ile | Ile | Ile | Cys |
|---|---|---|---|---|---|---|---|---|---|---|---|---|---|---|
| | | | | 20 | | | | | 25 | | | | | |

| Asp | Glu | Cys | His | Ser | Thr | Asp | Ala | Thr |
|---|---|---|---|---|---|---|---|---|
| | | | | 35 | | | | |

( 2 ) INFORMATION FOR SEQ ID NO: 65:

( i ) SEQUENCE CHARACTERISTICS:
        ( A ) LENGTH: 49 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 65:

| Pro | Asn | Ile | Arg | Thr | Gly | Val | Arg | Thr | Ile | Thr | Thr | Gly | Ser | Pro |
|---|---|---|---|---|---|---|---|---|---|---|---|---|---|---|
| 1 | | | | 5 | | | | | 10 | | | | | 15 |

| Ile | Thr | Tyr | Ser | Thr | Tyr | Gly | Lys | Phe | Leu | Ala | Asp | Gly | Gly | Cys |
|---|---|---|---|---|---|---|---|---|---|---|---|---|---|---|
| | | | | 20 | | | | | 25 | | | | | 30 |

| Ser | Gly | Gly | Ala | Tyr | Asp | Ile | Ile | Ile | Cys | Asp | Glu | Cys | His | Ser |
|---|---|---|---|---|---|---|---|---|---|---|---|---|---|---|
| | | | | 35 | | | | | 40 | | | | | 45 |

| Thr | Asp | Ala | Thr |
|---|---|---|---|
| | | | |

( 2 ) INFORMATION FOR SEQ ID NO: 66:

( i ) SEQUENCE CHARACTERISTICS:
        ( A ) LENGTH: 59 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 66:

| Ala | Tyr | Met | Ser | Lys | Ala | His | Gly | Ile | Asp | Pro | Asn | Ile | Arg | Thr |
|---|---|---|---|---|---|---|---|---|---|---|---|---|---|---|
| 1 | | | | 5 | | | | | 10 | | | | | 15 |

| Gly | Val | Arg | Thr | Ile | Thr | Thr | Gly | Ser | Pro | Ile | Thr | Tyr | Ser | Thr |
|---|---|---|---|---|---|---|---|---|---|---|---|---|---|---|
| | | | | 20 | | | | | 25 | | | | | 30 |

| Tyr | Gly | Lys | Phe | Leu | Ala | Asp | Gly | Gly | Cys | Ser | Gly | Gly | Ala | Tyr |
|---|---|---|---|---|---|---|---|---|---|---|---|---|---|---|
| | | | | 35 | | | | | 40 | | | | | 45 |

| Asp | Ile | Ile | Ile | Cys | Asp | Glu | Cys | His | Ser | Thr | Asp | Ala | Thr |
|---|---|---|---|---|---|---|---|---|---|---|---|---|---|
| | | | | 50 | | | | | 55 | | | | |

( 2 ) INFORMATION FOR SEQ ID NO: 67:

( i ) SEQUENCE CHARACTERISTICS:
        ( A ) LENGTH: 68 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 67:

| Ser | Val | Ala | Ala | Thr | Leu | Gly | Phe | Gly | Ala | Tyr | Met | Ser | Lys | Ala |
|---|---|---|---|---|---|---|---|---|---|---|---|---|---|---|
| 1 | | | | 5 | | | | | 10 | | | | | 15 |

| His | Gly | Ile | Asp | Pro | Asn | Ile | Arg | Thr | Gly | Val | Arg | Thr | Ile | Thr |
|---|---|---|---|---|---|---|---|---|---|---|---|---|---|---|
| | | | | 20 | | | | | 25 | | | | | 30 |

| Thr | Gly | Ser | Pro | Ile | Thr | Tyr | Ser | Thr | Tyr | Gly | Lys | Phe | Leu | Ala |
|---|---|---|---|---|---|---|---|---|---|---|---|---|---|---|
| | | | | 35 | | | | | 40 | | | | | 45 |

| Asp | Gly | Gly | Cys | Ser | Gly | Gly | Ala | Tyr | Asp | Ile | Ile | Ile | Cys | Asp |
|---|---|---|---|---|---|---|---|---|---|---|---|---|---|---|
| | | | | 50 | | | | | 55 | | | | | 60 |

| Glu | Cys | His | Ser | Thr | Asp | Ala | Thr |
|---|---|---|---|---|---|---|---|
| | | | | 65 | | | |

( 2 ) INFORMATION FOR SEQ ID NO: 68:

( i ) SEQUENCE CHARACTERISTICS:
    ( A ) LENGTH: 77 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 68:

```
Gly Tyr Lys Val Leu Val Leu Asn Pro Ser Val Ala Ala Thr Leu
 1               5                  10                  15

Gly Phe Gly Ala Tyr Met Ser Lys Ala His Gly Ile Asp Pro Asn
                20                  25                  30

Ile Arg Thr Gly Val Arg Thr Ile Thr Thr Gly Ser Pro Ile Thr
                35                  40                  45

Tyr Ser Thr Tyr Gly Lys Phe Leu Ala Asp Gly Gly Cys Ser Gly
                50                  55                  60

Gly Ala Tyr Asp Ile Ile Ile Cys Asp Glu Cys His Ser Thr Asp
                65                  70                  75

Ala Thr
```

( 2 ) INFORMATION FOR SEQ ID NO: 69:

( i ) SEQUENCE CHARACTERISTICS:
    ( A ) LENGTH: 30 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 69:

```
Pro Phe Tyr Gly Lys Ala Ile Pro Leu Glu Val Ile Lys Gly Gly
 1               5                  10                  15

Arg His Leu Ile Phe Cys His Ser Lys Lys Cys Asp Glu Leu
                20                  25                  30
```

( 2 ) INFORMATION FOR SEQ ID NO: 70:

( i ) SEQUENCE CHARACTERISTICS:
    ( A ) LENGTH: 40 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 70:

```
Glu Val Ala Leu Ser Thr Thr Gly Glu Ile Pro Phe Tyr Gly Lys
 1               5                  10                  15

Ala Ile Pro Leu Glu Val Ile Lys Gly Gly Arg His Leu Ile Phe
                20                  25                  30

Cys His Ser Lys Lys Lys Cys Asp Glu Leu
                35                  40
```

( 2 ) INFORMATION FOR SEQ ID NO: 71:

( i ) SEQUENCE CHARACTERISTICS:
    ( A ) LENGTH: 50 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 71:

```
Ser Val Thr Val Pro His Pro Asn Ile Glu Glu Val Ala Leu Ser
 1               5                  10                  15

Thr Thr Gly Glu Ile Pro Phe Tyr Gly Lys Ala Ile Pro Leu Glu
                20                  25                  30

Val Ile Lys Gly Gly Arg His Leu Ile Phe Cys His Ser Lys Lys
```

35                    40                    45
Lys Cys Asp Glu Leu
                50

( 2 ) INFORMATION FOR SEQ ID NO: 72:

( i ) SEQUENCE CHARACTERISTICS:
            ( A ) LENGTH: 73 amino acids
            ( B ) TYPE: Amino acid
            ( C ) STRANDEDNESS:
            ( D ) TOPOLOGY: Unknown ( x i ) SEQUENCE DESCRIPTION:SEQ ID NO: 72:

Thr Val Leu Asp Gln Ala Glu Thr Ala Gly Ala Arg Leu Val Val
 1               5                  10                  15

Leu Ala Thr Ala Thr Pro Pro Gly Ser Val Thr Val Pro His Pro
                20                  25                  30

Asn Ile Glu Glu Val Ala Leu Ser Thr Thr Gly Glu Ile Pro Phe
                35                  40                  45

Tyr Gly Lys Ala Ile Pro Leu Glu Val Ile Lys Gly Gly Arg His
                50                  55                  60

Leu Ile Phe Cys His Ser Lys Lys Lys Cys Asp Glu Leu
                65                  70

( 2 ) INFORMATION FOR SEQ ID NO: 73:

( i ) SEQUENCE CHARACTERISTICS:
            ( A ) LENGTH: 97 amino acids
            ( B ) TYPE: Amino acid
            ( C ) STRANDEDNESS:
            ( D ) TOPOLOGY: Unknown ( x i ) SEQUENCE DESCRIPTION:SEQ ID NO: 73:

Gly Gly Ala Tyr Asp Ile Ile Ile Cys Asp Glu Cys His Ser Thr
 1               5                  10                  15

Asp Ala Thr Ser Ile Leu Gly Ile Gly Thr Val Leu Asp Gln Ala
                20                  25                  30

Glu Thr Ala Gly Ala Arg Leu Val Val Leu Ala Thr Ala Thr Pro
                35                  40                  45

Pro Gly Ser Val Thr Val Pro His Pro Asn Ile Glu Glu Val Ala
                50                  55                  60

Leu Ser Thr Thr Gly Glu Ile Pro Phe Tyr Gly Lys Ala Ile Pro
                65                  70                  75

Leu Glu Val Ile Lys Gly Gly Arg His Leu Ile Phe Cys His Ser
                80                  85                  90

Lys Lys Lys Cys Asp Glu Leu
                95

( 2 ) INFORMATION FOR SEQ ID NO: 74:

( i ) SEQUENCE CHARACTERISTICS:
            ( A ) LENGTH: 121 amino acids
            ( B ) TYPE: Amino acid
            ( C ) STRANDEDNESS:
            ( D ) TOPOLOGY: Unknown ( x i ) SEQUENCE DESCRIPTION:SEQ ID NO: 74:

Arg Thr Ile Thr Thr Gly Ser Pro Ile Thr Tyr Ser Thr Tyr Gly
 1               5                  10                  15

Lys Phe Leu Ala Asp Gly Gly Cys Ser Gly Gly Ala Tyr Asp Ile
                20                  25                  30

```
Ile  Ile  Cys  Asp  Glu  Cys  His  Ser  Thr  Asp  Ala  Thr  Ser  Ile  Leu
               35                    40                         45

Gly  Ile  Gly  Thr  Val  Leu  Asp  Gln  Ala  Glu  Thr  Ala  Gly  Ala  Arg
               50                    55                         60

Leu  Val  Val  Leu  Ala  Thr  Ala  Thr  Pro  Pro  Gly  Ser  Val  Thr  Val
               65                    70                         75

Pro  His  Pro  Asn  Ile  Glu  Glu  Val  Ala  Leu  Ser  Thr  Thr  Gly  Glu
               80                    85                         90

Ile  Pro  Phe  Tyr  Gly  Lys  Ala  Ile  Pro  Leu  Glu  Val  Ile  Lys  Gly
               95                   100                        105

Gly  Arg  His  Leu  Ile  Phe  Cys  His  Ser  Lys  Lys  Cys  Asp  Glu
              110                   115                        120

Leu
```

( 2 ) INFORMATION FOR SEQ ID NO: 75:

( i ) SEQUENCE CHARACTERISTICS:
        ( A ) LENGTH: 37 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 75:

```
Gly  Cys  Ser  Gly  Gly  Ala  Tyr  Asp  Ile  Ile  Ile  Cys  Asp  Glu  Cys
 1                    5                    10                         15

His  Ser  Thr  Asp  Ala  Thr  Ser  Ile  Leu  Gly  Ile  Gly  Thr  Val  Leu
               20                    25                         30

Asp  Gln  Ala  Glu  Thr  Ala  Gly
               35
```

( 2 ) INFORMATION FOR SEQ ID NO: 76:

( i ) SEQUENCE CHARACTERISTICS:
        ( A ) LENGTH: 42 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 76:

```
Phe  Leu  Ala  Asp  Gly  Gly  Cys  Ser  Gly  Gly  Ala  Tyr  Asp  Ile  Ile
 1                    5                    10                         15

Ile  Cys  Asp  Glu  Cys  His  Ser  Thr  Asp  Ala  Thr  Ser  Ile  Leu  Gly
               20                    25                         30

Ile  Gly  Thr  Val  Leu  Asp  Gln  Ala  Glu  Thr  Ala  Gly
               35                    40
```

( 2 ) INFORMATION FOR SEQ ID NO: 77:

( i ) SEQUENCE CHARACTERISTICS:
        ( A ) LENGTH: 58 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 77:

```
Arg  Thr  Ile  Thr  Thr  Gly  Ser  Pro  Ile  Thr  Tyr  Ser  Thr  Tyr  Gly
 1                    5                    10                         15

Lys  Phe  Leu  Ala  Asp  Gly  Gly  Cys  Ser  Gly  Gly  Ala  Tyr  Asp  Ile
               20                    25                         30

Ile  Ile  Cys  Asp  Glu  Cys  His  Ser  Thr  Asp  Ala  Thr  Ser  Ile  Leu
               35                    40                         45
```

```
Gly  Ile  Gly  Thr  Val  Leu  Asp  Gln  Ala  Glu  Thr  Ala  Gly
               50                      55
```

( 2 ) INFORMATION FOR SEQ ID NO: 78:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 78:

```
Asp  Pro  Gln  Ala  Arg  Val  Ala  Ile  Lys  Ser  Leu  Thr  Glu  Arg  Leu
 1              5                        10                         15

Thr  Val  Gly  Gly  Pro  Leu  Thr  Asn  Ser  Arg  Gly  Glu  Asn  Cys  Gly
               20                        25                         30

Tyr  Arg  Arg  Cys  Arg  Ala  Ser  Arg  Ala  Ser
               35                        40
```

( 2 ) INFORMATION FOR SEQ ID NO: 79:

( i ) SEQUENCE CHARACTERISTICS:
        ( A ) LENGTH: 35 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 79:

```
Thr  Asn  Asp  Cys  Pro  Asn  Ser  Ser  Ile  Val  Tyr  Glu  Ala  His  Asp
 1              5                        10                         15

Ala  Ile  Leu  His  Thr  Pro  Gly  Cys  Val  Pro  Cys  Val  Arg  Glu  Gly
               20                        25                         30

Asn  Val  Ser  Arg  Cys
               35
```

( 2 ) INFORMATION FOR SEQ ID NO: 80:

( i ) SEQUENCE CHARACTERISTICS:
        ( A ) LENGTH: 45 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 80:

```
Val  Arg  Asn  Ser  Thr  Gly  Leu  Tyr  His  Val  Thr  Asn  Asp  Cys  Pro
 1              5                        10                         15

Asn  Ser  Ser  Ile  Val  Tyr  Glu  Ala  His  Asp  Ala  Ile  Leu  His  Thr
               20                        25                         30

Pro  Gly  Cys  Val  Pro  Cys  Val  Arg  Gly  Gly  Asn  Val  Ser  Arg  Cys
               35                        40                         45
```

( 2 ) INFORMATION FOR SEQ ID NO: 81:

( i ) SEQUENCE CHARACTERISTICS:
        ( A ) LENGTH: 35 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 81:

```
Cys  Trp  Val  Ala  Met  Thr  Pro  Thr  Val  Ala  Thr  Arg  Asp  Gly  Lys
 1              5                        10                         15

Leu  Pro  Ala  Thr  Gln  Leu  Arg  Arg  His  Ile  Asp  Leu  Leu  Val  Gly
               20                        25                         30
```

Ser Ala Thr Leu Cys
                35

(2) INFORMATION FOR SEQ ID NO: 82:

(i) SEQUENCE CHARACTERISTICS:
        (A) LENGTH: 30 amino acids
        (B) TYPE: Amino acid
        (C) STRANDEDNESS:
        (D) TOPOLOGY: Unknown (xi) SEQUENCE DESCRIPTION:SEQ ID NO: 82:

Thr Gln Gly Cys Asn Cys Ser Ile Tyr Pro Gly His Ile Thr Gly
1               5                   10                  15

His Arg Met Ala Trp Asp Met Met Asn Trp Ser Pro Thr Ala
            20                  25                  30

(2) INFORMATION FOR SEQ ID NO: 83:

(i) SEQUENCE CHARACTERISTICS:
        (A) LENGTH: 50 amino acids
        (B) TYPE: Amino acid
        (C) STRANDEDNESS:
        (D) TOPOLOGY: Unknown (xi) SEQUENCE DESCRIPTION:SEQ ID NO: 83:

Cys Gly Ser Val Phe Leu Ile Gly Gln Leu Phe Thr Phe Ser Pro
1               5                   10                  15

Arg Arg His Trp Thr Thr Gln Gly Cys Asn Cys Ser Ile Tyr Pro
            20                  25                  30

Gly His Ile Thr Gly His Arg Met Ala Trp Asp Met Met Met Asn
            35                  40                  45

Trp Ser Pro Thr Ala
            50

(2) INFORMATION FOR SEQ ID NO: 84:

(i) SEQUENCE CHARACTERISTICS:
        (A) LENGTH: 25 amino acids
        (B) TYPE: Amino acid
        (C) STRANDEDNESS:
        (D) TOPOLOGY: Unknown (xi) SEQUENCE DESCRIPTION:SEQ ID NO: 84:

Asp Met Ile Ala Gly Ala His Trp Gly Val Leu Ala Gly Ile Ala
1               5                   10                  15

Tyr Phe Ser Met Val Gly Asn Trp Ala Lys
            20                  25

(2) INFORMATION FOR SEQ ID NO: 85:

(i) SEQUENCE CHARACTERISTICS:
        (A) LENGTH: 35 amino acids
        (B) TYPE: Amino acid
        (C) STRANDEDNESS:
        (D) TOPOLOGY: Unknown (xi) SEQUENCE DESCRIPTION:SEQ ID NO: 85:

Gln Leu Leu Arg Ile Pro Gln Ala Ile Leu Asp Met Ile Ala Gly
1               5                   10                  15

Ala His Trp Gly Val Leu Ala Gly Ile Ala Tyr Phe Ser Met Val
            20                  25                  30

Gly Asn Trp Ala Lys
            35

( 2 ) INFORMATION FOR SEQ ID NO: 86:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 86:

```
Ala Leu Val Met Ala Gln Leu Leu Arg Ile Pro Gln Ala Ile Leu
 1               5                  10                  15
Asp Met Ile Ala Gly Ala His Trp Gly Val Leu Ala Gly Ile Ala
                20                  25                  30
Tyr Phe Ser Met Val Gly Asn Trp Ala Lys
                35                  40
```

( 2 ) INFORMATION FOR SEQ ID NO: 87:

( i ) SEQUENCE CHARACTERISTICS:
        ( A ) LENGTH: 25 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 87:

```
Gln Ala Ala Arg Ala Met Ser Gly Leu Val Ser Leu Phe Thr Pro
 1               5                  10                  15
Gly Ala Lys Gln Asn Ile Gln Leu Ile Asn
                20                  25
```

( 2 ) INFORMATION FOR SEQ ID NO: 88:

( i ) SEQUENCE CHARACTERISTICS:
        ( A ) LENGTH: 45 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 88:

```
Val Leu Val Val Leu Leu Leu Phe Ala Gly Val Asp Ala Glu Thr
 1               5                  10                  15
Ile Val Ser Gly Gly Gln Ala Ala Arg Ala Met Ser Gly Leu Val
                20                  25                  30
Ser Leu Phe Thr Pro Gly Ala Lys Gln Asn Ile Gln Leu Ile Asn
                35                  40                  45
```

( 2 ) INFORMATION FOR SEQ ID NO: 89:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 89:

```
Tyr Phe Ser Met Val Gly Asn Trp Ala Lys Val Leu Val Val Leu
 1               5                  10                  15
Leu Leu Phe Ala Gly Val Asp Ala Glu Thr Ile Val Ser Gly Gly
                20                  25                  30
Gln Ala Ala Arg Ala Met Ser Gly Leu Val Ser Leu Phe Thr Pro
                35                  40                  45
Gly Ala Lys Gln Asn Ile Gln Leu Ile Asn
                50                  55
```

( 2 ) INFORMATION FOR SEQ ID NO: 90:

( i ) SEQUENCE CHARACTERISTICS:
        ( A ) LENGTH: 60 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 90:

```
Leu Ala Gly Ile Ala Tyr Phe Ser Met Val Gly Asn Trp Ala Lys
 1               5                  10                  15

Val Leu Val Val Leu Leu Leu Phe Ala Gly Val Asp Ala Glu Thr
                20                  25                  30

Ile Val Ser Gly Gly Gln Ala Ala Arg Ala Met Ser Gly Leu Val
                35                  40                  45

Ser Leu Phe Thr Pro Gly Ala Lys Gln Asn Ile Gln Leu Ile Asn
                50                  55                  60
```

( 2 ) INFORMATION FOR SEQ ID NO: 91:

( i ) SEQUENCE CHARACTERISTICS:
        ( A ) LENGTH: 25 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 91:

```
Thr Gly Trp Leu Ala Gly Leu Ile Tyr Gln His Lys Phe Asn Ser
 1               5                  10                  15

Ser Gly Cys Pro Glu Arg Leu Ala Ser Cys
                20                  25
```

( 2 ) INFORMATION FOR SEQ ID NO: 92:

( i ) SEQUENCE CHARACTERISTICS:
        ( A ) LENGTH: 31 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 92:

```
Cys Asn Glu Ser Leu Asn Thr Gly Trp Leu Ala Gly Leu Ile Tyr
 1               5                  10                  15

Gln His Lys Phe Asn Ser Ser Gly Cys Pro Glu Arg Leu Ala Ser
                20                  25                  30

Cys
```

( 2 ) INFORMATION FOR SEQ ID NO: 93:

( i ) SEQUENCE CHARACTERISTICS:
        ( A ) LENGTH: 38 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 93:

```
Ile Asn Ser Thr Ala Leu Asn Cys Asn Glu Ser Leu Asn Thr Gly
 1               5                  10                  15

Trp Leu Ala Gly Leu Ile Tyr Gln His Lys Phe Asn Ser Ser Gly
                20                  25                  30

Cys Pro Glu Arg Leu Ala Ser Cys
                35
```

(2) INFORMATION FOR SEQ ID NO: 94:

(i) SEQUENCE CHARACTERISTICS:
        (A) LENGTH: 52 amino acids
        (B) TYPE: Amino acid
        (C) STRANDEDNESS:
        (D) TOPOLOGY: Unknown (xi) SEQUENCE DESCRIPTION:SEQ ID NO: 94:

```
Lys Gln Asn Ile Gln Leu Ile Asn Thr Asn Gly Ser Trp His Ile
 1               5                  10                  15

Asn Ser Thr Ala Leu Asn Cys Asn Glu Ser Leu Asn Thr Gly Trp
                20                  25                  30

Leu Ala Gly Leu Ile Tyr Gln His Lys Phe Asn Ser Ser Gly Cys
                35                  40                  45

Pro Glu Arg Leu Ala Ser Cys
                50
```

(2) INFORMATION FOR SEQ ID NO: 95:

(i) SEQUENCE CHARACTERISTICS:
        (A) LENGTH: 38 amino acids
        (B) TYPE: Amino acid
        (C) STRANDEDNESS:
        (D) TOPOLOGY: Unknown (xi) SEQUENCE DESCRIPTION:SEQ ID NO: 95:

```
Ser Glu Cys Thr Thr Pro Cys Ser Gly Ser Trp Leu Arg Asp Ile
 1               5                  10                  15

Trp Asp Trp Ile Cys Glu Val Leu Ser Asp Phe Lys Thr Trp Leu
                20                  25                  30

Lys Ala Lys Leu Met Pro Gln Leu
                35
```

(2) INFORMATION FOR SEQ ID NO: 96:

(i) SEQUENCE CHARACTERISTICS:
        (A) LENGTH: 47 amino acids
        (B) TYPE: Amino acid
        (C) STRANDEDNESS:
        (D) TOPOLOGY: Unknown (xi) SEQUENCE DESCRIPTION:SEQ ID NO: 96:

```
Leu Arg Arg Leu His Gln Trp Ile Ser Ser Glu Cys Thr Thr Pro
 1               5                  10                  15

Cys Ser Gly Ser Trp Leu Arg Asp Ile Trp Asp Trp Ile Cys Glu
                20                  25                  30

Val Leu Ser Asp Phe Lys Thr Trp Leu Lys Ala Lys Leu Met Pro
                35                  40                  45

Gln Leu
```

(2) INFORMATION FOR SEQ ID NO: 97:

(i) SEQUENCE CHARACTERISTICS:
        (A) LENGTH: 22 amino acids
        (B) TYPE: Amino acid
        (C) STRANDEDNESS:
        (D) TOPOLOGY: Unknown (xi) SEQUENCE DESCRIPTION:SEQ ID NO: 97:

```
Asp Phe His Tyr Val Thr Gly Met Thr Thr Asp Asn Leu Lys Cys
 1               5                  10                  15

Pro Cys Gln Val Pro Ser Pro
                20
```

( 2 ) INFORMATION FOR SEQ ID NO: 98:

( i ) SEQUENCE CHARACTERISTICS:
      ( A ) LENGTH: 38 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 98:

```
Leu Trp Arg Val Ser Ala Glu Glu Tyr Val Glu Ile Arg Gln Val
  1               5                  10                  15

Gly Asp Phe His Tyr Val Thr Gly Met Thr Thr Asp Asn Leu Lys
                 20                  25                  30

Cys Pro Cys Gln Val Pro Ser Pro
                 35
```

( 2 ) INFORMATION FOR SEQ ID NO: 99:

( i ) SEQUENCE CHARACTERISTICS:
      ( A ) LENGTH: 42 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 99:

```
Asp Gly Val Arg Leu His Arg Phe Ala Pro Pro Cys Lys Pro Leu
  1               5                  10                  15

Leu Arg Glu Glu Val Ser Phe Arg Val Gly Leu His Glu Tyr Pro
                 20                  25                  30

Val Gly Ser Gln Leu Pro Cys Glu Pro Glu Pro Asp
                 35                  40
```

( 2 ) INFORMATION FOR SEQ ID NO: 100:

( i ) SEQUENCE CHARACTERISTICS:
      ( A ) LENGTH: 54 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 100:

```
Cys Gln Val Pro Ser Pro Glu Phe Phe Thr Glu Leu Asp Gly Val
  1               5                  10                  15

Arg Leu His Arg Phe Ala Pro Pro Cys Lys Pro Leu Leu Arg Glu
                 20                  25                  30

Glu Val Ser Phe Arg Val Gly Leu His Glu Tyr Pro Val Gly Ser
                 35                  40                  45

Gln Leu Pro Cys Glu Pro Glu Pro Asp
                 50
```

( 2 ) INFORMATION FOR SEQ ID NO: 101:

( i ) SEQUENCE CHARACTERISTICS:
      ( A ) LENGTH: 23 amino acids
      ( B ) TYPE: Amino acid
      ( C ) STRANDEDNESS:
      ( D ) TOPOLOGY: Unknown ( x i ) SEQUENCE DESCRIPTION:SEQ ID NO: 101:

```
Ser Ser Ser Ala Ser Gln Leu Ser Ala Pro Ser Leu Lys Ala Thr
  1               5                  10                  15

Cys Thr Ala Asn His Asp Ser Pro
                 20
```

( 2 ) INFORMATION FOR SEQ ID NO: 102:

( i ) SEQUENCE CHARACTERISTICS:
        ( A ) LENGTH: 35 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 102:

```
Arg Arg Leu Ala Arg Gly Ser Pro Pro Ser Val Ala Ser Ser Ser
 1               5                  10                  15
Ala Ser Gln Leu Ser Ala Pro Ser Leu Lys Ala Thr Cys Thr Ala
                20                  25                  30
Asn His Asp Ser Pro
                35
```

( 2 ) INFORMATION FOR SEQ ID NO: 103:

( i ) SEQUENCE CHARACTERISTICS:
        ( A ) LENGTH: 35 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 103:

```
Leu Trp Arg Gln Glu Met Gly Gly Asn Ile Thr Arg Val Glu Ser
 1               5                  10                  15
Glu Asn Lys Val Val Ile Leu Asp Ser Phe Asp Pro Leu Val Ala
                20                  25                  30
Glu Glu Asp Glu Arg
                35
```

( 2 ) INFORMATION FOR SEQ ID NO: 104:

( i ) SEQUENCE CHARACTERISTICS:
        ( A ) LENGTH: 50 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 104:

```
Ala Asn His Asp Ser Pro Asp Ala Glu Leu Ile Glu Ala Asn Leu
 1               5                  10                  15
Leu Trp Arg Gln Glu Met Gly Gly Asn Ile Thr Arg Val Glu Ser
                20                  25                  30
Glu Asn Lys Val Val Ile Leu Asp Ser Phe Asp Pro Leu Val Ala
                35                  40                  45
Glu Glu Asp Glu Arg
                50
```

( 2 ) INFORMATION FOR SEQ ID NO: 105:

( i ) SEQUENCE CHARACTERISTICS:
        ( A ) LENGTH: 26 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 105:

```
Ser Phe Asp Pro Leu Val Ala Glu Glu Asp Glu Arg Glu Ile Ser
 1               5                  10                  15
Val Pro Ala Glu Ile Leu Arg Lys Ser Arg Arg
                20                  25
```

( 2 ) INFORMATION FOR SEQ ID NO: 106:

( i ) SEQUENCE CHARACTERISTICS:
    ( A ) LENGTH: 35 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 106:

Ser Glu Asn Lys Val Val Ile Leu Asp Ser Phe Asp Pro Leu Val
 1               5                  10                  15

Ala Glu Glu Asp Glu Arg Glu Ile Ser Val Pro Ala Glu Ile Leu
                20                  25                  30

Arg Lys Ser Arg Arg
                35

( 2 ) INFORMATION FOR SEQ ID NO: 107:

( i ) SEQUENCE CHARACTERISTICS:
    ( A ) LENGTH: 27 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 107:

Tyr Glu Pro Pro Val Val His Gly Cys Pro Leu Pro Pro Pro Lys
 1               5                  10                  15

Ser Pro Pro Val Pro Pro Pro Arg Lys Lys Arg Thr
                20                  25

( 2 ) INFORMATION FOR SEQ ID NO: 108:

( i ) SEQUENCE CHARACTERISTICS:
    ( A ) LENGTH: 35 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 108:

Val Glu Thr Trp Lys Lys Pro Asp Tyr Glu Pro Pro Val Val His
 1               5                  10                  15

Gly Cys Pro Leu Pro Pro Pro Lys Ser Pro Val Pro Pro Pro
                20                  25                  30

Arg Lys Lys Arg Thr
                35

( 2 ) INFORMATION FOR SEQ ID NO: 109:

( i ) SEQUENCE CHARACTERISTICS:
    ( A ) LENGTH: 44 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 109:

Ala Arg Pro Asp Tyr Asn Pro Pro Leu Val Glu Thr Trp Lys Lys
 1               5                  10                  15

Pro Asp Tyr Glu Pro Pro Val Val His Gly Cys Pro Leu Pro Pro
                20                  25                  30

Pro Lys Ser Pro Pro Val Pro Pro Pro Arg Lys Lys Arg Thr
                35                          40

( 2 ) INFORMATION FOR SEQ ID NO: 110:

( i ) SEQUENCE CHARACTERISTICS:
    ( A ) LENGTH: 72 amino acids
    ( B ) TYPE: Amino acid
    ( C ) STRANDEDNESS:
    ( D ) TOPOLOGY: Unknown ( x i ) SEQUENCE DESCRIPTION:SEQ ID NO: 110:

```
Ala Glu Glu Asp Glu Arg Glu Ile Ser Val Pro Ala Glu Ile Leu
 1               5                  10                  15

Arg Lys Ser Arg Arg Phe Ala Gln Ala Leu Pro Val Trp Ala Arg
                20                  25                  30

Pro Asp Tyr Asn Pro Pro Leu Val Glu Thr Trp Lys Lys Pro Asp
                35                  40                  45

Tyr Glu Pro Pro Val Val His Gly Cys Pro Leu Pro Pro Pro Lys
                50                  55                  60

Ser Pro Pro Val Pro Pro Arg Lys Lys Arg Thr
                65                  70
```

( 2 ) INFORMATION FOR SEQ ID NO: 111:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 111:

```
Cys Leu Thr Val Pro Ala Ser Ala Tyr Gln Val Arg Asn Ser Thr
 1               5                  10                  15

Gly Leu Tyr His Val Thr Asn Asp Cys Pro Asn Ser Ser Ile Val
                20                  25                  30

Tyr Glu Ala Ala Asp Ala Ile Leu His Thr Pro Gly Cys Val Pro
                35                  40                  45

Cys Val Arg Glu Gly Asn Ala Ser Arg Cys
                50                  55
```

( 2 ) INFORMATION FOR SEQ ID NO: 112:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 112:

```
Cys Leu Thr Val Pro Ala Ser Ala Tyr Gln Val Arg Asn Ser Ser
 1               5                  10                  15

Gly Leu Tyr His Val Thr Asn Asp Cys Pro Asn Ser Ser Ile Val
                20                  25                  30

Tyr Glu Ala Ala Asp Ala Ile Leu His Thr Pro Gly Cys Val Pro
                35                  40                  45

Cys Val Arg Glu Gly Asn Ala Ser Arg Cys
                50                  55
```

( 2 ) INFORMATION FOR SEQ ID NO: 113:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 113:

```
Cys Leu Thr Ile Pro Ala Ser Ala Tyr Glu Val Arg Asn Val Ser
 1               5                   10                  15

Gly Ile Tyr His Val Thr Asn Asp Cys Ser Asn Ser Ser Ile Val
               20                   25                  30

Tyr Glu Ala Ala Asp Met Ile Met His Thr Pro Gly Cys Val Pro
               35                   40                  45

Cys Val Arg Glu Asp Asn Ser Ser Arg Cys
               50                   55
```

( 2 ) INFORMATION FOR SEQ ID NO: 114:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 114:

```
Cys Leu Thr Ile Pro Ala Ser Ala Tyr Glu Val Arg Asn Val Ser
 1               5                   10                  15

Gly Ile Tyr His Val Thr Asn Asp Cys Ser Asn Ser Ser Ile Val
               20                   25                  30

Tyr Glu Ala Ala Asp Val Ile Met His Ala Pro Gly Cys Val Pro
               35                   40                  45

Cys Val Arg Glu Asn Asn Ser Ser Arg Cys
               50                   55
```

( 2 ) INFORMATION FOR SEQ ID NO: 115:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 115:

```
Cys Leu Thr Ile Pro Ala Ser Ala Tyr Glu Val Arg Asn Val Ser
 1               5                   10                  15

Gly Ile Tyr His Val Thr Asn Asp Cys Ser Asn Ser Ser Ile Val
               20                   25                  30

Tyr Glu Ala Ala Asp Met Ile Met His Thr Pro Gly Cys Val Pro
               35                   40                  45

Cys Val Arg Glu Ser Asn Phe Ser Arg Cys
               50                   55
```

( 2 ) INFORMATION FOR SEQ ID NO: 116:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 116:

```
Cys Leu Thr Thr Pro Ala Ser Ala Tyr Glu Val His Asn Val Ser
 1               5                   10                  15

Gly Ile Tyr His Val Thr Asn Asp Cys Ser Asn Ala Ser Ile Val
               20                   25                  30

Tyr Glu Ala Ala Asp Leu Ile Met His Thr Pro Gly Cys Val Pro
               35                   40                  45

Cys Val Arg Glu Gly Asn Ser Ser Arg Cys
```

( 2 ) INFORMATION FOR SEQ ID NO: 117:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 117:

```
Cys Ile Thr Thr Pro Val Ser Ala Ala Glu Val Lys Asn Ile Ser
1               5                   10                  15

Thr Gly Tyr Met Val Thr Asn Asp Cys Thr Asn Asp Ser Ile Thr
                20                  25                  30

Trp Gln Leu Gln Ala Ala Val Leu His Val Pro Gly Cys Val Pro
                35                  40                  45

Cys Glu Lys Val Gly Asn Thr Ser Arg Cys
                50                  55
```

( 2 ) INFORMATION FOR SEQ ID NO: 118:

( i ) SEQUENCE CHARACTERISTICS:
        ( A ) LENGTH: 55 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 118:

```
Cys Val Thr Val Pro Val Ser Ala Val Glu Val Arg Asn Ile Ser
1               5                   10                  15

Ser Ser Tyr Tyr Ala Thr Asn Asp Cys Ser Asn Asn Ser Ile Thr
                20                  25                  30

Trp Gln Leu Thr Asn Ala Val Leu His Leu Pro Gly Cys Val Pro
                35                  40                  45

Cys Glu Asn Asp Asn Gly Thr Leu Arg Cys
                50                  55
```

( 2 ) INFORMATION FOR SEQ ID NO: 119:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 119:

```
Phe Thr Phe Ser Pro Arg Arg His Trp Thr Thr Gln Gly Cys Asn
1               5                   10                  15

Cys Ser Ile Tyr Pro Gly His Ile Thr Gly His Arg Met Ala Trp
                20                  25                  30

Asp Met Met Met Asn Trp Ser Pro Thr Thr
                35                  40
```

( 2 ) INFORMATION FOR SEQ ID NO: 120:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 120:

```
Phe Thr Phe Ser Pro Arg Arg His Trp Thr Thr Gln Asp Cys Asn
```

```
                   1                   5                  10                  15
Cys  Ser  Ile  Tyr  Pro  Gly  His  Ile  Thr  Gly  His  Arg  Met  Ala  Trp
                        20                  25                          30

Asp  Met  Met  Met  Asn  Trp  Ser  Pro  Thr  Ala
                        35                  40
```

( 2 ) INFORMATION FOR SEQ ID NO: 121:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 121:

```
Phe  Thr  Phe  Ser  Pro  Arg  Arg  His  Glu  Thr  Val  Gln  Asp  Cys  Asn
 1                   5                  10                              15

Cys  Ser  Ile  Tyr  Pro  Gly  His  Leu  Ser  Gly  His  Arg  Met  Ala  Trp
                        20                  25                          30

Asp  Met  Met  Met  Asn  Trp  Ser  Pro  Thr  Thr
                        35                  40
```

( 2 ) INFORMATION FOR SEQ ID NO: 122:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 122:

```
Phe  Thr  Phe  Ser  Pro  Arg  Arg  His  Glu  Thr  Val  Gln  Asp  Cys  Asn
 1                   5                  10                              15

Cys  Ser  Ile  Tyr  Pro  Gly  His  Ile  Thr  Gly  His  Arg  Met  Ala  Trp
                        20                  25                          30

Asp  Met  Val  Ser  Asn  Trp  Ser  Pro  Thr  Ala
                        35                  40
```

( 2 ) INFORMATION FOR SEQ ID NO: 123:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 123:

```
Phe  Thr  Phe  Ser  Pro  Arg  Arg  His  Tyr  Glu  Thr  Val  Gly  Asp  Asn
 1                   5                  10                              15

Cys  Ser  Ile  Tyr  Pro  Gly  His  Ile  Thr  Gly  His  Arg  Met  Ala  Trp
                        20                  25                          30

Asp  Met  Val  Ser  Asn  Trp  Ser  Pro  Thr  Thr
                        35                  40
```

( 2 ) INFORMATION FOR SEQ ID NO: 124:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 124:

```
Phe  Thr  Phe  Ser  Pro  Arg  Arg  His  Val  Thr  Leu  Gln  Asp  Cys  Asn
```

```
                1               5                          10                          15
Cys    Ser    Ile    Tyr    Pro    Gly    His    Ile    Thr    Gly    His    Arg    Met    Ala    Trp
                              20                          25                          30

Asp    Met    Val    Ser    Asn    Trp    Ser    Pro    Thr    Thr
                              35                          40
```

( 2 ) INFORMATION FOR SEQ ID NO: 125:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 125:

```
Phe    Ile    Val    Ser    Pro    Gln    His    His    Trp    Phe    Val    Gln    Asp    Cys    Asn
 1                             5                          10                          15

Cys    Ser    Ile    Tyr    Pro    Gly    Thr    Ile    Thr    Gly    His    Arg    Met    Ala    Trp
                              20                          25                          30

Asp    Met    Met    Met    Asn    Trp    Ser    Pro    Thr    Ala
                              35                          40
```

( 2 ) INFORMATION FOR SEQ ID NO: 126:

( i ) SEQUENCE CHARACTERISTICS:
        ( A ) LENGTH: 40 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 126:

```
Phe    Ile    Ile    Ser    Pro    Glu    Arg    His    Asn    Phe    Thr    Gln    Glu    Cys    Asn
 1                             5                          10                          15

Cys    Ser    Ile    Tyr    Gln    Gly    His    Ile    Thr    Gly    His    Arg    Met    Ala    Trp
                              20                          25                          30

Asp    Met    Met    Leu    Asn    Trp    Ser    Pro    Thr    Leu
                              35                          40
```

( 2 ) INFORMATION FOR SEQ ID NO: 127:

( i ) SEQUENCE CHARACTERISTICS:
        ( A ) LENGTH: 35 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 127:

```
Val    Asp    Gly    His    Thr    His    Val    Thr    Gly    Gly    Arg    Val    Ala    Ser    Ser
 1                             5                          10                          15

Thr    Gln    Ser    Leu    Val    Ser    Trp    Leu    Ser    Gln    Gly    Pro    Ser    Gln    Lys
                              20                          25                          30

Ile    Gln    Leu    Val    Asn
                              35
```

( 2 ) INFORMATION FOR SEQ ID NO: 128:

( i ) SEQUENCE CHARACTERISTICS:
        ( A ) LENGTH: 35 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 128:

```
Val    Asp    Gly    Asp    Thr    His    Val    Thr    Gly    Gly    Ala    Gln    Ala    Lys    Thr
```

```
               1               5                   10                  15
Thr  Asn  Arg  Leu  Val  Ser  Met  Phe  Ala  Ser  Gly  Pro  Ser  Gln  Lys
                    20                  25                  30

Ile  Gln  Leu  Ile  Asn
                    35
```

(2) INFORMATION FOR SEQ ID NO: 129:

(i) SEQUENCE CHARACTERISTICS:
        (A) LENGTH: 44 amino acids
        (B) TYPE: Amino acid
        (C) STRANDEDNESS:
        (D) TOPOLOGY: Unknown (xi) SEQUENCE DESCRIPTION:SEQ ID NO: 129:

```
Cys  Val  Arg  Glu  Gly  Asn  Ala  Ser  Arg  Cys  Trp  Val  Ala  Met  Thr
 1                   5                       10                       15

Pro  Thr  Val  Ala  Thr  Arg  Asp  Gly  Lys  Leu  Pro  Ala  Thr  Gln  Leu
                    20                       25                       30

Arg  Arg  His  Ile  Asp  Leu  Leu  Val  Gly  Ser  Ala  Thr  Leu  Cys
                    35                       40
```

(2) INFORMATION FOR SEQ ID NO: 130:

(i) SEQUENCE CHARACTERISTICS:
        (A) LENGTH: 44 amino acids
        (B) TYPE: Amino acid
        (C) STRANDEDNESS:
        (D) TOPOLOGY: Unknown (xi) SEQUENCE DESCRIPTION:SEQ ID NO: 130:

```
Cys  Val  Arg  Glu  Gly  Asn  Ala  Ser  Arg  Cys  Trp  Val  Ala  Val  Thr
 1                   5                       10                       15

Pro  Thr  Val  Ala  Thr  Arg  Asp  Gly  Lys  Leu  Pro  Thr  Thr  Gln  Leu
                    20                       25                       30

Arg  Arg  His  Ile  Asp  Leu  Leu  Val  Gly  Ser  Ala  Thr  Leu  Cys
                    35                       40
```

(2) INFORMATION FOR SEQ ID NO: 131:

(i) SEQUENCE CHARACTERISTICS:
        (A) LENGTH: 44 amino acids
        (B) TYPE: Amino acid
        (C) STRANDEDNESS:
        (D) TOPOLOGY: Unknown (xi) SEQUENCE DESCRIPTION:SEQ ID NO: 131:

```
Cys  Val  Arg  Glu  Asp  Asn  Ser  Ser  Arg  Cys  Trp  Val  Ala  Leu  Thr
 1                   5                       10                       15

Pro  Thr  Leu  Ala  Ala  Arg  Asn  Ala  Ser  Val  Pro  Thr  Thr  Thr  Ile
                    20                       25                       30

Arg  Arg  His  Val  Asp  Leu  Leu  Val  Gly  Ala  Ala  Ala  Phe  Cys
                    35                       40
```

(2) INFORMATION FOR SEQ ID NO: 132:

(i) SEQUENCE CHARACTERISTICS:
        (A) LENGTH: 44 amino acids
        (B) TYPE: Amino acid
        (C) STRANDEDNESS:
        (D) TOPOLOGY: Unknown (xi) SEQUENCE DESCRIPTION:SEQ ID NO: 132:

```
Cys  Val  Arg  Glu  Asn  Asn  Ser  Ser  Arg  Cys  Trp  Val  Ala  Leu  Thr
```

```
               1               5                    10                   15

Pro  Thr  Leu  Ala  Ala  Arg  Asn  Ala  Ser  Val  Pro  Thr  Thr  Thr  Leu
                         20                   25                        30

Arg  Arg  His  Val  Asp  Leu  Leu  Val  Gly  Thr  Ala  Ala  Phe  Cys
                    35                        40
```

( 2 ) INFORMATION FOR SEQ ID NO: 133:

( i ) SEQUENCE CHARACTERISTICS:
        ( A ) LENGTH: 44 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 133:

```
Cys  Val  Arg  Glu  Ser  Asn  Phe  Ser  Arg  Cys  Trp  Val  Ala  Leu  Thr
 1                    5                        10                       15

Pro  Thr  Leu  Ala  Ala  Arg  Asn  Ser  Ser  Ile  Pro  Thr  Thr  Thr  Ile
                         20                   25                        30

Arg  Arg  His  Val  Asp  Leu  Leu  Val  Gly  Ala  Ala  Ala  Leu  Cys
                    35                        40
```

( 2 ) INFORMATION FOR SEQ ID NO: 134:

( i ) SEQUENCE CHARACTERISTICS:
        ( A ) LENGTH: 44 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 134:

```
Cys  Val  Arg  Glu  Gly  Asn  Ser  Ser  Arg  Cys  Trp  Val  Ala  Leu  Thr
 1                    5                        10                       15

Pro  Thr  Leu  Ala  Ala  Arg  Asn  Val  Thr  Ile  Pro  Thr  Thr  Thr  Ile
                         20                   25                        30

Arg  Arg  His  Val  Asp  Leu  Leu  Val  Gly  Ala  Ala  Ala  Phe  Cys
                    35                        40
```

( 2 ) INFORMATION FOR SEQ ID NO: 135:

( i ) SEQUENCE CHARACTERISTICS:
        ( A ) LENGTH: 44 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 135:

```
Cys  Glu  Lys  Val  Gly  Asn  Thr  Ser  Arg  Cys  Trp  Ile  Pro  Val  Ser
 1                    5                        10                       15

Pro  Asn  Val  Ala  Val  Gln  Gln  Pro  Gly  Ala  Leu  Thr  Gln  Gly  Leu
                         20                   25                        30

Arg  Thr  His  Ile  Asp  Met  Val  Val  Met  Ser  Ala  Thr  Leu  Cys
                    35                        40
```

( 2 ) INFORMATION FOR SEQ ID NO: 136:

( i ) SEQUENCE CHARACTERISTICS:
        ( A ) LENGTH: 44 amino acids
        ( B ) TYPE: Amino acid
        ( C ) STRANDEDNESS:
        ( D ) TOPOLOGY: Unknown ( x i ) SEQUENCE DESCRIPTION:SEQ ID NO: 136:

```
Cys  Glu  Asn  Asp  Asn  Gly  Thr  Leu  Arg  Cys  Trp  Ile  Gln  Val  Thr
```

```
  1                   5                        1 0                              1 5
Pro Asn Val Ala Val Lys His Arg Gly Ala Leu Thr His Asn Leu
                     2 0                      2 5                              3 0

Arg Thr His Val Asp Met Ile Val Met Ala Ala Thr Val Cys
                 3 5                 4 0
```

SYNTHETIC PEPTIDES SPECIFIC FOR THE DETECTION OF ANTIBODIES TO HCV, DIAGNOSIS OF HCV INFECTION AND PREVENTIONS THEREOF AS VACCINES

CROSS-REFERENCE TO RELATED APPLICATION

This is a continuation of application Ser. No. 07/719,819, filed on Jun. 24, 1991, abandoned, which is a continuation-in-part application of application Ser. No. 667,275 filed Mar. 11, 1991, abandoned which in turn is a continuation-in-part application of Ser. No. 651,735 filed Feb. 7, 1991, abandoned, which in turn is a continuation-in-part application of Ser. No. 558,799, filed Jul. 26, 1990, now U.s. Pat. No. 5,106,726, which in turn is a continuation-in-part application of Ser. No. 510,153, filed Apr. 16, 1990, now abandoned, and which in turn is a continuation-in-part application of application Ser. No. 481,348, filed Feb. 16, 1990, now abandoned.

INTRODUCTION

The present invention relates to peptides specific for the diagnosis and prevention of hepatitis C virus (HCV) infection, or non-A non-B hepatitis (NANBH). More particularly, the present invention is directed to synthetic peptides which are specific for the detection of antibodies to HCV in body fluids and immunoassays using the same. The invention also includes the use of the synthetic peptides in compositions as antigens for eliciting the production of monoclonal and polyclonal antibodies against HCV and as immunogens in vaccines for the prevention of NANBH or HCV infection.

In recent years, non-A, non-B hepatitis (NANBH) has become the most common form of post-transfusion hepatitis. Studies involving the experimental inoculation of chimpanzees provided evidence that the infectious agent was a lipid-containing virus resembling members of the Togaviridae family.

Recently, this etiological agent, termed hepatitis C virus (HCV) has been shown to be an RNA virus with a genome size of ~10 kilobases encoding a single polyprotein which can be further processed into several structural and non-structural proteins (1–4). Additional computer-assisted protein analysis demonstrates that HCV shares sequence similarity with the polyproteins of animal pestiviruses and flaviviruses as well as members of two plant virus supergroups (5).

More recently, a number of reports have led to an increasingly coherent understanding of the function of various regions of the virus and of the relationships among genomic fragments isolated from variants or closely related viruses.

A summary of the HCV structure, beginning at the N terminus of the virus, follows. The HCV comprises a structural protein region and nonstructural (NS) protein regions. The structural protein region is further divided into capsid and envelop proteins. The NS protein regions are further divided into NS-1 to NS-5 regions (3).

The postulated capsid region (AA1-AA120) has been shown to contain highly immunoreactive conserved epitopes with enhanced sensitivity in the detection of hepatitis C infection (6–8). The region appears to consist of two segments of equal length (AA1-61, AA62-AA120), which are homologous to one another, perhaps as a result of a gene duplication, and are also homologous to the N terminal core region of yellow fever virus (9), also a flavivirus (Table 1A). Both halves, as represented by peptides VIIIE (AA2-AA62) and IXD (AA65-AA119), disclosed in application Ser. No. 558,799, have been shown to be immunoreactive. A genomic fragment of a NANBH virus cloned by Arima et al. (10), designated clone 2, contains a Gly-Pro-Arg-Leu-Gly sequence identical to residues 39–43 in peptide VIIIE (Table 1B), placing this clone 2 fragment in the putative core region of a related virus. Two other sequences from NANBH viruses, cloned by Reyes et al. (11) and by Arima et al. (clone 1) (12), show sequence similarities with the capsid region of yellow fever virus (Table 1C). Thus, there appears to be a number of related viruses, all of which have highly immunogenic capsid regions, as evidenced by the ease of cloning. Variants of hepatitis C (J, J-1, J-4) are also highly conserved in this region (2–4), so the other clones mentioned by Arima et al. may be from different viruses, rather than from variants of HCV.

Mishiro and colleagues have isolated a cDNA clone from the plasma of a chimpanzee infected with NANBHV which codes for a host cellular sequence bearing an epitope which is reactive with sera from individuals who are PCR positive for HCV (13). The sequence of the immunoreactive peptide (GOR epitope) is not encoded by HCV and was reported not to resemble a published sequence of HCV spanning three-quarters of the genome (1) or the 5'-terminal sequence of HCV (2) covering the upstream quarter of the genome. However, inspection of the GOR epitope sequence revealed 47% homology with an N-terminal fragment covered by peptide VIIIE described in UBI Applications Ser. No. 558, 799. Lesser degrees of homology were obtained from comparison with the N-terminus of the yellow fever virus capsid protein (33%) (9) and the protein segment corresponding to clone 1 of Arima et al.(37.5%) (12) (See Table 1D).

The presence of antibodies which are cross-reactive with the GOR epitope sequence in HCV infected individuals may be explained by structural similarity of the GOR epitope with the corresponding region of the HCV capsid protein. Compared with anti-C100, antibodies to the C100 region, previously identified by Houghton et al.; antibodies to peptide VIIIE share the following characteristics with anti-GOR: they both are present in some but not all anti-C100 positive sera; they can be detected in anti-C100 negative sera from both acute and chronic NANBH patients; they appear earlier than anti-C100 in the seroconversion series; they are detected in more seroconversion panels than anti-C100 (13); and they are present in 1–2% of normal controls and 15–20% of HBsAg positive individuals. Early NANBH assays reported to react with host-determinant cytoplasmic antigens may in fact have detected anti-HCV capsid protein cross-reactivity.

The postulated envelope (env) region consists of amino acids 120 to 400. The env glycoproteins of flaviviruses are key targets for immunization because the env region is a major antigen of free viral particles and plays a central role in flavivirus biology. The env region mediates binding to cell receptors and probably facilitates fusion to membranes. It also induces protective immune responses after vaccination or natural infection with a flavivirus (14,15) and stimulates cell-mediated immunity (16). The type-specific epitopes on env are the ones most closely associated with protective immune responses to flaviviruses (17–19). There are a number of hypervariable regions in the HCV env region, based on a comparison of US and Japanese strains (2), which may indicate epitopes for strain specific reactivity.

The non-structural protein NS-1, in addition to the small M protein of the envelope, has been shown to contribute to protective immunity in dengue fever (20,21). Inspection of sequences and hydrophobicity profiles shows that the HCV NS-1 region contains two similar domains (Table 1E). A dominant motif in this region is cysteine pairs separated by five or more amino acids.

The NS-2 region is of unknown function and little has been reported on its characteristics.

By analogy with yellow fever virus, the HCV NS-3 region may contain protease activity required for viral replication (22). A trypsin-like serine protease active site has been localized in yellow fever virus by means of site-directed mutagenesis of NS-3 to a catalytic triad consisting of His-53, Asp-77 and Ser-138. The corresponding region in HCV is the N-terminal third of NS-3, with the critical residues being His-1103, Asp-1127 and Ser-1188. The remainder of the HCV NS-3 region consists of a region which shows immunoreactivity. This region appears to consist of three subregions homologous to one another (Table 1F) and these subregions bear a distant relationship to the repeated segments of the NS-1 region.

The most widely studied region to date is the NS-4 nonstructural region. Although its function is unknown, it contains highly immunoreactive regions, primarily in the region designated as C100 by Houghton et al. (1), which became the basis for a HCV diagnostic test using recombinant technology. A high degree of structural homology is observed between part of the C100 HCV sequence with a corresponding region in the yellow fever virus (Table 1G). While this region detects antibody to the virus primarily responsible for NANBH (23), experimentally it has been shown in prior United Biomedical Inc.'s application Ser. No. 558,799 and numerous recent reports that there are shortcomings in both sensitivity and specificity in the tests relying on the C100 polypeptide as an antigen. However, synthetic peptides from the NS-4 region described in prior application Ser. No. 558,799 overcome the problem of non-specific reactivity.

The nonstructural region proximal to the C terminus of HCV is NS-5, the site of polymerase (pol) activity. The Gly-Asp-Asp sequence in this region is conserved across many viruses(11). Maeno et al. have isolated a clone corresponding to a sequence upstream of the pol site in the NS-5 region which is immunoreactive and which reacts specifically with sera from patients in the chronic phase of NANBH(24).

Through an extensive series of experiments involving serological validation using select specimens chosen from the screening of thousands of sera with hundreds of carefully designed synthetic peptides, we have further characterized the capsid protein related immunoreactive peptides and have identified additional immunoreactive epitopes contained within the envelope, NS-1, NS-2, NS-3, and NS-5 protein regions.

Synthetic peptides have been increasingly used to map antigenic or immunogenic sites on the surface of proteins, an approach recently termed "site-directed-serology". We, at United Biomedical, have taken this approach to identify and characterize highly antigenic epitopes on the envelope and core proteins of HIV and to develop sensitive and specific immunoassays for the detection of antibodies to HIV (previously designated HTLV-III) (25–27). See U.S. Pat. No. 4,735,896, issued Apr. 5, 1988 and U.S. Pat. No. 4,879,212 issued Nov. 7, 1989, the contents of which are, hereby, fully incorporated by reference (28,29). Subsequently, a series of finely mapped and well-characterized HTLV-I/II related synthetic peptides were employed in the development of synthetic peptide-based diagnostic assays for the detection of HTLV-I/II antibodies in infected individuals (30,31). See also U.S. Pat. No. 4,833,071 issued May 23, 1989, U.S. Ser. No. 07/297,635 filed Jan. 13, 1989 and U.S. Ser. No. 07/469,294 filed Jan. 24, 1990. These assays have provided superior sensitivity, excellent specificity, and, in certain cases, an unmatched capability to differentiate infections between two closely related viruses, thus overcoming many of the existing problems associated with biologically-derived tests based on either viral lysates or recombinant DNA-derived proteins.

It is, therefore, an objective of the present invention to employ the identified and characterized immunoreactive HCV peptides in the development of a detection or diagnostic procedure to identify and monitor HCV infection.

A further objective is to chemically synthesize a test reagent which can then be used to detect the presence of antibodies to HCV in body fluids and to diagnose NANBH.

Another objective is to develop a vaccine which, when introduced into healthy mammals, including humans, will stimulate production of efficacious antibodies to HCV, thereby providing protection against HCV infection.

A further objective is to provide a synthetic immunogen which can be used in mammals for the development of monoclonal and polyclonal antibodies to HCV.

TABLE 1A

```
                                                                FFF
S- GRHAQKTLGVNMVRRG- -VRSLS- NKIKQK- TKQI GNRPG- --PSR- GVQGFI LFNI LTGKKIT- AHLK- R- L
                      :                    :    :      :                  :    :
ST- PKPQRKT- KRNT NRRPQDVK FPGGGQI VGG VY- LL- PR- --RGP- RLGV- - RATRK- - TSER- SQPRGR- RQP
                                                                             :
QPI PKV RRPEGR- TWAQPGYP WPLY GNEGC GWAGWLLSPR- GSR- PSW- G- P- - - - - - - H- D- - - PRRRSRN L
```

Amino acid sequences (single letter code) derived from the corresponding N-terminal capsid protein of the Yellow Fever Virus (AA2–AA68, upper line; Ref. 9) and the Hepatitis C Virus (AA2–AA64, middle line; and AA63–AA119, lower line; Ref. 2) are aligned for comparison of homology. Identical amino acid matches are boxed with a solid line, while matches scored as similar by the PAM-250 matrix are connected with a colon. Dashes represent spaces between adjacent amino acids that have been inserted to optimize the alignment.

TABLE 1B

```
                                        EF P I R  -  R L G P -  R L G  R R P A L M A V E
S T I P K P Q R K T -  K R N T N  R R P Q D V K F P G G Q I  V G G V Y -  L L  P  R  -  R  G P -  R L G V R  -  A T R K T -
Q P I P K V -  R R P E G R -  T W A Q P G Y P W P L Y G N E G C G W A G W L L S P  R G S R  -  H S W - G  -  -  P  -  -  -  I D
```

Amino acid sequence (single letter code) derived from a segment of Arima et al.'s NANBHV protein clone 2 (upper line; Ref. 10) is aligned with segments of the N-terminal capsid protein of the Hepatitis C Virus (AA2–AA52, middle line; and AA63–AA111, lower line) for comparison of homology. Identical amino acid matches are boxed with a solid line, while matches scored as similar by the PAM-250 matrix are connected with a colon. Dashes represent spaces between adjacent amino acids that have been inserted to optimize the alignment.

TABLE 1C

```
                                                                        FFF
K A Q G K T L -  G V N M V R R G -  V -  R S L S N K I K Q K T K Q I  G N R P G P S R G -  -  M Q G H I L F N I  -  L T G K R I  T A H L K R -  -  L W -  -  -
K N N -  K I L H -  L R K S A T -  K V -  -  -  -  S -  K Y K I  K -  K L -  S V G V A -  S V L -  -  M -  G A T F F -  -  -  L -  G S T A S A S  A S D E Q L A D K Q
K K -  G E A S N G E A E  N D T H K K Q R -  -  -  -  R Y K E K E K T A T N N P G K N K K P R V -  G R I -  -  K N W N R E G R K D -  A Y Q I R -  K R -  -  R E
```

Amino acid sequence (single letter code) derived from the N-terminal capsid protein of the Yellow Fever Virus (AA5–AA69, upper line; Ref. 9), another NANBHV sequence cloned by Reyes et al. (AA1–AA55, middle line; Fig. 3, Ref. 11) and a third NANBHV sequence cloned by Arima et al (AA5–AA66, lower line; Ref. 12) are aligned for comparison of homology. Identical amino acid matches are boxed with a solid line, while matches scored as similar by the PAM-250 matrix are connected with a colon. Dashes represent spaces between adjacent amino acids that have been inserted to optimize the alignment.

TABLE 1D

```
G R R G Q -  K A K S -  N P N R -  P L      GOR Epitope Sequence (Ref.13)

I P K P Q R K T K R -  N T N R R P Q      AA4–AA19 Segment of HCV Capsid Peptide VIIIE
                                           of prior application serial no. 558,799
Q R R Y K E K E K T -  A T N N -  P G      Arima et al. Clone 1 (AA22–AA37, Ref.12)

G R K A Q G K T L G V M N V R R -  G      Yellow Fever Virus (AA3–AA19, Ref.9)
```

Amino acid sequences (single letter code) derived from the GOR Epitope (upper line; Ref.139), a segment of the HCV capsid peptide VIIIE representing HCV AA4–AA19 of prior application (second line), AA22–AA37 of the NANBHV sequence (clone 1) reported by by Arima et al (third line; Ref. 12) and a segment of the Yellow Fever Virus N-terminal capsid protein (AA2–AA19, Ref.9) are aligned for comparison of homology. Identical amino acid matches are boxed with a solid line, while matches scored as similar by the PAM-250 matrix are connected with a colon. Dashes represent spaces between adjacent amino acids that have been inserted to optimize the alignment.

TABLE 1E

```
HCV-NS1(J-1)   C R R -  L -  T D F D Q G W G P I  S Y A N G S G P D Q R P  Y C -  -  W H Y P P K P C G -  I  V -  P A -  -  K S  V C G P  V Y C

D R S G A P T -  Y -  -  S W G E N D T D V F V L N N T R P P L G N W -  F G -  -  -  C T W M N S T G F T K -  V C G A P P C
```

Amino acid sequences (single letter code) derived from two segments of the HCV NS-1 protein (upper line, AA459–AA508; and lower line, AA520–AA569; are aligned for comparison of homology. Identical amino acid matches are boxed with a solid line, while matches scored as similar by the PAM-250 matrix are connected with a colon. Dashes represent spaces between adjacent amino acids that have been inserted to optimize the alignment

```
HCV-NS-1(J-1)   C R R L T D F D Q G W G P I  S H A N G S G P D Q R P Y C W H Y P P K P  C G I  V P A K S V C G P V Y C

HCV-NS-1(J-4)   C R P I D W F A Q G W G P I  T Y T E P D S P D Q R P Y C W H Y A P R P  C G I  V P A S Q V C G P V Y C

HCV-NS-1(J)     C R P I D E F A Q G W G P I  T H D M P E S S D Q R P Y C W H Y A P R P  C G I  V P A S Q V C G P V Y C
```

Amino acid sequences (single letter code) derived from three HCV strains (J-1, J-4 and J) for a segment of the NS-1 protein (AA459–AA508); are aligned for comparison of homology.

TABLE 1E-continued

```
HCV-NS-1(PT)  DRS GAPTYSWGEN DI VDFV LN NTRPP L GNWFGCTWMNSTGFTK V CGAPPC
HCV-NS-1(J)   DRF GAPTYSWGEN EI DVLL LS NTRPP Q GNWFGCTWMNSTGFTK T CGGPPC
```

Amino acid sequences (single letter code) derived from two HCV strains (PT and J) for a segment of the NS-1 protein (AA520–AA569) are aligned for comparison of homology.

```
HCV-NS-1(PT)  DRS GAPTYSWGEN DI VDFV LN NTRPP L GNWFGCTWMNSTGFTK V CGAPPC
HCV-NS-1(J)   DRF GAPTYSWGEN EI DVLL LS NTRPP Q GNWFGCTWMNSTGFTK T CGGPPC
```

Amino acid sequences (single letter code) derived from two HCV strains (PT and J) for a segment of the NS-1 protein (AA520–AA569) are aligned for comparison of homology.

TABLE 1F

```
HCV-NS3  DF P - - ME N L TT MRS P VF TDN S S - P V - - V - PQ- S - H QVA E L HAPTGSGK S T - - K VP
         PNI RT G V RTI - TTG - SP I - TY- S TYGKF L AD- GG C S GGAYD- - I I I CDE C H S TD A T
         PNI EE - MA- LS TTG EI P - F - Y GKA- I P - LE V IKGG R HLIF C - - HS KKK CDE L - A - - AK L
```

Amino acid sequences (single letter code) derived from three segments of the HCV NS-3 protein (AA1194–1241, upper line; AA1276–AA1324, middle line; and AA1360–AA1407, lower line) are aligned for comparison of homology. Identical amino acid matches are boxed with a solid line, while matches scored as similar by the PAM-250 matrix are connected with a colon. Dashes represent spaces between adjacent amino acids that have been inserted to optimize the alignment.

```
HCV   VVL A T ATPP GS VT
BVD   VV A MTATP A GS VT
HOG   VV A MTATP A GT VT
YFV   TI L MTATPPGT S D

HCV   QRRGR T GR GKP G - YR
BVD   QRRGRVGRVKPGRYYR
HOG   QRRGRVGRVKPGRYYR
YFV   QRRGR I GR - N P N R DGD
```

Multiple alignment of two highly conserved segments encoded within the NS-3 protein region (single letter code) of HCV (AA1344–AA1356, upper Table; and AA1486–AA1500, lower Table respectively), Bovine Diarrhea Virus (BVD, AA2025–AA2037; AA2181–AA2196), Hog Cholera Virus (HOG, AA1886–AA1898; AA-2042–AA2057) and Yellow Fever Virus (YFV AA1800–AA1812; AA1944–AA1958) are aligned for comparison of homology.

TABLE 1G

```
VVI V GR VVLS GKP AI I P D RE V L YREFD E - M - - - - - - - EE C S QH- LP Y I ENG- MM L A..
AA E V L - VBLS E - - - - L P D F - - L AKKGG E AM D TI SVFLS EE GS - R- A- Y R NALS M M P..

E N  FKQK- A L - GLL Q T A S RQ A E VI   HCV-NS4
E M TI VMLFI L A GLL - I - S GM- - V I   YFV-NS4
```

Amino acid sequences (single letter code) derived from a segment of the HCV NS-4 protein and a corresponding segment of the Yellow Fever Virus NS-4 protein (lower line, AA2109–AA2176, Ref.9) are aligned for comparison of homology. Identical amino acid matches are boxed with a solid line, while matches scored as similar by the PAM-250 matrix are connected with a colon. Dashes represent spaces between adjacent amino acids that have been inserted to optimize the alignment.

REFERENCES

1. Houghton M., Choo Q-L, Kuo G.: NANBV diagnostics and vaccines. EPO 0318216A1 (1989).
2. Okamoto H., Okada S., Sugiyama S., Yotsumoto S., Tanaka T., Yoshizawa H., Tsuda F., Miyakawa Y., Mayumi M.: The 5' terminal sequence of the hepatitis C virus genome. *Jpn. J. Exp. Med.* 60:167 (1990).
3. Houghton M., Choo Q-L, Kuo G.: NANBH diagnostics and vaccines. EPO 0388232A1 (1990).
4. Kato N., Hijikata M., Ootsuyama Y., et al: Molecular cloning of the human hepatitis C virus genome from Japanese patients with non-A, non-B hepatitis. *Proc. Natl. Acad. Sci. USA* 87:9524 (1990).
5. Miller R. H., Purcell R. H.: Hepatitis C virus shares amino acid sequence similarity with pestiviruses and flaviviruses as well as members of two plant virus supergroups. *Proc. Natl. Acad. Sci. USA* 87:2057 (1990).
6. Hosein B., Fang C. T., Zhang M. L., et al: Improved serodiagnosis of hepatitis C virus infection with synthetic peptide antigen from capsid protein. *Proc. Natl. Acad. Sci. USA* 88:3647 (1991).
7. UBI HCV EIA Product Insert. (1990).
8. Okamoto H., Munekata E., Tsuda F., et al: Enzyme-linked immunosorbent assay for antibodies against the capsid protein of hepatitis C virus with a synthetic oligopeptide. *Jap. J. Exp. Med.* 60:223 (1990).
9. Rice C. M., Lencheo E. M., Eddy S. R., et al: Nucleotide sequence of yellow fever virus: Implications for flavivirus gene expression and evolution. *Science* 229:726 (1985).
10. Arima T., Takamizawa A., Mori C., et al: A lambda gt11-cDNA clone specific for chronic hepatitis C generated from pooled serum presumably infected by hepatitis C virus. *Gastroenterologia Japonica* 24:545 (1989).
11. Reyes G. R., Purdy M. A., Kim J., et al: Isolation of a cDNA from the virus responsible for enterically transmitted non-A, non-B hepatitis. *Science* 247:1335 (1990).
12. Arima T., Nagashima H., Murakami S., et al: Cloning of a cDNA associated with acute and chronic hepatitis C infection generated from patients serum RNA. *Gastroenterologia Japonica* 24:540 (1989).
13. Mishiro S., Hoshi Y., Takeda K., et al: Non-A, non-B hepatitis specific antibodies directed at host-derived epitope: Implication for an autoimmune process. *Lancet* 336:1400 (1990).
14. Brinton M. A.: in *The Togaviridae and Flaviviridae*, ed. Schlesinger S. and Schlesinger M. J. Plenum Press, NY pp. 327–374 (1986).
15. Mandl C. W., Guirakhoo F., Holzmann H., Heinz F. X., Kunz C.: Antigenic structure of the flavivirus envelope protein E at the molecular level, using tick-borne encephalitis virus as a model. *J. Virol.* 63:564 (1989).
16. Bray M., Falgout B., Zhao B., et al: in *Vaccines '89, Modern Approaches to New Vaccines Including Prevention of AIDS*, ed Lerner R. A., Ginsberg H., Chanock R. M. and Brown F. Cold Spring Harbor Laboratory, NY, pp357–362 (1989).
17. Roehrig J. T., Hunt A. R., Johnson J., Mathews J. H.: ibid. pp347–350 (1989).
18. Rothman A. L., Kurane J., Ennis F. A.: ibid. pp363–366 (1989).
19. Roehrig J. T.: in *The Togaviridae and Flaviviradae*, ed Schlesinger S. and Schlesinger M. J. Plenum Press NY, pp251–278 (1986).
20. Bray M., Meu R., Lai C. J.: Meeting on Modern Approaches to New Vaccines Including Prevention of AIDS. Cold Spring Harbor Laboratory, Sep. 12–16, 1990. Abst 70.
21. Falgout B., Bray M., Schlesinger J. J, Lai C. J: Immunization of mice with recombinant vaccinia virus expressing authentic dengue virus nonstructural protein NS1 protects against lethal dengue virus encephalitis. *J. Virol.* 64:4356 (1990).
22. Chambers T. J., Weir R. C., Grakoui A., et al: Evidence that the N-terminal domain of nonstructural protein NS-3 from yellow fever virus is a serine protease responsible for site-specific cleavages in the viral polyprotein. *Proc. Natl. Acad. Sci. USA* 87:8898 (1990).
23. Kuo G., Choo Q-L, Alter H. J., et al: An assay for circulating antibodies to a major etiologic virus of human non-A, non-B hepatitis. *Science* 244:362 (1989).
24. Maeno M., Kaminaka K., Sugimoto H., et al: A cDNA clone closely associated with non-A, non-B hepatitis. *Nucleic Acids Res.* 18:2685 (1990).
25. Wang C. Y.: Synthetic-peptide-based immunodiagnosis of retrovirus infections: Current status and future prospects. In: *Synthetic Peptides in Biotechnology*, ed. Mizrahi A., Advances in Biotechnological Processes, 10:131 (1988).
26. Wang J. G., Steel S., Wisniewolski R., Wang C. Y.: Detection of antibodies to HTLV-III using a synthetic peptide of 21 amino acid residues corresponding to a highly antigenic segment of gp41 envelope protein. *Proc. Natl. Acad. Sci. USA* 83:6159 (1986).
27. Wang C. Y.: European Patent Application Publication: EPO 0328403 (1989). Synthetic peptides related to the HIV-gp120 env protein, and their use.
28. Wang C. Y., Wang J. G.: U.S. Pat. No. 4879212 (1989). Peptide composition and method for the detection of antibodies to HTLV-III.
29. Wang C. Y., Wang J. G.: U.S. Pat. No. 4,735,896 (1988). Synthetic peptide and process of using same for the detection and diagnosis of AIDS and pre-AIDS conditions.
30. Wang C. Y., Wang J. G., Walters D. W.: U.S. Pat. No. 4,833,071 (1989). Peptide composition as antigen for detection of antibodies to HTLV-I, as a vaccine for ATL, and methods therefore.
31. Wang C. Y.: U.S. Ser. No. 07/297,635. Synthetic peptide compositions with immunoreactivities to antibodies to HTLV.

BRIEF DESCRIPTION OF THE INVENTION

According to the present invention, a series of synthetic peptides representing immunoreactive regions of the postulated envelope protein and nonstructural proteins NS-1, NS-2, NS-3 and NS-5 of the hepatitis C virus (HCV), each arranged in a specific sequence, has been identified and made by solid phase peptide synthesis. These peptides have been found to be useful for the detection of antibodies to HCV in sera and body fluids and for the diagnosis of non-A, non-B hepatitis (NANBH). Because of their immunoreactivity, it is expected that these peptides are also useful in stimulating production of antibodies to HCV in healthy mammals such as Balb/C mice, and in a vaccine composition to prevent HCV or NANBHV infection.

According to the present invention, a peptide composition useful for the detection of antibodies to HCV and diagnosis of NANBH comprises a peptide from the envelope, NS-1, NS-2, NS-3 and NS-5 regions of the HCV represented by the following sequences:

Gln—Gly—Trp—Gly—Pro—Ile—Ser—Tyr—Ala—Asn—Gly—Ser—Gly—Pro—Asp— (a)
Gln—Arg—Pro—Tyr—Cys—Trp—His—Tyr—Pro—Pro—Lys—Pro—Cys—Gly—Ile—
Val—Pro—Ala—Lys—Ser—Val—Cys—Gly—Pro—Val—Tyr—Cys—X
Seq. ID 1 Pep1

Pro—Pro—Leu—Gly—Asn—Trp—Phe—Gly—Cys—Thr—Trp—Met—Asn—Ser—Thr— (b)
Gly—Phe—Thr—Lys—Val—Cys—Gly—Ala—Pro—Pro—Cys—X
Seq. ID 2 Pep2

Gly—Cys—Ser—Gly—Gly—Ala—Tyr—Asp—Ile—Ile—Ile—Cys—Asp—Glu—Leu— (c)
His—Ser—Thr—Asp—Ala—Thr—Ser—Ile—Leu—Gly—Ile—Gly—Thr—Val—Leu—
Asp—Gln—Ala—Glu—Thr—Ala—Gly—X
Seq. ID 3 Pep3

Asp—Pro—Ser—His—Ile—Thr—Ala—Glu—Ala—Ala—Gly—Arg—Arg—Leu—Ala— (d)
Arg—Gly—Ser—Pro—Pro—Ser—Val—Ala—Ser—Ser—Ser—Ala—Ser—Gln—Leu—
Ser—Ala—Pro—Ser—Leu—Lys—Ala—Thr—Cys—Thr—Ala—Asn—His—Asp—Ser—
Pro—X
Seq. ID 4 Pep4

Asp—Ala—Glu—Leu—Ile—Glu—Ala—Asn—Leu—Leu—Trp—Arg—Gln—Glu—Met— (e)
Gly—Gly—Asn—Ile—Thr—Arg—Val—Glu—Ser—Glu—Asn—Lys—Val—Val—Ile—
Leu—Asp—Ser—Phe—Asp—Pro—Leu—Val—Ala—Glu—Glu—Asp—Glu—Arg—X
Seq. ID 5 Pep5

Asp—Pro—Gln—Ala—Arg—Val—Ala—Ile—Lys—Ser—Leu—Thr—Glu—Arg—Leu— (f)
Thr—Val—Gly—Gly—Pro—Leu—Thr—Asn—Ser—Arg—Gly—Glu—Asn—Cys—Gly—
Tyr—Arg—Arg—Cys—Arg—Ala—Ser—X
Seq. ID 6 Pep6

Cys—Leu—Thr—Val—Pro—Ala—Ser—Ala—Tyr—Gln—Val—Arg—Asn—Ser—Thr— (g)
Gly—Leu—Tyr—His—Val—Thr—Asn—Asp—Cys—Pro—Asn—Ser—Ser—Ile—Val—
Tyr—Glu—Ala—His—Asp—Ala—Ile—Leu—His—Thr—Pro—Gly—Cys—Val—Pro—
Cys—Val—Arg—Glu—Gly—Asn—Val—Ser—Arg—Cys—X
Seq. ID 7 Pep7

Phe—Thr—Phe—Ser—Pro—Arg—Arg—His—Trp—Thr—Thr—Gln—Gly—Cys—Asn— (h)
Cys—Ser—Ile—Tyr—Pro—Gly—His—Ile—Thr—Gly—His—Arg—Met—Ala—Trp—
Asp—Met—Met—Met—Asn—Trp—Ser—Pro—Thr—Ala—X
Seq. ID 8 Pep8

Val—Asp—Ala—Glu—Thr—Ile—Val—Ser—Gly—Gly—Gln—Ala—Ala—Arg—Ala— (i)
Met—Ser—Gly—Leu—Val—Ser—Leu—Phe—Thr—Pro—Gly—Ala—Lys—Gln—Asn—
Ile—Gln—Leu—Ile—Asn—X
Seq. ID 9 Pep9

Trp—His—Ile—Asn—Ser—Thr—Ala—Leu—Asn—Cys—Asn—Glu—Ser—Leu—Asn— (j)
Thr—Gly—Trp—Leu—Ala—Gly—Leu—Ile—Tyr—Glu—His—Lys—Phe—Asn—Ser—
Ser—Gly—Cys—Pro—Glu—Arg—Leu—Ala—Ser—Cys—X
Seq. ID 10 Pep10

Glu—Ile—Leu—Arg—Lys—Ser—Arg—Arg—Phe—Ala—Gln—Ala—Leu—Pro—Val— (k)
Trp—Ala—Arg—Pro—Asp—Tyr—Asn—Pro—Pro—Leu—Val—Glu—Thr—Trp—Lys—
Lys—Pro—Asp—Tyr—Glu—Pro—Pro—Val—Val—His—Gly—Cys—Pro—Leu—Pro—
Pro—Pro—Lys—Ser—Pro—Pro—Val—Pro—Pro—Pro—Arg—Lys—Lys—Arg—Thr—
X
Seq. ID 11 Pep11

Lys—Ala—Thr—Cys—Thr—Ala—Asn—His—Asp—Ser—Pro—Asp—Ala—Glu—Leu— (l)
Ile—Glu—Ala—Asn—Leu—Leu—Trp—Arg—Gln—Glu—Met—Gly—Gly—Asn—Ile—
Thr—Arg—Val—Glu—Ser—Glu—Asn—Lys—Val—Val—Ile—Leu—Asp—Ser—Phe—
Asp—Pro—Leu—Val—Ala—Glu—Glu—Asp—Glu—Arg—X
Seq. ID 12 Pep12

Arg—Gln—Glu—Met—Gly—Gly—Asn—Ile—Thr—Arg—Val—Glu—Ser—Glu—Asn— (m)
Lys—Val—Val—Ile—Leu—Asp—Ser—Phe—Asp—Pro—Leu—Val—Ala—Glu—Glu—
Asp—Glu—Arg—Glu—Ile—Ser—Val—Pro—Ala—Glu—Ile—Leu—Arg—Lys—Ser—
Arg—Arg—X
Seq. ID 13 Pep13

Cys—Lys—Pro—Leu—Leu—Arg—Glu—Glu—Val—Ser—Phe—Arg—Val—Gly—Leu— (n)
His—Glu—Tyr—Pro—Val—Gly—Ser—Gln—Leu—Pro—Cys—Glu—Pro—Glu—Pro—
Asp—X
Seq. ID 14 Pep14

Glu—Glu—Tyr—Val—Glu—Ile—Arg—Gln—Val—Gly—Asp—Phe—His—Tyr—Val— (o)
Thr—Gly—Met—Thr—Thr—Asp—Asn—Leu—Lys—Cys—Pro—Cys—Gln—Val—Pro—
Ser—Pro—X
Seq. ID 15 Pep15

Gly—Ser—Trp—Leu—Arg—Asp—Ile—Trp—Asp—Trp—Ile—Cys—Glu—Val—Leu— (p)

-continued

Ser—Asp—Phe—Lys—Thr—Trp—Leu—Lys—Ala—Lys—Leu—Met—Pro—Gln—Leu—
X

Seq. ID 16 Pep16

Gly—Pro—Ala—Asp—Gly—Met—Val—Ser—Lys—Gly—Trp—Arg—Leu—Leu—Ala—  (q)
Pro—Ile—Thr—Ala—Tyr—Ala—Gln—Gln—Thr—Arg—Gly—Leu—Leu—Gly—Cys—
Ile—Ile—Thr—Ser—Leu—Thr—Gly—Arg—Asp—Lys—Asn—Gln—Val—Glu—Gly—
X

Seq. ID 17 Pep17

Glu—Ile—Pro—Phe—Tyr—Gly—Lys—Ala—Ile—Pro—Leu—Glu—Val—Ile—Lys—  (r)
Gly—Gly—Arg—His—Leu—Ile—Phe—Cys—his—Ser—Lys—Lys—Lys—Cys—Asp—
Glu—Leu—Ala—Ala—Lys—Leu—Val—Ala—Leu—X Seq. ID 18 Pep18

Cys—Val—Arg—Glu—Gly—Asn—Val—Ser—Arg—Cys—Trp—Val—Ala—Met—Thr—  (s)
Pro—Thr—Val—Ala—Thr—Arg—Asp—Gly—Lys—Leu—Pro—Ala—Thr—Gln—Leu—
Arg—Arg—His—Ile—Asp—Leu—Leu—Val—Gly—Ser—Ala—Thr—Leu—Cys—X

Seq. ID 19 Pep19

These 19 peptides are in addition to Peptide VIIIE, a peptide from the structural protein region, and Peptides IIH and V, peptides from the non-structural protein region which have also been found to be reactive and useful for the detection of antibodies to HCV and diagnosis of NANBH.

Peptide VIIIE has the following sequence:

Ser—Thr—Ile—Pro—Lys—Pro—Gln—Arg—Lys—Thr—Lys—Arg—His—Thr—Asn—Arg—
Arg—Pro—Gln—Asp—Val—Lys—Phe—Pro—Gly—Gly—Gly—Gln—Ile—Val—Gly—Gly—
Val—Tyr—Leu—Leu—Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—Arg—X, Seq. ID 20

Peptide IIH has the following sequence:

Ser—Gly—Lys—Pro—Ala—Ile—Ile—Pro—Asp—Arg—Glu—Val—Leu—Tyr—Arg—Glu—
Phe—Asp—Glu—Met—Glu—Glu—Cys—Ser—Gln—His—Leu—Pro—Tyr—Ile—Glu—Gln—
Gly—Met—Met—Leu—Ala—Glu—Gln—Phe—Lys—Gln—Lys—Ala—Leu—Gly—Leu—X Seq. ID 21

Peptide V has the following sequence:

Lys—Gln—Lys—Ala—Leu—Gly—Leu—Leu—Gln—Thr—Ala—Ser—Arg—Gln—Ala—Glu—
Val—Ile—Ala—Pro—Ala—Val—Gln—Thr—Asn—Trp—Gln—Lys—Leu—Glu—Thr—Phe—
Trp—Ala—Lys—His—Met—Trp—Asn—Phe—X Seq. ID 22 wherein X is —OH or —NH$_2$ and analogues, segments, mixtures, conjugates and polymers thereof.

Further, according to the present invention, the peptides by themselves, or when coupled to a protein or a polymeric carrier of homo or hetero dimers or higher oligomers by the use of homo or hetero functional multivalent cross linking reagents, or when directly synthesized and conjugated to a branching polyvalent lysine resin, can be used to elicit the production of antibodies to HCV in healthy mammals, including humans.

The method comprises introducing an effective amount of the peptide composition containing each of the individual peptides, analogues or segments or a mixture or a combination thereof, or in a polymeric form, into the body of a healthy mammal by intraperitoneal or subcutaneous injection.

Vaccines containing the peptides according to the present invention as the key immunogen may also be prepared as described above or by known methods. It is expected that such vaccine compositions may be useful to prevent HCV infection or NANBH.

DETAILED DESCRIPTION OF THE INVENTION

Figure 1:
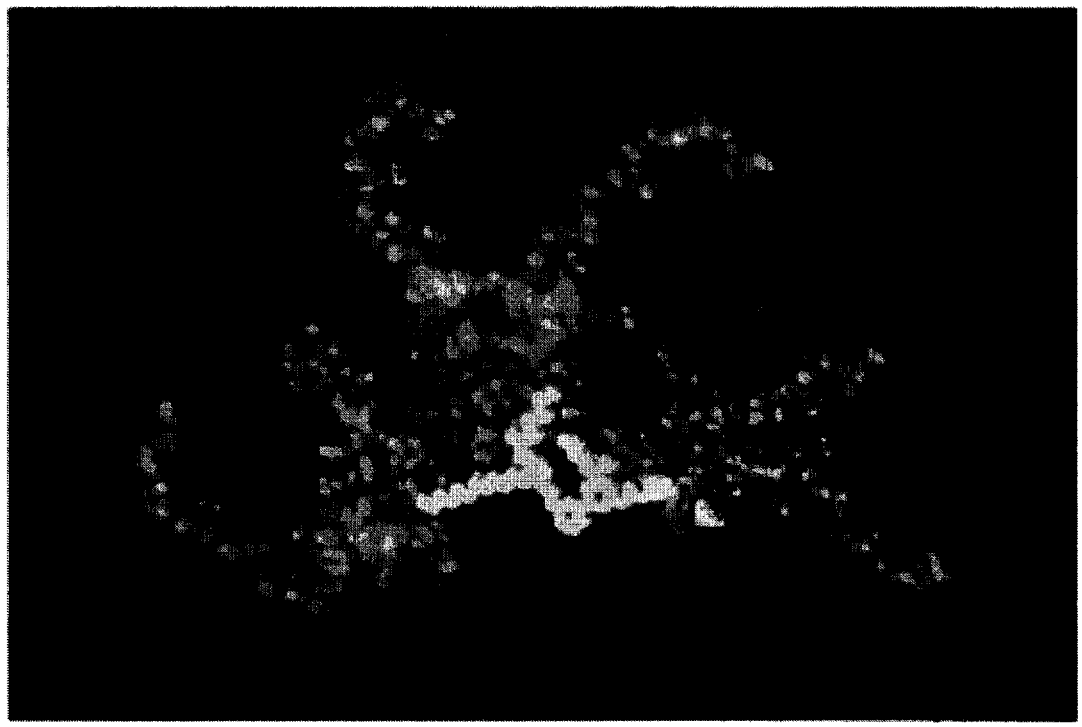
FIG. 1 is a photograph of a computer-generated structure of an octameric peptide immunogen.

In accordance with the present invention, nineteen peptides and their analogues including segments have been selected from the nonstructural regions of HCV and chemically synthesized. These peptides including their analogues are useful for the detection of antibodies to HCV in body fluids, the diagnosis of NANBH, and for the vaccination of healthy mammals by stimulating the production of antibodies to HCV. These peptides are arranged in the following sequences:

(a) Gln—Gly—Trp—Gly—Pro—Ile—Ser—Tyr—Ala—Asn—Gly—Ser—Gly—Pro—Asp—
Gln—Arg—Pro—Tyr—Cys—Trp—His—Tyr—Pro—Pro—Lys—Pro—Cys—Gly—Ile—
Val—Pro—Ala—Lys—Ser—Val—Cys—Gly—Pro—Val—Tyr—Cys—X
Seq. ID 1 Pep1

(b) Pro—Pro—Leu—Gly—Asn—Trp—Phe—Gly—Cys—Thr—Trp—Met—Asn—Ser—Thr—
Gly—Phe—Thr—Lys—Val—Cys—Gly—Ala—Pro—Pro—Cys—X
Seq. ID 2 Pep2

(c) Gly—Cys—Ser—Gly—Gly—Ala—Tyr—Asp—Ile—Ile—Ile—Cys—Asp—Glu—Leu—
His—Ser—Thr—Asp—Ala—Thr—Ser—Ile—Leu—Gly—Ile—Gly—Thr—Val—Leu—
Asp—Gln—Ala—Glu—Thr—Ala—Gly—X
Seq. ID 3 Pep3

(d) Asp—Pro—Ser—His—Ile—Thr—Ala—Glu—Ala—Ala—Gly—Arg—Arg—Leu—Ala—
Arg—Gly—Ser—Pro—Pro—Ser—Val—Ala—Ser—Ser—Ser—Ala—Ser—Gln—Leu—
Ser—Ala—Pro—Ser—Leu—Lys—Ala—Thr—Cys—Thr—Ala—Asn—His—Asp—Ser—
Pro—X
Seq. ID 4 Pep4

(e) Asp—Ala—Glu—Leu—Ile—Glu—Ala—Asn—Leu—Leu—Trp—Arg—Gln—Glu—Met—
Gly—Gly—Asn—Ile—Thr—Arg—Val—Glu—Ser—Glu—Asn—Lys—Val—Val—Ile—
Leu—Asp—Ser—Phe—Asp—Pro—Leu—Val—Ala—Glu—Glu—Asp—Glu—Arg—X
Seq. ID 5 Pep5

(f) Asp—Pro—Gln—Ala—Arg—Val—Ala—Ile—Lys—Ser—Leu—Thr—Glu—Arg—Leu—
Thr—Val—Gly—Gly—Pro—Leu—Thr—Asn—Ser—Arg—Gly—Glu—Asn—Cys—Gly—
Tyr—Arg—Arg—Cys—Arg—Ala—Ser—X
Seq. ID 6 Pep6

(g) Cys—Leu—Thr—Val—Pro—Ala—Ser—Ala—Tyr—Gln—Val—Arg—Asn—Ser—Thr—
Gly—Leu—Tyr—His—Val—Thr—Asn—Asp—Cys—Pro—Asn—Ser—Ser—Ile—Val—
Tyr—Glu—Ala—His—Asp—Ala—Ile—Leu—His—Thr—Pro—Gly—Cys—Val—Pro—
Cys—Val—Arg—Glu—Gly—Asn—Val—Ser—Arg—Cys—X
Seq. ID 7 Pep7

(h) Phe—Thr—Phe—Ser—Pro—Arg—Arg—His—Trp—Thr—Thr—Gln—Gly—Cys—Asn—
Cys—Ser—Ile—Tyr—Pro—Gly—His—Ile—Thr—Gly—His—Arg—Met—Ala—Trp—
Asp—Met—Met—Met—Asn—Trp—Ser—Pro—Thr—Ala—X
Seq. ID 8 Pep8

(i) Val—Asp—Ala—Glu—Thr—Ile—Val—Ser—Gly—Gly—Gln—Ala—Ala—Arg—Ala—
Met—Ser—Gly—Leu—Val—Ser—Leu—Phe—Thr—Pro—Gly—Ala—Lys—Gln—Asn—
Ile—Gln—Leu—Ile—Asn—X
Seq. ID 9 Pep9

(j) Trp—His—Ile—Asn—Ser—Thr—Ala—Leu—Asn—Cys—Asn—Glu—Ser—Leu—Asn—
Thr—Gly—Trp—Leu—Ala—Gly—Leu—Ile—Tyr—Glu—His—Lys—Phe—Asn—Ser—
Ser—Gly—Cys—Pro—Glu—Arg—Leu—Ala—Ser—Cys—X
Seq. ID 10 Pep10

(k) Glu—Ile—Leu—Arg—Lys—Ser—Arg—Arg—Phe—Ala—Gln—Ala—Leu—Pro—Val—
Trp—Ala—Arg—Pro—Asp—Tyr—Asn—Pro—Pro—Leu—Val—Glu—Thr—Trp—Lys—
Lys—Pro—Asp—Tyr—Glu—Pro—Pro—Val—Val—His—Gly—Cys—Pro—Leu—Pro—
Pro—Pro—Lys—Ser—Prp—Pro—Val—Pro—Pro—Arg—Lys—Lys—Arg—Thr—
X
Seq. ID 11 Pep11

(l) Lys—Ala—Thr—Cys—Thr—Ala—Asn—His—Asp—Ser—Pro—Asp—Ala—Glu—Leu—
Ile—Glu—Ala—Asn—Leu—Leu—Trp—Arg—Gln—Glu—Met—Gly—Gly—Asn—Ile—
Thr—Arg—Val—Glu—Ser—Glu—Asn—Lys—Val—Val—Ile—Leu—Asp—Ser—Phe—
Asp—Pro—Leu—Val—Ala—Glu—Glu—Asp—Glu—Arg—X
Seq. ID 12 Pep12

(m) Arg—Gln—Glu—Met—Gly—Gly—Asn—Ile—Thr—Arg—Val—Glu—Ser—Glu—Asn—
Lys—Val—Val—Ile—Leu—Asp—Ser—Phe—Asp—Pro—Leu—Val—Ala—Glu—Glu—
Asp—Glu—Arg—Glu—Ile—Ser—Val—Pro—Ala—Glu—Ile—Leu—Arg—Lys—Ser—
Arg—Arg—X
Seq. ID 13 Pep13

(n) Cys—Lys—Pro—Leu—Leu—Arg—Glu—Glu—Val—Ser—Phe—Arg—Val—Gly—Leu—
His—Glu—Tyr—Pro—Val—Gly—Ser—Gln—Leu—Pro—Cys—Glu—Pro—Glu—Pro—
Asp—X
Seq. ID 13 Pep14

(o) Glu—Glu—Tyr—Val—Glu—Ile—Arg—Gln—Val—Gly—Asp—Phe—His—Tyr—Val—
Thr—Gly—Met—Thr—Thr—Asp—Asn—Leu—Lys—Cys—Pro—Cys—Gln—Val—Pro—
Ser—Pro—X
Seq. ID 15 Pep15

-continued (p) Gly—Ser—Trp—Leu—Arg—Asp—Ile—Trp—Asp—Trp—Ile—Cys—Glu—Val—Leu—
Ser—Asp—Phe—Lys—Thr—Trp—Leu—Lys—Ala—Lys—Leu—Met—Pro—Gln—Leu—
X Seq. ID 16 Pep16

(q) Gly—Pro—Ala—Asp—Gly—Met—Val—Ser—Lys—Gly—Trp—Arg—Leu—Leu—Ala—
Pro—Ile—Thr—Ala—Tyr—Ala—Gln—Gln—Thr—Arg—Gly—Leu—Leu—Gly—Cys—
Ile—Ile—Thr—Ser—Leu—Thr—Gly—Arg—Asp—Lys—Asn—Gln—Val—Glu—Gly—
X

Seq. ID 17 Pep17

(r) Glu—Ile—Pro—Phe—Tyr—Gly—Lys—Ala—Ile—Pro—Leu—Glu—Val—Ile—Lys—
Gly—Gly—Arg—His—Leu—Ile—Phe—Cys—His—Ser—Lys—Lys—Lys—Cys—Asp—
Glu—Leu—Ala—Ala—Lys—Leu—Val—Ala—Leu—X

Seq. ID 18 Pep18

(s) Cys—Val—Arg—Glu—Gly—Asn—Val—Ser—Arg—Cys—Trp—Val—Ala—Met—Thr—
Pro—Thr—Val—Ala—Thr—Arg—Asp—Gly—Lys—Leu—Pro—Ala—Thr—Gln—Leu—
Arg—Arg—His—Ile—Asp—Leu—Leu—Val—Gly—Ser—Ala—Thr—Leu—Cys—X

Seq. ID 19 Pep19

These 19 peptides are in addition to Peptide VIIIE, a peptide from the structural protein region, and Peptides IIH and V, peptides from the non-structural protein region which have also been found to be reactive and useful for the detection of antibodies to HCV and diagnosis of NANBH.

Peptide VIIIE has the following sequence:

Ser—Thr—Ile—Pro—Lys—Pro—Gln—Arg—Lys—Thy—Lys—Arg—His—Thr—Asn—Arg—
Arg—Pro—Gln—Asp—Val—Lys—Phe—Pro—Gly—Gly—Gly—Gln—Ile—Val—Gly—Gly—
Val—Tyr—Leu—Leu—Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—Arg—X, Seq. ID 20

Peptide IIH has the following sequence:

Ser—Gly—Lys—Pro—Ala—Ile—Ile—Pro—Asp—Arg—Glu—Val—Leu—Tyr—Arg—Glu—
Phe—Asp—Glu—Met—Glu—Glu—Cys—Ser—Gln—His—Leu—Pro—Tyr—Ile—Glu—Gln—
Gly—Met—Met—Leu—Ala—Glu—Gln—Phe—Lys—Gln—Lys—Ala—Leu—Gly—Leu—X Seq. ID 21

Peptide V has the following sequence:

Lys—Gln—Lys—Ala—Leu—Gly—Leu—Leu—Gln—Thr—Ala—Ser—Arg—Gln—Ala—Glu—
Val—Ile—Ala—Pro—Ala—Val—Gln—Thr—Asn—Trp—Gln—Lys—Leu—Glu—Thr—Phe—
Trp—Ala—Lys—His—Met—Trp—Asn—Phe—X Seq. ID 22

Wherein X is —OH or —NH$_2$ and analogues, segments, mixtures, conjugates, and polymers thereof.

These peptides may comprise combinations or segments, i.e. longer or shorter peptide chains by having more amino acids added to the terminal amino acids, or by amino acids removed from either terminal end.

These peptides may also comprise analogues to accommodate strain-to-strain variations among different isolates of HCV. HCV is indicated to have frequent mutations. Therefore, it is expected that variant strains, such as PT, J, J-1 and J-4 (1–4) exist. Adjustments for conservative substitutions and selection among the alternatives where non-conservative substitutions are involved, may be made in the prescribed sequences (e.g. see Table 1E, Table 8c and Table 11 for possible amino acid substitutions in the hypervariable regions of the envelope and NS-1 proteins). These analogues of the synthetic peptides may therefore comprise substitutions, insertions and/or deletions of the recited amino acids of the above sequence to accommodate the various strains, as long as the immunoreactivity recognizable by the antibodies to HCV is preserved.

These peptides may also comprise conjugates, i.e., they may be coupled to carrier proteins such as bovine serum albumin (BSA) or human serum albumin (HSA). Furthermore, these peptides may comprise polymers, i.e., they may be synthesized on a polymeric resin, such as a branching octameric lysine resin.

The amino acid sequences of the polypeptide as described in the invention useful as test reagents for the detection of antibodies to HCV in body fluids and diagnosis of NANBH are selected to correspond to segments of the amino acid sequence of the postulated envelope and non-structural proteins of HCV designated as env, NS-1, NS-2, NS-3 and NS-5 based on amino acid sequence information derived from Houghton et al. (13), Okamoto et al (2) and Kato et al (4).

In selecting regions of the HCV protein for epitope analysis, peptides of about 40 mer size with amino acid sequences covering the complete HCV envelope and non-structural proteins NS-1, NS-2, NS-3 and NS-5 were synthesized. These were tested for their immunoreactivity with special specimens previously selected through the screening of thousands of patient and normal sera for their unique immunoreactivity with HCV. Nineteen peptides from the postulated envelope and nonstructural protein regions NS-1, NS-2, NS-3 and NS-5 designated as pep1, pep2, pep3, pep4, pep5, pep6, pep7, pep8, pep9, pep10, pep11, pep12, pep13, pep14, pep15, pep16, pep17, pep18 and pep19 and their analogues were identified to have specific immunoreactivity with the positive HCV sera.

At present, available knowledge of protein structure has not enabled the scientist to predict the amino acid sequences that may represent highly immunogenic epitopes. The usefulness of a peptide as an antigen or immunogen must be empirically determined. We have only been able to identify and characterize immuno-reactive epitopes through an extensive process which we call "serological validation". The following example shows how difficult it is to identify immuno-reactive epitopes.

For example, a clone designated as C33c encoded within the NS-3 region was reported to possess immunoreactivity (3). This clone spans 265 amino acid residues. Assuming a useful peptide must be at least 6 amino acids in length and that the upper limit for synthetic peptides in reasonable yield is 120 residues, the number of possible unique peptides from the C33c regions is 23,028. For the entire HCV genome, the figure is about 260,000.

In addition, we have shown that extraction conditions are critical for the expression of the immunopotency of a peptide (Example 4C), so the number of uniquely extracted peptides from this region is in multiples of 23,028. The possibilities for post-extraction modification, such as pH adjustment (Example 4B) further increase the possible selections to $>10^6$. If amino acid substitutions at various positions are taken into consideration, this figure will quickly increase to several millions. In contrast to the HCV core region, in which peptides VIIIE and IXD were the optimal analogues, longer peptides are not preferred over shorter analogues in the NS-3/C33c region. For example, the 42 mer 279B shown on Table 4D has only 3% of the reactivity of the 37 mer peptide 3, designated as 279A in Table 4D. Of 30 peptides spanning the C33c region tested, only one was found to be useful. The antigenic index as referred in Houghton et al (3) did not prove to be a useful guide to epitopes, as the profile for peptide 3 is positive for only 30% of its sequence and negative for the remaining 70%.

The strategy for serological validation also depends on the expected characteristics of the target epitopes. Universal immunodominant epitopes, such as the gp41 transmembrane peptide of HIV-1, may be screened by a single representative serum sample from a patient known to be infected with the virus. Epitopes which are not recognized by all infected individuals, or those for which antibody is produced late or only transiently, and especially epitopes which give rise to neutralizing antibodies, must be screened by large panels of sera. For example, peptide 272B shown in Table 4A was initially tested on a panel of eight sera from HCV infected individuals (Panel 1). Only one sample was definitely positive with an absorbance of 880 mA. Three were weakly reactive (<200 mA) and four were negative.

The identification of the immuno-reactive epitopes is also dependent on the panel of sera used. The more closely the panel represents the population most likely to be seropositive for the desired epitope, the greater the chance that the epitope will be identified. For example, peptides synthesized from the NS-1 region, which were hypothesized to be important for generating neutralizing antibodies, gave only weakly reactive or negative results on screening with a very large number (n>200) of samples from individuals who were newly infected and/or chronically infected with HCV. However, a panel of 24 samples from asymptomatic individuals from a known hepatitis virus endemic geographical region, Taiwan and mainland China, yielded two samples with absorbances of >2000 mA against multiple NS-1 peptides.

Finally, if the desired purpose of a targeted peptide/epitope is to extend the range of reactivity of an assay comprised of previously identified epitopes, then a large number of samples from individuals at risk of infection but seronegative against known epitopes must be employed for screening. Unfortunately, the most critical samples from clinically proven and documented cases of infection may be available in quantities insufficient for screening purposes. This is another complication/difficulty encountered in serological validation for determining the immunoreactivity of a peptide.

The process of "serological validation" is particularly difficult when the epitopes to be identified elicit antibodies only in a subpopulation of an infected patient group. When such epitopes become targets for identification, special attention must be paid to synthetic peptides which show very weak reactivity when tested by an enzyme immunoassay.

Fortunately, the low background absorbance of synthetic peptides allows for the precise detection of weak reactivities. In some cases, absorbances of 50 mA versus background reading are of sufficient significance and can lead to the identification of important epitopes through successive refinement of the amino acid sequence of a peptide. The utmost technical skill is required to obtain consistent and reliable results when working in the range of absorbances below 200–300 mA. For example: Peptides 261E and 261F shown on Table 4D were reactive with only one of eight HCV sera panel members (Panel I), with absorbances of 307 and 269 mA, respectively. Yet this weak reactivity led to the eventual identification of pep3 (or 279A), toward which half of the panel is reactive, and toward which some additional reactive samples show absorbances of >2000 mA.

Based on the immunoreactivities of the peptides according to the present invention, it is believed that these peptides may also be useful in a vaccine to prevent NANBH. The peptide when coupled to a protein, or synthesized on a polymeric carrier resin (e.g., an octameric lysine resin) or when polymerized to homo or hetero dimers or higher oligomers by cysteine oxidation, or induced disulfide cross linking, or by use of homo or hetero functional multivalent cross linking reagents, can be introduced to normal subjects to stimulate production of antibodies to HCV in healthy mammals.

The advantages of using synthetic peptides are known.

Since the peptides according to the present invention are not derived biologically from the virus, there is no danger of exposing the normal subjects who are to be vaccinated to the disease causing pathogen.

The peptides can be chemically synthesized easily. This means that there is no involvement with HCV at any time during the process of making the test reagent or the vaccine. Another problem which can be minimized by the process of the present invention is the false positive results caused by the presence of antigenic material co-purified with the HCV fusion protein. Certain normal individuals have antibodies to E. coli or yeast proteins which are cross reactive with the antigenic materials from the expression system. Sera from these normal individuals may show a positive reaction in the immunoassays.

Further, with appropriate amino acid modification or substitutions, it is expected that various peptide analogues based on the prescribed amino acid sequence can be synthesized with properties giving rise to lower background readings or better binding capacity to solid phases useful for HCV antibody screening assays.

Moreover, because the peptide compositions of the present invention are synthetically prepared, the quality can be controlled and as a result, reproducibility of the test results can be assured. Also, since very small amounts of a peptide are required for each test procedure, and because the expense of preparing a peptide is relatively low, the cost of screening body fluids for antibodies to HCV, diagnosis of NANBH infection, and the preparation of a vaccine is relatively low.

The peptides prepared in accordance with the present invention can be used to detect HCV infection and diagnose NANBH by using them as the test reagent in an enzyme-linked immunoadsorbent assay (ELISA), an enzyme immunodot assay, an agglutination based assay, or other well-known immunosassay devices. The following examples serve to illustrate the present invention and are not to be used to limit the scope of the invention.

This substrate mixture was used to detect the peroxidase label by forming a colored product. Reactions were stopped by the addition of 100 uL of 1.0M $H_2SO_4$ and the $A_{492}$ mm measured. Results of relative immunoreactivity for each of the peptides obtained from this study are shown in Table A using peptide II H as the reference.

TABLE A

| Peptide Code | $A_{492}$ nm (Panel I, No. 1 to 8) | | | | | | | | Total | % |
|---|---|---|---|---|---|---|---|---|---|---|
| | 1 | 2 | 3 | 4 | 5 | 6 | 7 | 8 | | |
| IIH | 0.812 | 0.656 | 3.114 | 2.737 | 1.066 | 2.254 | 2.599 | 3.478 | 16.712 | 100 |
| V | 0.834 | 1.060 | 2.931 | 0.534 | 0.137 | 0.434 | 0.303 | 2.787 | 9.020 | 54 |
| VIIIE | 2.745 | 2.208 | 2.468 | 3.032 | 0.054 | 2.108 | 0.730 | 3.006 | 16.351 | 98 |
| Pep11 | 0.241 | 0.715 | 3.162 | 1.020 | 0.568 | 2.166 | 3.330 | 3.477 | 14.690 | 88 |

EXAMPLE 1

Measurement of Relative (%) Immunoreactivity for HCV synthetic peptides by an Enzyme-Linked Immunosorbent Assay As an example to illustrate how relative (%) immunoreactivity for HCV synthetic peptides is measured, wells of 96-well plates are coated for 1 hour at 37° C., with each of the following peptides: IIH, V, VIIIE and pep11 at 5 ug/mL at 100 uL per well in 10 mM $NaHCO_3$ buffer, pH 9.5. The peptide coated wells were then incubated with 250 uL of 3% by weight of gelatin in PBS in 37° C. for 1 hour to block non-specific protein binding sites, followed by three washes with PBS containing 0.05% by volume of TWEEN 20 and then dried. The test specimens containing a panel of eight well-characterized HCV antibody positive patient sera were diluted with PBS containing 20% by volume normal goat serum, 1% by weight gelatin and 0.05% by volume TWEEN 20 at dilutions of 1:20 volume to volume, respectively. 200 uL of the diluted specimens were added to each of the wells and allowed to react for 15 minutes at 37° C.

The wells were then washed six times with 0.05% by volume TWEEN 20 in PBS in order to remove unbound antibodies. Horseradish peroxidase conjugated goat anti-human IgG was used as a second antibody tracer to bind with the HCV antibody-peptide antigen complex formed in positive wells. 100 uL of peroxidase labeled goat anti-human IgG at a dilution of 1:1800 in 1% by volume normal goat serum, 0.05% by volume TWEEN 20 in PBS was added to each well and incubated at 37° C. for another 15 minutes.

The wells were washed six times with 0.05% by volume TWEEN 20 PBS to remove unbound antibody and reacted with 100 uL of the substrate mixture containing 0.04% by weight orthophenylenediamine (OPD) and 0.12% by volume hydrogen peroxide in sodium citrate buffer, pH 5.0.

EXAMPLE 2

Comparison of HCV Immunoreactivities by a Well-characterized 8 Member HCV Serum Panel (Panel I) for % Relative Immunoreactivity with a Group of HCV Capsid Protein Related Peptides by an Enzyme Immunoassay A 36 mer HCV capsid peptide recently disclosed by Okamoto et al.(8) as the basis of an HCV EIA was synthesized for the purpose of comparison of immunoreactivity with peptides VIIIA, VIIIB and VIIIE (Table 2A). According to a procedure described in Example 1, peptides were coated at concentrations of 5, 1 and 0.2 µg/mL for immunopotency comparison. This 36 mer exhibited only 47.8% of the reactivity of VIIIE (Table 2A). More importantly, when tested by our well-characterized HCV serum panel used for serological validation, only 4 out of 8 samples reacted with the 36 mer, compared with 7 out of 8 with VIIIE. The C terminal end of this 36 mer does not appear to contribute to the peptide's HCV immunoreactivity, since IXD is not greater in reactivity than IXC (Table 2A).

In addition, a 61 mer peptide and fragments thereof consisting of a 30 mer, a 40 mer and a 50 mer corresponding to sequences from Arima clone 1, which is homologous to the capsid region of the flavivirus yellow fever virus, were synthesized and compared in immunoreactivity with peptide VIIIE from the corresponding region of HCV (Table 2B). The 40 mer and 61 mer of clone 1 exhibited the most reactivity. However these were only 21.1% and 20.7%, respectively, of the immunoreactivity of peptide VIIIE.

TABLE 2A

| | Sequence | % Relative Immunoreactivity |
|---|---|---|
| Okamoto(8) et al. [36 mer] Seq. ID 23 | RRGPRLGVRATRKTSERSQPRGRRQPIPKVRRPEGR | 47.8% |
| VIIA Seq. ID 24 | GPRLGVRATRKTSERSQPRGRR | 32.7% |
| VIIB Seq. ID 25 | VGGVYLLPRRGPRLGVRATRKTSERSQPRGRR | 48.9% |
| VIIE Seq. ID 26 | STIPKPQRKTKRNTNRRPQDVKFPGGGQIVGGVYLLPRRGPRLGVRATRKTSERSQPRGRR | 100.0% |
| IXC Seq. ID 27 | TWAQPGYPWPLYGNEGCGWAGWLLSPRGSRPSWGPTDPRRRSRNLG | 57.9% |
| IXD Seq. ID 28 | IPKVRRPEGRTWAQPGYPWPLYGNEGCGWAGWLLSPRGSRPSWGPTDPRRRSRNLG | 58.9% |
| IXE Seq. ID 29 | GRRQPIPKVRRPEGRTWAQPGYPWPLYGNEGCGWAGWLLSPRGSRPSWGPTDPRRRSRNLG | 50.2% |

TABLE 2B

| Arima et al. (12) | | % Relative Immunoreactivity |
|---|---|---|
| 30 mer Seq. ID 30 | PGKNKKPRVGRIKNWNREGRKDAYQIRKRR | 0.7% |
| 40 mer Seq. ID 31 | KEKEKTATNNPGKNKKPRVGRIKNWNREGRKDAYQIRKRR | 21.1% |
| 50 mer Seq. ID 32 | KKQRRYKEKEKTATNNPGKNKKPRVGRIKNWNREGRKDAYQIRKRR | 17.8% |
| 61 mer Seq. ID 33 | KKGEASNGEAENDTHKKQRRYKEKEKTATNNPGKNKKPRVGRIKNWNREGRKDAYQIRKRR | 20.7% |

EXAMPLE 3

Relative (%) Immunoreactivity for NS-1 Synthetic Peptides by an Enzyme-Linked Immunosorbent Assay (A) Identification of Immunoreactive NS-1 Peptides Wells of 96-well plates were coated for 1 hour at 37° C. with each of the 16 peptides (designated as peptides 241A-C, 231A-E, 232A-D, 233C, 234A-C), synthesized according to sequences derived from the NS-1 region (Table 3A), at 5 ug/mL at 100 uL per well in 10 mM NaHCO$_3$ buffer, pH 9.5. Each peptide's immunoreactivity was measured as previously described (see Example 1), using an 8 member serum panel (Panel I).

All sixteen peptides showed little or no reactivity with serum panel I. The most reactive peptide, pep1 (designated 231c in Table 3A), had an immunopotency index of 13.9%, compared with peptide VIIIE on the same panel. There were isolated examples of epitope recognition; for example, for sample 4, all analogues of the 232 series had absorbances less than or equal to 20 mA except for the longest peptide, 232D, which had an absorbance of 785 mA. However, the remaining 7 panel members were negative when tested with 232D.

After screening these 16 NS-1 region derived peptides with more than 200 additional HCV positive sera with little or no demonstrated immunoreactivities, immunoreactivities of these 16 NS-1 peptides with other sera were sought. A panel of serum samples from individuals coming from regions in which hepatitis C is endemic, namely mainland China and Taiwan, were tested for evidence of reactivity to these NS-1 protein derived peptides. Twenty-four samples were chosen from individuals who had no recognizable symptoms of non-A, non-B hepatitis and for whom the peptide based HCV EIA, Format C, as described in Example 11, was nonreactive. Seven of the 24 samples (29%) were reactive against one or more peptides from the NS-1 region, indicative of the presence of long term protective antibodies responsive to this region. This 7 member panel (designated as Panel II, CH1–CH7) was used to further characterize these NS-1 peptides for their immunoreactivity.

The peptide with the greatest reactivity against the serum Panel II again was pep1 (designated 231c in Table 3A). Using this peptide as a standard, the relative immunoreactivity for each of the other 15 peptides from the NS-1 region are calculated in Table 3A.

Detailed results from the seven member serum Panel II on four of the most immunoreactive analogues (i.e. pep1, or 231C; pep2, or 232A; 233C and 234A) are tabulated in Table 3B. The reactivities of 231C and 232A are complementary in that CH-1 and CH-2 are strongest on 231C, whereas CH-3 through CH-7 are stronger on 232A.

(B) NS-1 Reactivity in Early and Long-term HCV Infection

In addition, all sixteen NS-1 peptides were tested on panels of samples representing HCV-antibody positive donors (n=9) in an early stage of infection, namely plasmapheresis donors with the first occurrence of an ALT level >100 i.u./L, and those asymptomatic individuals (n=14) disqualified from blood donation because of a reactive result for anti-HIV or HBc, for whom the anti-HCV result probably represents a past infection.

These select panels were chosen from hundreds of HCV positive sera for their ability to recognize NS-1 antigens. The results of testing the panels with the 16 NS-1 peptides are given in Table 3C. For both groups, peptide designated as 232A (pep2) had the greatest immunoreactivity. Using pep2 as a standard, the relative immunoreactivity of each peptide was calculated (Table 3C).

TABLE 3A

Synthetic Peptides with their Amino Acid Sequences derived from the HCV NS-1 Protein Region

| | Sequence | % IP |
|---|---|---|
| 241A Seq. ID 34 | CPERLASCRPLTDFDQGWGPISYANGSGPDQRPYCWHYPPKPCGIVPAKSVCGPVYCFTPSPVVVGTTDRSGAPTYSWGENDTDVFVLNNTRPPLGNWFGCTWMNSTGFTKVCGAPPC QGWGPISYANGSGPDQRPYCWHYPPKPCGIVPAKSVC | 63.9 |
| 241B Seq. ID 35 | CRPLTDFDQGWGPISYANGSGPDQRPYCWHYPPKPCGIVPAKSVC | 92.9 |
| 241C Seq. ID 36 | CPERLASCRPLTDFDQGWGPISYANGSGPDQRPYCWHYPPKPCGIVPAKSVC | 93.6 |
| 231A Seq. ID 37 | RPYCWHYPPKPCGIVPAKSVCGPVYC | 83.2 |
| 231B Seq. ID 38 | ANGSGPDQRPYCWHYPPKPCGIVPAKSVCGPVYC | 96.4 |
| 231C (Pep1) Seq. ID 1 | QGWGPISYANGSGPDQRPYCWHYPPKPCGIVPAKSVCGPVYC | 100.0 |
| 231D Seq. ID 39 | CRPLTDFDQGWGPISYANGSGPDQRPYCWHYPPKPCGIVPAKSVCGPVYC | 65.3 |
| 231E Seq. ID 40 | CPERLASCRPLTDFDQGWGPISYANGSGPDQRPYCWHYPPKPCGIVPAKSVCGPVYC | 87.6 |
| 232A (Pep2) Seq. ID 2 | PPLGNWFGCTWMNSTGFTKVCGAPPC | 88.7 |
| 232B Seq. ID 41 | VFVLNNTRPPLGNWFGCTWMNSTGFTKVCGAPPC | 82.9 |
| 232C Seq. ID 42 | SWGENDTDVFVLNNTRPPLGNWFGCTWMNSTGFTKVCGAPPC | 27.9 |
| 232D Seq. ID 43 | DRSGAPTYSWGENDTDVFVLNNTRPPLGNWFGCTWMNSTGFTKVCGAPPC | 25.9 |
| 233C Seq. ID 44 | VIGGAGNNTLHCPTDCFRKHPDATYSRCGSGPWITPRCLVDYPYRLWHWPCTINYTIFKIRMYVGGVEHRLEAACNWTRGERCDLEDRDRSELS | 16.8 |
| 234A Seq. ID 45 | LHCPTDCFRKHPDATYSRCGSGPWITPRCLVDYPYRLWHWPC | 20.5 |
| 234B Seq. ID 46 | EAACNWTRGERCDLEDRDRSELS | 17.9 |
| 234C Seq. ID 47 | VGGVEHRLEAACNWTRGERCDLEDRDRSELS | 8.8 |
| | TIFKIRMYVGGVEHRLEAACNWTRGERCDLEDRDRSELS | |

TABLE 3B

| Sample No. (Panel II) | 231C (Pep1) | 232A (Pep2) | 233C | 234A |
|---|---|---|---|---|
| | A492 nm by EIA (mA) | | | |
| CH-1 | 2237 | 202 | 123 | 118 |
| CH-2 | 2472 | 261 | 174 | 232 |
| CH-3 | 171 | 935 | 72 | 64 |
| CH-4 | 218 | 1498 | 238 | 227 |
| CH-5 | 311 | 621 | 114 | 206 |
| CH-6 | 247 | 1128 | 175 | 202 |
| CH-7 | 206 | 552 | 89 | 151 |

TABLE 3C

Panel I.D.

| Peptide Code | Early HCV Infection | Late HCV Infection |
|---|---|---|
| | Panel Size | |
| | n = 9 | n = 14 |
| | % Relative Immunoreactivity in comparison to Pep2 (232A) | |
| 241A | 23.9 | 43.8 |
| 241B | 32.7 | 75.0 |
| 241C | 44.7 | 84.7 |
| 231A | 46.8 | 48.4 |
| 231B | 30.9 | 46.7 |
| 231C (Pep1) | 88.6 | 62.7 |
| 231D | 23.3 | 43.5 |
| 231E | 70.9 | 83.4 |
| 232B | 91.4 | 83.5 |
| 232C | 21.7 | 22.0 |
| 232D | 50.0 | 46.7 |
| 233A | 9.9 | 17.5 |
| 234A | 9.5 | 15.7 |
| 234B | 13.2 | 20.9 |
| 234C | 12.1 | 44.5 |

EXAMPLE 4

Relative (%) Immunoreactivity for NS-3 Protein Derived Synthetic Peptides by an Enzyme-Linked Immunosorbent Assay (A) Identification of NS-3 Protein Derived Immunoreactive Peptides Wells of 96-well plates were coated for 1 hour at 37° C. with each of the 30 peptides (designated as 261A-F, 262A-F, 272A-C, 274A-D, 275A-D, 278A-D and 279A,B,E), synthesized with sequences derived from the NS-3 region, at 5 ug/mL at 100 uL per well in 10 mM NaHCO₃ buffer, pH 9.5. The immunoreactivity of each peptide was measured by an 8 member HCV serum panel (Panel I). The peptide with the greatest immunoreactivity, pep3, designated 279A in Table 4D, had a relative immunoreactivity value of 23.9%, compared with peptide VIIIE (data not shown). When the immunoreactivity of peptide 3 was used as a standard to calculate the relative immunopotency for the other NS-3 peptides (Tables 4A, 4B, 4C and 4D), all other 29 peptides were found to be marginally immunoreactive. More surprisingly, the sequence of pep3 (or 279A), a 37 mer, is entirely contained within peptides 261E, 261F, 274B, 274C, 274D, 279B and 279E, yet these seven larger peptides have relative immunoreactivity in the range of only 2.2 to 34%, when compared to their segment pep3. Another surprise was the observation that the mere addition of 5 residues to the N terminus of pep3 completely abrogates the reactivity of the peptide (see the relative immunoreactivity of pep3 vs. peptide 279B, Table 4D).

TABLE 4A

HCV NS-3 PROTEIN DERIVED SYNTHETIC PEPTIDES

| | | % IP |
|---|---|---|
| 272A Seq. ID 48 | AVDFIPVENLETTMRSPVFTDNSSPPVVPQSFQVAHLHAPTGSGKSTKVPAAYAAQGYKVLVLNPS VAATLGFGAYMSKAHGIDPNIRTGV | 2.1 |
| 272B Seq. ID 49 | PVVPQSFQVAHLHAPTGSGKSTKVPAAYAAQGYKVLVLNPS | |
| 272C Seq. ID 50 | TTMRSPVFTDNSSPPVVPQSFQVAHLHAPTGSGKSTKVPAAYAAQGYKVLVLNPS | 38.0 |
| 278A Seq. ID 51 | AVDFIPVENLETTMRSPVFTDNSSPPVVPQSFQVAHLHAPTGSGKSTKVPAAYAAQGYKVLVLNPS | 11.8 |
| 278B Seq. ID 52 | PVVPQSFQVAHLHAPTGSGKSTKVPAAYA | 8.2 |
| 278C Seq. ID 53 | FTDNSSPPVVPQSFQVAHLHAPTGSGKSTKPAAYA | 1.4 |
| 278D Seq. ID 54 | VENLETTMRSPVFTDNSSPPVVPQSFQVAHLHAPTGSGKSTKVPAAYA | 10.7 |
| | AVDFIPVENLETTMRSPVFTDNSSPPVVPQSFQVAHLHAPTGSGKSTKVPAAYA | 11.6 |

TABLE 4B

HCV NS-3 PROTEIN DERIVED SYNTHETIC PEPTIDES

| | Sequence | % Relative Immunoreactivity |
|---|---|---|
| 275A Seq. ID 55 | TMRSPVFTDNSSPPVVPQSFQVAHLHAPTGSGKSTKVPAAYAAQGYKVLVLNPSVAATLGFGAYMSKAHGIDPNIRTGVRTITTGSPITYSTYGKFLADGGCSGGAYDIIICDECHS | 18.2 |
| 275B Seq. ID 56 | KITTTGSPITYSTYGKFLADGGCSGGAYDIIICDECHS | 11.1 |
| 275C Seq. ID 57 | LVLNPSVAATLGFGAYMSKAHGIDPNIRTGVRTITTGSPITYSTYGKFLADGGCSGGAYDIIICDECHS | 9.6 |
| 275D Seq. ID 58 | HLHAPTGSGKSTKVPAAYAAQGYKVLVLNPSVAATLGFGAYMSKAHGIDPNIRTGVRTITTGSPITYSTYGKFLADGGCSGGAYDIIICDECHS | 5.4 |

Note: 275D sequence shown in image is actually TMRSPVFTDNSSPPVVPQSFQVAHLHAPTGSGKSTKVPAAYAAQGYKVLVLNPSVAATLGFGAYMSKAHGIDPNIRTGVRTITTGSPITYSTYGKFLADGGCSGGAYDIIICDECHS

TABLE 4C

HCV NS-3 PROTEIN DERIVED SYNTHETIC PEPTIDES

| | Sequence | % Relative Immunoreactivity |
|---|---|---|
| 274A Seq. ID 59 | GYKVLVLNPSVAATLGFGAYMSKAHGIDPNIRTGVRTITTGSPITYSTYGKFLADGGCSGGAYDIIICDECHSTDATSILGIGTVLDQAETAGARLVVLATATPPGSVTVPHPNIEEVAL | 2.0 |
| 274B Seq. ID 60 | TVLDQAETAGARLVVLATATPPGSVTVPHPNIEEVAL | 34.0 |
| 274C Seq. ID 61 | GCSGGAYDIIICDECHSTDATSILGIGTVLDQAETAGARLVVLATATPPGSVTVPHPNIEEVAL | 3.9 |
| 274D Seq. ID 62 | AHGIDPNIRTGVRTITTGSPITYSTYGKFLADGGCSGGAYDIIICDECHSTDATSILGIGTVLDQAETAGARLVVLATATPPGSVTVPHPNIEEVAL | 2.8 |
| 262A Seq. ID 63 | GYKVLVLNPSVAATLGFGAYMSKAHGIDPNIRTGVRTITTGSPITYSTYGKFLADGGCSGGAYDIIICDELHSTDAT | 6.9 |
| 262B Seq. ID 64 | YGKFLADGGCSGGAYDIIICDECHSTDAT | 4.7 |
| 262D Seq. ID 65 | TTGSPITYSTYGKFLADGGCSGGAYDIIICDECHSTDAT | 9.3 |
| 262E Seq. ID 66 | PNIRTGVRTITTGSPITYSTYGKFLADGGCSGGAYDIIICDECHSTDAT | 3.6 |
| 262F Seq. ID 67 | AYMSKAHGIDPNIRTGVRTITTGSPITYSTYGKFLADGGCSGGAYDIIICDECHSTDAT | 4.7 |
| 262F Seq. ID 67 | SVAATLGFGAYMSKAHGIDPNIRTGVRTITTGSPITYSTYGKFLADGGCSGGAYDIIICDECHSTDAT | 5.1 |
| 262F Seq. ID 68 | GYKVLVLNPSVAATLGFGAYMSKAHGIDPNIRTGVRTITTGSPITYSTYGKFLADGGCSGGAYDIIICDECHSTDAT | |

TABLE 4D

HCV NS-3 PROTEIN DERIVED SYNTHETIC PEPTIDES

| | Sequence | % Relative Immunoreactivity |
|---|---|---|
| 261A Seq. ID 69 | RITITGSPITYSTYGKFLADGGCSGGAYDIIICDECHSTDATSILGIGTVLDQAETAGARLVVLATATPPGSVTVPHPNIEEVALSTTGEIPFYGKAIPLEVIKGGRHLIFCHSKKKCDEL | 7.2 |
| 261B Seq. ID 70 | PFYGKAIPLEVIKGGRHLIFCHSKKKCDEL | 3.1 |
| 261C Seq. ID 71 | EVALSTTGEIPFYGKAIPLEVIKGGRHLIFCHSKKKCDEL | 3.2 |
| 261D Seq. ID 72 | SVTVPHPNIEEVALSTTGEIPFYGKAIPLEVIKGGRHLIFCHSKKKCDEL | 15.8 |
| 261E Seq. ID 73 | TVLDQAETAGARLVVLATATPPGSVTVPHPNIEEVALSTTGEIPFYGKAIPLEVIKGGRHLIFCHSKKKCDEL | 14.9 |
| 261F Seq. ID 74 | GGAYDIIICDECHSTDATSILGIGTVLDQAETAGARLVVLATATPPGSVTVPHPNIEEVALSTTGEIPFYGKAIPLEVIKGGRHLIFCHSKKKCDEL | 21.4 |
| 279A (Pep3) Seq. ID 75 | RITITGSPITYSTYGKFLADGGCSGGAYDIIICDECHSTDATSILGIGTVLDQAETAG | 100.0 |
| 279B Seq. ID 76 | GCSGGAYDIIICDECHSTDATSILGIGTVLDQAETAG | 3.0 |
| 279E Seq. ID 77 | FLADGGCSGGAYDIIICDECHSTDATSILGIGTVLDQAETAG | 2.2 |
| | RITITGSPITYSTYGKFLADGGCSGGAYDIIICDECHSTDATSILGIGTVLDQAETAG | |

(B) Enhancement of Peptide Immunoreactivity by pH Adjustment

Although the immunoreactivities of 29 of the 30 NS-3 derived peptides, as originally synthesized and cleaved products, were marginal, the conformation of some peptides could be modulated by pH adjustment to enhance their immunoreactivity.

Peptides dissolved at 1 mg/mL in $H_2O$, pH 4, were titrated to pH 11 by addition of diluted NaOH. After 5 min at pH 11, the pH of the peptide solution was brought down to 7.0 using diluted HCl. Immunoreactivity of the peptides thus treated was compared with reactivity prior to pH adjustment (Table 4E). Two-to three- fold increases in A492 nm were seen. Some previously non-reactive serum samples were able to react with pH adjusted peptides. For instance, serum sample 1, which is non-reactive to 261C, has an absorbance of 1401 mA when tested with the corresponding pH adjusted peptide. Adjustment of pH increases the relative immunopotency of peptide 261C from 3.2% to 68.5%, compared with the standard pep3 (or 279A).

(C) Effect of Extraction Conditions after HF Cleavage on the Immunoreactivities of Peptides Peptide extraction conditions after HF cleavage were altered to test for their effect on peptide immunopotency after HF cleavage. Pep3 (or 279A) was extracted with acetic acid at pH 2, whereas pep3' was extracted with ammonium bicarbonate at pH 8. The latter extracted product showed a decrease in its reactivity in all reactive samples tested (Table 4F). The decrease ranged from 77.6% to 99.3%.

TABLE 4F

Effect of Extraction Conditions on Synthetic Peptide's Immunopotency

A492 nm (mA) by EIA

| | Pep3 Acetic Acid | Pep3' $(NH_4)_2CO_3$ | % Decrease |
|---|---|---|---|
| Blank | 0 | 0 | — |
| NRC | 1 | 1 | — |
| WRC | 565 | 59 | 89.6 |
| SRC | 2213 | 495 | 77.6 |
| #1 | 1550 | 329 | 78.8 |
| #2 | 628 | 63 | 90.0 |
| #3 | 1323 | 112 | 91.5 |
| #4 | 1019 | 7 | 99.3 |
| #5 | 1610 | 193 | 88.0 |

NRC: Negative Control
WRC: Weakly Reactive Control
SRC: Strongly Reactive Control

EXAMPLE 5

Relative (%) Immunoreactivity for NS-5 Protein Derived Synthetic Peptides by an Enzyme-Linked Immunosorbent Assay Wells of 96-well plates were coated for 1 hour at 37° C. with each of the three peptides derived from the NS-5 region of HCV (designated as pep4, pep5 and pep6). The results obtained (Table 5) show that all these peptides were immunoreactive with a unique group of 5 HCV positive sera.

TABLE 5

HCV NS-5 Protein Derived Synthetic Peptides

| Code | Amino Acid Sequence | % Relative Immunoreactivity |
|---|---|---|
| Pep4 | DPSHTAEAAGRRLARGSPPSVASSSASQLSAPSLKATCTANHDSP | 28.6 |
| Pep5 | DAELIEANLLWRQEMGGGNITRVESENKVVILDSFDPLVAEEDER | 100.0 |
| Pep6 | DPQARVAIKSLTERLTVGGPLTNSRGENCGYRRCRASRAS | 17.0 |

| Sample No. | PeP4 Seq. ID 4 | Pep5 Seq. ID 5 | Pep6 Seq. ID 6 |
|---|---|---|---|
| 1 | 0.468 | 2.942 | 0.550 |
| 2 | 0.659 | 0.370 | 0.245 |
| 3 | 0.675 | 0.616 | 0.043 |
| 4 | 0.063 | 1.316 | 0.162 |
| 5 | 0.144 | 1.783 | 0.192 |

TABLE 4E

A492 nm (mA) by EIA

| | 274B | | 275B | | 261C | | 272C | |
|---|---|---|---|---|---|---|---|---|
| | Ctrl | pH adj | Ctrl | pH adj | Ctrl | pH adj | Ctrl | pH adj |
| 1 | 628 | 1604 | 210 | 591 | 6 | 1401 | 8 | 973 |
| 2 | 148 | 466 | 37 | 159 | 5 | 499 | 74 | 255 |
| 3 | 9 | 625 | 0 | 217 | 24 | 175 | 29 | 141 |
| 4 | 464 | 1144 | 124 | 311 | 27 | 351 | 17 | 158 |

EXAMPLE 6

Detection of Antibodies to HCV By an Agglutination Based Assay

The presently claimed HCV peptides, synthesized according to the Merrifield solid phase method, can be conjugated to bovine serum albumin (BSA) by a simple crosslinking method in the presence of a low percentage of glutaraldehyde solution, or with other crosslinking reagent such as m-maleimidobenzoyl-N-hydroxysuccinimide ester (MBS).

Based on the above mentioned peptide-BSA conjugation process, conjugated peptide was absorbed onto double aldehyde fixed human O erythrocytes at pH 4.0. The peptide-conjugate coated erythrocytes were then treated with $NaBH_4$ to prevent non-specific protein binding. The peptide-conjugate coated erythrocytes were then washed with PBS and incubated with 5% normal human serum-PBS solution. These processed cells were then used in an agglutination assay for the detection of HCV antibodies in both serum and plasma specimens. The specimens were diluted 1:10 in a sample diluent buffer and an equal volume of the indicator cells was mixed with the diluted specimens. The agglutination pattern was settled within one hour; and the assay results were read by eye. Serial bleedings from three well-characterized HCV seroconversion panels were tested for antibodies to HCV in the above-described HCV passive hemagglutination assay (PHA) employing Peptide VIIIE-BSA conjugate and Peptide IIIH-BSA conjugate as the solid phase. The results were compared with the A492 and S/C of the peptide based HCV EIA (Format C, as described in Example 11) and C100 based HCV EIA (Table 6).

In brief, the PHA assay detected HCV antibodies in all three panels as early as there was an increase in A492 in the peptide based EIA (Format C). rC100 based EIA lagged behind the HCV PHA results by 4–8 weeks.

TABLE 6

Dectection of HCV Specific Antibodies from Seroconversion Panels by Various HCV Antibody Assays

| Series | Days | ALT | Format C HCV EIA S/C Ratio | C100 Based HCV EIA | HVC PHA Visual Score |
|---|---|---|---|---|---|
| A* | 0 | 40 | 0.108 | 0.03 | – |
| (Serologicals | 7 | 32 | 0.045 | 0.04 | – |
| Panel B) | 14 | 32 | 0.025 | 0.06 | ++ |
|  | 21 | 180 | 1.037 | 0.04 | ++ |
|  | 50 | 401 | 7.193 | 0.19 | ++ |
|  | 92 | — | 10.185 | 6.57 | ++ |
|  | 105 | — | 9.770 | 6.57 | ++ |
| B* | 0 | 39 | 0 | 0 | – |
| (Serologicals | 10 | 274 | 0.058 | 0 | – |
| Panel A) | 14 | 346 | 0.128 | 0 | – |
|  | 30 | 1175 | 7.835 | 6.5 | ++ |
|  | 51 | 430 | 7.811 | 6.5 | ++ |
| C* | 0 | 63 | 0.115 | 0.04 | – |
| (Serologicals | 2 | 81 | 1.607 | 0.04 | ++ |
| Panel C) | 9 | 183 | 2.506 | 0.02 | +++ |
|  | 29 | 563 | 9.827 | 6.57 | +++ |
|  | 57 | 436 | 10.630 | 6.57 | +++ |

*Case presented is a plasma donor from a commercial source. Day 0 designates first sample in the series and does not correspond to date of exposure.

EXAMPLE 7

Detection of Antibodies to HCV by an Agglutination Assay Utilizing as the Solid Phase Immunosorbent Latex Particles Coated with HCV Peptide Using the peptide-BSA conjugation process mentioned in the previous example, conjugated peptide VIIIE-BSA, was absorbed to latex particles (0.4µ size) at pH 9.5. The peptide-conjugate coated latex particles were then treated with BSA to prevent nonspecific protein binding. These coated latex particles were then used in an agglutination assay for the detection of HCV antibodies. The specimens were mixed in a ratio of 1:1 with the latex solution (0.5%). The agglutination pattern was complete in a period of 15 min. Assay results were read by eye and by microscopic examination. The results of serial dilution samples from a well characterized anti-HCV positive plasma sample are summarized in Table 7. A coating concentration of 0.3 mg/mL was found to give optimal sensitivity for antibody detection. As a control for specificity, pooled plasma specimens from normal donors were tested in the peptide VIII-BSA conjugate latex assay and were found clearly negative.

TABLE 7

Rapid Detection of HCV Antibodies using VIIIE-BSA Sensitized Latex Particles and Scoring for Visual Agglutination Pattern

| HCV Positive Control Dilution | Degree of Agglutination | | | |
|---|---|---|---|---|
|  | VIIIE-BSA 2.4 mg/mL | Latex Particle 1.2 mg/mL | Coating 0.6 mg/mL | Concentration 0.3 mg/mL |
| 1:1 | 4+ | 4+ | 4+ | 4+ |
| 1:2 | 4+ | 4+ | 4+ | 4+ |
| 1:5 | 4+ | 4+ | 4+ | 4+ |
| 1:10 | 4+ | 4+ | 4+ | 4+ |
| 1:20 | 3+ | 4+ | 4+ | 4+ |
| 1:40 | 2+ | 3+ | 4+ | 4+ |
| 1:80 | +/– | – | + | 3+ |
| 1:160 | – | – | – | + |
| 1:320 | – | – | – | +/– |
| 1:640 | – | – | – | +/– |
| NP 1:1 | – | – | – | – |

NP: Pooled Normal Plasma

EXAMPLE 8

Synthesis of Octameric HCV Peptide Antigens as Key Components of Immunogens/Vaccines The use of a limited sequential propagation of a trifunctional amino acid (or similar analogues) to form a core that serves as a low molecular weight matrix is the basic underlying principle for the formation of a radially branching multimeric peptide antigen system. The trifunctional amino acid, Boc-Lys(Boc), or di-(Boc)-Lys is most suitable since both $N^\alpha$-and $N^\epsilon$-amino acid groups are available as reactive ends. Thus, sequential propagation of di-(Boc)-Lys will generate $2^n$ reactive ends. For example, the first level coupling of di-(Boc)-Lys will produce two reactive amino ends as a bivalent peptide antigen. Sequential generations of a second, third, and fourth step with di-(Boc)-Lys will therefore generate tetravalent, octavalent, and hexadecavalent peptide antigens respectively. As an example, an octameric HCV peptide immunogen with a structure of [Gln-Gly-Trp-Gly-Pro-Ile-Ser-Tyr-Ala-Asn-Gly-Ser-Gly-Pro-Asp-Gln-Arg-Pro-Tyr-Cys-Trp-His-Tyr-Pro-Pro-Lys-Pro-Cys-Gly-Ile-Val-Pro-Ala-Lys-Ser-Val-Cys-Gly-Pro-Val-Tyr-Cys]$_8$-Lys$_4$-Lys$_2$-Lys was synthesized as a prototype immunogen used in our immunization of guinea pigs. This octameric antigen contains a small heptalysyl core (<20%) and the bulk (>80%) is formed by a high density of uniform peptide-antigen layered around the core matrix. This design differs from the conventional peptide-carrier conjugate which contains a large protein carrier such as PPD or KLH and a low density of peptide antigens randomly distributed on the protein carrier surface in an unidentified form.

For the synthesis of octameric HCV peptide immunogen, a combination of Boc-amino acid resin-bound benzhydrylamide and tBoc-chemistry was used. An octameric heptalysyl core resin was prepared by coupling di-t-Boc Lys onto an extra low loading 0.14 mmole/g MBHA (4-methyl benzhydrylamine) resin on a Biosearch 9500 instrument. During each of the two coupling cycles, di-(Boc)-Lys was used for single coupling followed by two capping reactions (with 0.3M acetylimidazole in DMF dimethylformamide).

After two additional di-(Boc)-Lys couplings onto the first di-(NH$_2$) Lys-resin, the substitution level of synthetic octameric resin was determined by ninhydrin test and found to have an appropriate level of —NH$_2$ groups, as calculated based on a theoretical coupling yield, and was used thereafter for the synthesis of octameric peptide antigens each with a predefined amino acid sequence according to the standard t-Boc chemistry.

Acid-labile tert-butyloxycarbonyl (t-Boc) was used for the protection of N-α amino acid. The following functional side-chain protecting groups were used: O-benzyl for Thr, Ser, Glu and Tyr; N$^G$-tosyl for Arg; BOM(i.e. Boc-N$^{im}$-Benzyloxymethyl-) for His; N$^ε$-dichlorobenzyloxycarbonyl for Lys; S-4-methylbenzyl-for Cys; O-cyclohexyl for Asp and CHO for Trp. Successive amino acids were added as dictated by the sequence. The resultant octameric peptidyl resin was cleaved by anhydrous HF [0° C. for 1 hr in the presence of 10% (v/v) anisole]. The released octameric antigen was extracted by acetic acid, after two cycles of ether washings of the cleaved peptidyl resin, and lyophilized to dryness so as to be ready for use as an immunogen. A computer-generated picture of such an octameric immunogen is shown in FIG. 1.

EXAMPLE 9

Relative (%) Immunoreactivity for Envelope/NS-1 Protein Derived Synthetic Peptides by an Enzyme-linked Immunosorbent Assay Wells of 96-well plates were coated for 1 hour at 37° C. with each of the 21 peptides (designated as 255 A-C; 244 A,B; 254 A-C; 248 A-C; 247 A-E and 246 A-E, synthesized with sequences derived from the envelope/NS-1 region of HCV, at 5 ug/mL at 100 uL per well in 10 mM NaHCO$_3$ buffer, pH 9.5. The immunoreactivity of each peptide was measured by an 8 member HCV serum panel (Panel I). All 21 peptides were lacking in immunoreactivity on this standard screening HCV panel. However, peptide 254B was found to have some weak reactivity with one panel member, and upon further testing it also reacted strongly with a sample derived from an anti-HCV positive (positive with peptides VIIIE and IIH) plasmapheresis donor with elevated (100 i.u./L) alanine aminotransferase (ALT) enzyme activity. To select a panel of samples with reactivity to peptides from the envelope/NS-1 region, 97 such samples from anti-HCV positive plasmapheresis donors with elevated ALT levels were tested with peptide 254B. One sample had an absorbance of 3.214, and a second sample, 2.184. 17 samples with the greatest reactivity with peptide 254B were chosen to form a third panel (Panel III) to screen for the immunoreactivity of the other 20 peptides from the envelope/NS-1 region. The relative (%) immunoreactivity, using peptide 254B as a standard, is given in Table 8a. The individual absorbance values of each of the 17 samples on the four peptides with the greatest reactivity, i.e. 255C (pep7), 254B (pep8), 247B (pep9), and 246D (pep10), are listed in Table 8b.

Since a unique immunoreactivity pattern with panel III members is observed for each of the four peptides (see the boxed value), all four peptides or their analogues are therefore found to be useful as antigens for the development of immunoassays designed for the detection and screening for antibodies to HCV, particularly to the envelope/NS-1 associated proteins. This "unique" yet "complementary" immunoreactivity pattern conferred by the four peptides as illustrated in Table 8b further demonstrates that the utility of the peptides as antigens for HCV antibody detection, as immunogens for the development of antibodies to HCV envelope/NS-1 protein, and as vaccines for the protection of HCV infection.

Since all four peptides (pep7, pep8, pep9, and pep10) are derived from the variable regions of the HCV envelope/NS-1 proteins, examples of substitution analogues for these four peptides are given in Table 8c based on the amino acid sequence (single letter code) information derived from three different HCV strains.

In addition to screening on Panel III samples, the envelope/NS-1 peptides were also tested against samples from plasmapheresis donors who had elevated ALT levels but were non-reactive on the HCV from the core (e.g. peptide VIIIE) and NS-4 (e.g. peptide IIH) regions screening EIA. Six of these samples, which may represent early seroconversion samples, were reactive on one or more envelope/NS-1 peptide (Table 8d). The absorbance values on these HCV EIA nonreactive samples are lower than the values found for Panel III samples. In the case of Pep7 and Pep10, their shorter segments, 225B and 246C, respectively, gave greater immunoreactivity, in contrast to the performance on Panel III.

TABLE 8a

Synthetic Peptides with their Amino Acid Sequences Derived from the HCV Envelope/NS-1 Protein Region

| ID | Sequence | % Relative Immunoreactivity |
|---|---|---|
| 255A Seq. ID 79 | CLTVPASAYQVRNSTGLYHVTNDCPNSSIVYEAHDAILHTPGCPCVREGNVSRCWVAMTPTVATRDGKLPATQLRRIDLLVGSAILC | 9.8 |
| 255B Seq. ID 80 | TNDCPNSSIVYEAHDAILHTPGCPCVREGNVSRC | 18.7 |
| 255C (Pep7) Seq. ID 7 | VRNSTGLYHVTNDCPNSSIVYEAHDAILHTPGCPCVREGNVSRC | 51.4 |
|

TABLE 8a-continued

Synthetic Peptides with their Amino Acid Sequences Derived from the HCV Envelope/NS-1 Protein Region

| | | % Relative Immuno-reactivity |
|---|---|---|
| ID 9 | | |
| 247C<br>Seq.<br>ID 88 | VLVVLLLFAGVDAETIVSGGQAARAMSGLVSLFTPGAKQNIQLIN | 21.9 |
| 247D<br>Seq.<br>ID 89 | YFSMVGNWAKVLVVLLLFAGVDAETIVSGGQAARAMSGLVSLFTPGAKQNIQLIN | 22.7 |
| 247E<br>Seq.<br>ID 90 | LAGIAYFSMVGNWAKVLVVLLLFAGVDAETIVSGGQAARAMSGLVSLFTPGAKQNIQLIN | 26.5 |
| 246A<br>Seq.<br>ID 91 | TGWLAGLIYQHKFNSSGCPERLASC | 37.5 |
| 246B<br>Seq.<br>ID 92 | CNESLNTGWLAGLIYQHKFNSSGCPERLASC | 19.8 |
| 246C<br>Seq.<br>ID 93 | INSTALNCNESLNTGWLAGLIYQHKFNSSGCPERLASC | 97.6 |
| 246D<br>(Pep10)<br>Seq.<br>ID 93 | WHINSTALNCNESLNTGWLAGLIYQHKFNSSGCPERLASC | 98.6 |
| 246E<br>Seq.<br>ID 94 | KQNIQLINTNGSWHINSTALNCNESLNTGWLAGLIYQHKFNSSGCPERLASC | 10.5 |

TABLE 8b

Absorbance of Envelope/NS-1 Peptides on Selected Anti-HCV Positive Samples with Elevated ALT Levels

| Sample | Pep7 | Pep8 | Pep9 | Pep10 |
|---|---|---|---|---|
| 1 | [1.520] | 0.475 | 0.335 | 1.085 |
| 2 | 0.017 | [0.612] | 0.009 | 0.068 |
| 3 | 0.235 | [0.774] | 0.341 | 0.090 |
| 4 | 0.066 | 0.279 | 0.268 | [1.038] |
| 5 | 0.711 | 0.076 | [1.412] | 0.077 |
| 6 | 0.106 | 0.058 | 0.027 | [1.428] |
| 7 | 0.784 | [2.184] | 0.241 | [3.468] |
| 8 | 0.037 | 0.120 | 0.055 | [2.992] |
| 9 | 0.019 | [1.597] | 0.177 | 0.334 |
| 10 | 0.313 | [3.214] | [2.564] | 1.488 |
| 11 | 0.035 | 0.025 | [0.763] | 0.045 |
| 12 | [2.132] | 1.497 | 0.160 | 0.408 |
| 13 | [2.266] | 1.573 | 0.129 | 0.451 |
| 14 | 0.047 | [1.155] | 0.170 | 0.037 |
| 15 | 0.012 | 0.053 | 0.030 | [2.280] |
| 16 | 0.064 | [2.200] | 0.039 | 0.810 |
| 17 | 0.077 | [0.541] | 0.069 | 0.111 |

TABLE 8c

PEP7 (255C)
(J-1):  C L T V P A S A Y Q V R N S T G L Y H V T N D C P N S S I V Y E A H D A I L H T P G C V F C V R E G N V S R C
(J-4):  C L T I P A S A Y E V R N V S G I Y H V T N D C S N S S I V Y E A A D M I M H T P G C V F C V R E D N S S R C
(HCV-J): C L T I P A S A Y E V R N V S G I Y H V T N D C S N S S I V Y E A A D M I M H T P G C V F C V R E S N F S R C

PEP8 (254B)
(J-1):  F T F S P R R H W T T Q C N C S I Y P G H I T G H R M A W D M M M M N W S P T A
(J-4):  F T F S P R R H E T V Q D C N C S I Y P G H L S G H R M A W D M M M M N W S P T T
(HCV-J): F T F S P R R Y E T V Q D C N C S I Y P G H V S G H R M A W D M M M M N W S P T T

PEP9 (247B)
(J-1):  V D A E T I V S G G Q A A R A M S G L V S L F T P G A K Q N I Q L I N
(J-4):  V D A E T Y T S G G A A S H T T S T L A S L F S P G A S Q R I Q L V N
(HCV-J): V D G H T H V T G G R V A S S T Q S L V S W L S Q G P S Q K I Q L V N

PEP10 (246D)
(J-1):  W H I N S T A L N C N E S L N T G W L A G L I Y Q H K F N S S G C P E R L A S C
(J-4):  W H I N R T A L N C N D S L H T G P L A A L F Y T H R F N S S G C P E R M A S C
(HCV-J): W H I N R T A L N C N D S L Q T G F I A A L F P A H R F N A S G C P E R M A S C

Examples of substitution analogues of pep7, pep8, pep9 and pep10 are given above based on the amino acid sequence (single letters code) information derived from three representative HCV strains (J-1, J-4 and J). The shared amino acid residues are boxed for purpose of comparison.

TABLE 8d

Absorbance of Envelope/NS-1 Peptides on Selected Samples Nonreactive on HCV Core (VIIIE) and NS-4 (IIH) Peptides

| Sample | 255B | 255C (Pep7) | 254B (Pep8) | 246C | 246D (Pep10) |
|---|---|---|---|---|---|
| 1 | 0.344 | 0.098 | 0.173 | 0.240 | 0.068 |
| 2 | 0.419 | 0.346 | 0.015 | 0.015 | 0.028 |
| 3 | 0.403 | 0.300 | 0.0111 | 0.023 | 0.029 |
| 4 | 0.021 | 0.021 | 0.222 | 0.046 | 0.049 |
| 5 | 0.300 | 0.231 | 0.014 | 0.009 | 0.009 |
| 6 | 0.012 | 0.017 | 0.044 | 0.402 | 0.102 |

EXAMPLE 10

Synthesis of Octameric HCV Envelope/NS-1 Peptide Antigens as Key Components of Immunogens/Vaccines Four octameric HCV envelope/NS-1 peptide immunogens with a structure of [Cys-Leu-Thr-Val-Pro-Ala-Ser-Ala-Tyr-Gln-Val-Arg-Asn-Ser-Thr-Gly-Leu-Tyr-His-Val-Thr-Asn-Asp-Cys-Pro-Asn-Ser-Ser-Ile-Val-Tyr-Glu-Ala-His-Asp-Ala-Ile-Leu-His-Thr-Pro-Gly-Cys-Val-Pro-Cys-Val-Arg-Glu-Gly-Asn-Val-Ser-Arg-Cys]$_8$Lys$_4$Lys$_2$Lys (octameric pep7); [Phe-Thr-Phe-Ser-Pro-Arg-Arg-His-Trp-Thr-Thr-Gln-Gly-Cys-Asn-Cys-Ser-Ile-Tyr-Pro-Gly-His-Ile-Thr-Gly-His-Arg-Met-Ala-Trp-Asp-Met-Met-Met-Asn-Trp-Ser-Pro-Thr-Ala]$_8$ Lys$_4$Lys$_2$Lys (octameric pep8); [Val-Asp-Ala-Glu-Thr-Ile-Val-Ser-Gly-Gly-Gln-Ala-Ala-Arg-Ala-Met-Ser-Gly-Leu-Val-Ser-Leu-Phe-Thr-Pro-Gly-Ala-Lys-Gln-Asn-Ile-Gln-Leu-Ile-Asn]$_8$Lys$_4$Lys$_2$Lys (octameric pep9) and [Trp-His-Ile-Asn-Ser-Thr-Ala-Leu-Asn-Cys-Asn-Glu-Ser-Leu-Asn-Thr-Gly-Trp-Leu-Ala-Gly-Leu-Ile-Tyr-Gln-His-Lys-Phe-Asn-Ser-Ser-Gly-Cys-Pro-Glu-Arg-Leu-Ala-Ser-Cys]$_8$Lys$_4$Lys$_2$Lys (octameric pep10), are synthesized respectively according to a general chemical synthesis procedure described in Example 8 and used as immunogens in our immunization of guinea pigs and chimpanzees.

These octameric peptides are injected as a mixture into healthy, naive animals both intradermally and subcutaneously at a dosage of 25 ug per mixture per kg body weight using 2% alum as an adjuvant. After the initial immunization, these animals are boosted at the same dose once per month for a period of four months. The animals are bled monthly and the collected immune sera are monitored for their anti-HCV envelope/NS-1 immunoreactivity. Six months after the last boost, the immunized chimpanzees are subsequently challenged by experimental inoculation with various dosages (e.g. 50 mL) of a proven infectious Factor VIII concentrate known to contain HCV so as to evaluate the efficacy in using a mixture of these octameric envelope/NS-1 peptides as a vaccine for the prevention of HCV infection.

EXAMPLE 11

Detection of Antibodies to HCV by a Peptide Based Enzyme Immunoassay (EIA) Using Format C A total of 221 well-characterized clinical specimens categorized into four groups, (a) to (d), were tested on a representative HCV peptide based EIA with the plates coated with a mixture of peptides IIH, V and VIIIE at 5, 3 and 2 ug/mL respectively at 100 uL per well (Format C), containing both the HCV core and nonstructural peptides as shown in Table B.

TABLE B

| Clinical Group | n | % positive for HCV antibodies |
|---|---|---|
| (a) AIDS/ARC patients | 63 | 55.6 |
| (b) HBsAg positive individuals | 50 | 42.0 |
| (c) HBc antibody positive antibodies | 22 | 22.7 |
| (d) Individuals with elevated (>100 i.u./L) alanine amino transferase (ALT) enzyme activity | 86 | 91.5 |

EXAMPLE 12

Detection of Antibodies to HCV by Peptide Based HCV EIA Using Formats 1 to 6

The following five groups of serum specimens:

(a) Plasmapheresis donors with elevated (>100 i.u./L) alanine aminotransferase (ALT) enzyme activity (n=30);

(b) Blood donors with elevated (>45 i.u./L) ALT enzyme activity (n=15);

(c) Chronic NANBH patients (n=30);

(d) Other viral infections (n=11);

(e) Autoimmune disease patients (n=9);

were analyzed on representative HCV peptide based EIA kits according to the present invention, with the plates coated at 100 uL per well either with:

(i) Format 1: peptides VIII E, II H and pep11 at 0.5, 3 and 1 µg/mL each;

(ii) Format 2: peptides VIII E and pep11 at 0.5 and 1 µg/mL each;

(iii) Format 3: peptides VIII E, pep11 and pep8 at 0.5, 1 and 10 µg/mL each;

(iv) Format 4: peptides VIII E and pep8 at 0.5 and 10 µg/mL each;

(v) Format 5: peptides VIII E, pep11 and pep12 at 0.5, 1 and 2 µg/mL each;

(vi) or Format 6: peptides VIII E and pep12 at 0.5 and 2 µg/mL each.

These kits represent core, NS-4 and NS-5 (Format 1), core and NS-5 (Formats 2, 5 and 6), core, NS-5 and env (Format 3) and core and env (Format 4).

The results of testing these 95 well characterized samples on Formats 1 through 6 are presented in Table 9. The results indicate that (30/30) of the samples in group (a) were reactive by Formats 1, 2 and 3; 90% (27/30) reactive by Format 4 and 97% (29/30) reactive by Formats 5 and 6. All samples in groups (b) and (c) were positive on all 6 formats. Groups (a), (b) and (c) were shown to be reactive by Format C described in Example 11.

Three samples in group (d) were reactive by Formats 1 to 4. In contrast, these samples were indicated as negative by Format C. Serum samples "86" and "124" apparently responded to the presence of pep11, and serum sample "VZV2500" was indicated as positive by the presence of pep8 in Formats 4 and 5.

All serum samples in group (c) were negative on all formats, including Format C.

TABLE 9

Antibody to HCV Detected By Peptide Based EIA Kits (Absorbance 492 nm)

| Sample ID | | Format 1 | Format 2 | Format 3 | Format 4 | Format 5 | Format 6 |
|---|---|---|---|---|---|---|---|
| NRC | | 0.065 | 0.075 | 0.056 | 0.061 | 0.060 | 0.019 |
| WRC | | 0.650 | 0.454 | 0.953 | 0.967 | 0.403 | 0.340 |
| SRC | | 2.183 | 1.791 | 2.580 | 2.635 | 1.589 | 1.331 |
| a. Plasmapheresis, ALT > 100 i.u.L | | | | | | | |
| 1 | −13 | 3.166 | 3.419 | 3.255 | 3.371 | 3.291 | 3.255 |
|  | −27 | 1.555 | 1.548 | 1.980 | 2.904 | 1.152 | 0.881 |
|  | −31 | 3.479 | 3.144 | 3.220 | 2.332 | 3.319 | 2.665 |
|  | −32 | 3.001 | 3.035 | 3.112 | 2.691 | 3.076 | 2.986 |
|  | −39 | 3.063 | 3.041 | 3.361 | 2.886 | 3.190 | 3.038 |
|  | −42 | 3.198 | 3.201 | 3.050 | 3.227 | 3.230 | 3.118 |
|  | −47 | 3.479 | 3.110 | 3.251 | 3.201 | 3.229 | 3.068 |
|  | −48 | 3.142 | 2.795 | 3.116 | 2.934 | 3.076 | 2.725 |
|  | −49 | 3.417 | 3.291 | 3.525 | 3.451 | 3.195 | 3.592 |
|  | −52 | 3.263 | 3.329 | 3.202 | 0.120 | 3.262 | 3.453 |
|  | −53 | 3.225 | 3.145 | 3.096 | 0.062 | 3.358 | 3.097 |
|  | −54 | 3.271 | 3.018 | 3.267 | 0.153 | 3.073 | 3.211 |
| 2 | −4 | 1.012 | 0.881 | 1.542 | 1.767 | 0.807 | 0.745 |
|  | −6 | 3.229 | 2.964 | 3.169 | 3.052 | 3.076 | 2.897 |
|  | −9 | 2.691 | 2.416 | 2.766 | 2.967 | 2.119 | 1.844 |
|  | −26 | 3.222 | 3.055 | 3.095 | 3.167 | 3.195 | 2.951 |
|  | −32 | 3.226 | 3.372 | 3.368 | 3.194 | 3.496 | 3.417 |
|  | −33 | 3.151 | 2.918 | 3.147 | 3.027 | 3.108 | 3.129 |
|  | −34 | 3.059 | 3.021 | 3.143 | 3.167 | 3.145 | 3.320 |
|  | −38 | 3.241 | 3.116 | 2.967 | 3.055 | 3.213 | 3.137 |
|  | −41 | 2.964 | 2.593 | 2.841 | 2.964 | 2.469 | 2.252 |
|  | −43 | 3.146 | 2.092 | 2.541 | 2.627 | 1.999 | 1.920 |
|  | −46 | 2.927 | 2.818 | 2.998 | 2.983 | 2.556 | 2.415 |
|  | −58 | 3.285 | 3.444 | 3.218 | 3.191 | 3.355 | 3.095 |
|  | −60 | 3.094 | 2.975 | 3.113 | 3.167 | 2.683 | 2.640 |
|  | −61 | 2.784 | 2.345 | 2.501 | 2.751 | 2.007 | 2.212 |
|  | −62 | 3.320 | 3.076 | 3.095 | 3.076 | 3.003 | 2.787 |
|  | −77 | 0.815 | 0.682 | 1.096 | 0.418 | 0.164 | 0.152 |
|  | −82 | 3.020 | 2.982 | 1.826 | 3.001 | 3.032 | 2.820 |
|  | −83 | 3.076 | 2.914 | 3.049 | 2.996 | 2.928 | 2.808 |
| b. Elevated ALT blood donors (ALT > i.u/./L) | | | | | | | |
| ALT | −1 | 3.017 | 3.035 | 3.116 | 3.165 | 3.167 | 2.920 |
|  | −2 | 3.256 | 3.166 | 3.165 | 2.974 | 3.292 | 3.091 |
|  | −3 | 3.153 | 3.328 | 3.291 | 3.105 | 3.203 | 3.230 |
|  | −4 | 2.969 | 2.894 | 3.096 | 3.144 | 2.880 | 2.866 |
|  | −5 | 3.073 | 2.956 | 2.968 | 2.952 | 3.376 | 2.985 |
|  | −7 | 3.218 | 3.020 | 3.157 | 2.980 | 2.951 | 3.060 |
|  | −8 | 3.074 | 2.930 | 3.094 | 3.197 | 3.121 | 3.012 |
|  | −10 | 3.479 | 3.228 | 3.226 | 3.109 | 3.432 | 3.952 |
|  | −11 | 3.398 | 3.283 | 3.140 | 3.035 | 3.285 | 3.222 |
|  | −53 | 3.330 | 3.029 | 3.253 | 3.290 | 2.974 | 3.070 |
|  | −56 | 3.151 | 3.086 | 3.176 | 3.202 | 3.107 | 3.085 |
|  | −69 | 3.021 | 3.170 | 3.167 | 3.318 | 3.019 | 2.831 |
|  | −70 | 3.074 | 3.035 | 2.951 | 3.073 | 3.054 | 3.184 |
|  | −71 | 2.985 | 2.901 | 3.080 | 3.039 | 2.902 | 2.900 |
|  | −82 | 3.230 | 3.120 | 3.085 | 2.977 | 3.298 | 3.096 |
| c. Chronic NANBH | | | | | | | |
| N | −2 | 3.320 | 3.052 | 2.981 | 3.283 | 3.032 | 2.999 |
|  | −3 | 3.285 | 3.036 | 3.095 | 3.167 | 3.077 | 3.094 |
|  | −4 | 3.117 | 3.469 | 3.590 | 3.291 | 2.259 | 3.141 |
|  | −7 | 3.027 | 3.008 | 3.061 | 3.065 | 2.962 | 2.806 |
|  | −8 | 3.285 | 3.146 | 3.117 | 3.194 | 3.122 | 3.195 |
|  | −9 | 2.886 | 3.001 | 3.072 | 2.985 | 2.848 | 2.859 |
|  | −10 | 2.606 | 2.268 | 2.027 | 0.423 | 2.338 | 1.104 |
|  | −14 | 3.054 | 2.808 | 2.856 | 2.995 | 2.341 | 2.041 |
|  | −23 | 3.228 | 3.050 | 3.067 | 3.225 | 3.152 | 3.109 |
|  | −25 | 3.891 | 2.462 | 3.190 | 3.165 | 1.982 | 2.091 |
|  | −27 | 3.194 | 2.926 | 3.165 | 3.029 | 3.143 | 3.168 |
|  | −28 | 3.027 | 3.106 | 3.259 | 3.175 | 3.176 | 3.202 |
|  | −34 | 3.057 | 3.037 | 3.035 | 3.144 | 2.907 | 2.892 |
|  | −36 | 3.304 | 3.213 | 3.000 | 3.033 | 3.075 | 3.115 |
|  | −41 | 3.217 | 3.283 | 3.039 | 3.248 | 3.290 | 3.249 |
|  | −42 | 2.997 | 2.858 | 3.196 | 3.094 | 3.097 | 2.805 |
|  | −44 | 3.391 | 3.477 | 3.350 | 3.254 | 3.353 | 3.387 |
|  | −45 | 3.318 | 3.096 | 2.964 | 3.250 | 3.319 | 3.036 |
|  | −49 | 3.292 | 3.371 | 3.416 | 3.255 | 3.292 | 3.370 |
|  | −54 | 3.329 | 3.294 | 3.105 | 3.105 | 3.177 | 3.203 |
|  | −57 | 3.197 | 3.169 | 3.221 | 3.141 | 3.120 | 3.018 |
|  | −60 | 3.115 | 3.035 | 3.090 | 3.072 | 3.096 | 2.873 |
|  | −65 | 2.020 | 1.816 | 1.898 | 2.376 | 1.133 | 1.284 |
|  | −67 | 2.265 | 1.776 | 2.356 | 2.396 | 1.319 | 0.911 |
|  | −68 | 3.178 | 3.177 | 3.200 | 3.176 | 3.530 | 3.087 |
|  | −69 | 3.222 | 3.167 | 3.165 | 3.283 | 3.399 | 3.097 |
|  | −77 | 1.438 | 1.346 | 2.548 | 2.397 | 1.055 | 1.071 |
|  | −78 | 2.457 | 2.038 | 2.251 | 2.300 | 1.642 | 1.494 |
|  | −79 | 3.225 | 3.197 | 3.076 | 3.142 | 3.224 | 3.169 |
|  | −80 | 3.138 | 3.074 | 3.135 | 3.054 | 3.137 | 2.896 |
| d. Other Viral Infections | | | | | | | |
| HAV | −86 | 0.558 | 0.316 | 0.607 | 0.054 | 0.037 | 0.014 |
|  | −88 | 0.018 | 0.021 | 0.062 | 0.054 | 0.014 | 0.018 |
|  | −92 | 0.045 | 0.061 | 0.058 | 0.050 | 0.043 | 0.007 |
|  | −120 | 0.057 | 0.076 | 0.051 | 0.032 | 0.051 | 0.026 |
|  | −121 | 0.052 | 0.138 | 0.094 | 0.065 | 0.072 | 0.026 |
|  | −124 | 0.816 | 1.178 | 0.622 | 0.062 | 1.082 | 0.017 |
|  | −125 | 0.014 | 0.016 | 0.050 | 0.031 | 0.012 | 0.010 |
|  | −126 | 0.105 | 0.134 | 0.109 | 0.081 | 0.117 | 0.068 |
| EBV | −2331 | 0.021 | 0.021 | 0.023 | 0.020 | 0.012 | 0.012 |
| VZV-M002 | | 0.035 | 0.030 | 0.154 | 0.108 | 0.025 | 0.012 |
| VZV | −2500 | 0.090 | 0.138 | 0.976 | 0.923 | 0.084 | 0.032 |
| e. Autoimmune | | | | | | | |
|  | −209 | 0.102 | 0.079 | 0.117 | 0.097 | 0.066 | 0.028 |
|  | −210 | 0.002 | 0.003 | 0.018 | 0.011 | 0.002 | 0.005 |
|  | −211 | 0.016 | 0.019 | 0.134 | 0.168 | 0.022 | 0.016 |
|  | −212 | 0.016 | 0.020 | 0.075 | 0.080 | 0.019 | 0.006 |
|  | −213 | 0.008 | 0.009 | 0.055 | 0.076 | 0.005 | 0.002 |
|  | −215 | 0.118 | 0.095 | 0.226 | 0.282 | 0.093 | 0.060 |
|  | −216 | 0.039 | 0.037 | 0.100 | 0.105 | 0.042 | 0.022 |
|  | −217 | 0.019 | 0.021 | 0.068 | 0.056 | 0.023 | 0.012 |
|  | −218 | 0.032 | 0.022 | 0.110 | 0.086 | 0.059 | 0.031 |

EXAMPLE 13

Comparison of Test Results Using the Six Peptide Based HCV EIA Formats (1–6) on Random Blood Donors Random blood donor samples (n=100) were tested by Formats 1 to 6. All 100 samples were negative on Formats 2, 5 and 6. Sample 14 had an absorbance of 0.680 on Format 1, and sample 34 had an absorbance of 0.601 and 0.551 on Formats 3 and 4, respectively. For the calculation of mean absorbance and standard deviation, absorbance values >0.500 were omitted from analysis. Table 10 lists the mean absorbance and standard deviation of the 100 samples on Formats 1–6.

TABLE 10

Mean Absorbance (A492 nm) ± SD of 100 Random Blood Donors

|  | Format 1 | Format 2 | Format 3 | Format 4 | Format 5 | Format 6 |
|---|---|---|---|---|---|---|
| Mean | 0.040 | 0.035. | 0.068 | 0.061 | 0.030 | 0.017 |
| S.D. | 0.036 | 0.029 | 0.046 | 0.046 | 0.039 | 0.032 |

EXAMPLE 14

Peptide Analogues from HCV Variant Strains for Subtyping HCV-Reactive Sera

Immunoreactive peptides pep7, pep8, pep9 and pep19 derived from the ENV and NS-1 regions, and their analogues with sequences taken from HCV strains HC-J1, CDC/HCV 1, H, HC-J4, HCV-JH, HCV-J, BK, HC-J6 and HC-J7 are synthesized to have the amino acid sequences according to Table 11. The immunoreactive peptides are coated at 5 µg/mL at 100 uL per well in wells of microtiter plates and are used to assay HCV positive sera from Taiwan, Japan, Europe, Australia and North America to classify their HCV reactivity into subtypes e.g., HCV-J1, HC-J4, HC-J6 and HC-J7. These peptides derived from hypervariable regions of HCV are useful to distinguish the subtypes of HCV responsible for the infection.

260A–260C, 309A–309C, 310A–310C, 311A–311C, 312A–312C and 314A–314C) synthesized with sequences derived from the NS-5 region, at 5 µg/mL at 100 µL per well in 10 mM NaHCO₃ buffer, pH 9.5. The immunoreactivity of each peptide was measured by an 8 member HCV serum panel (Panel I). The peptide with the greatest immunoreactivity was pep11, designated 309C in Table 12. When the immunoreactivity of pep11 was used as a standard to cal-

TABLE 11

Immunoreactive Pep7, Pep8, Pep 9 and Pep19 and Their Substitution Analogues Derived from the HCV ENV/NS-1 Regions (Pep7, 255C, aa 184–238)
| | | |
|---|---|---|
| HV-J1 | Seq. ID 7 | CLTVPASAYQVRNSTGLYHVTNDCPNSSIVYEAHDAILHTPGCVPCVREGNVSRC |
| HCV1 | Seq. ID 111 | --------------------------------A------------------A--- |
| HCV-H | Seq. ID 112 | --------------S-------------------A------------------A--- |
| HC-J4 | Seq. ID 113 | ---I-----E---VS-I--------S----------A-M-M------------D-S--- |
| HCV-JH | Seq. ID 119 | ---I-----E---VS-I--------S----------A-V-M-A----------N-S--- |
| HCV-J | Seq. ID 115 | ---I-----E---VS-I--------S----------A-M-M------------S-F--- |
| HCV-BK | Seq. ID 116 | ---T-----E-H-VS-I--------S-A------A-L-M--------------S--- |
| HCV-J6 | Seq. ID 117 | -I-T-V--AE-K-ISTG-M-----T-D--TWQLQA-V--V------EKV--T--- |
| HCV-J7 | Seq. ID 118 | -V---V--VE---ISSS-YA----S-N--TWQLTN-V--L------ENDNGTL-- |

(Pep8, 254B, aa 291–330)
| | | |
|---|---|---|
| HC-J1 | Seq. ID 8 | FTFSPRRHWTTQGCNCSIYPGHITGHRMAWDMMMNWSPTA |
| HCV1 | Seq. ID 119 | ----------------------------------------T |
| HCV-H | Seq. ID 120 | ------------D--------------------------- |
| HC-J4 | Seq. ID 121 | ---------E-V-D----------LS----------------T |
| HCV-JH | Seq. ID 122 | ---------E-V-D----------VS---------------- |
| HCV-J | Seq. ID 123 | --------YE-V-D----------VS----------------T |
| HCV-BK | Seq. ID 124 | ---------V-L-D----------VS----------------T |
| HCV-J6 | Seq. ID 125 | -IV--QH--FV-D---------T-------------------- |
| HCV-J7 | Seq. ID 126 | -II--E--NF--E------Q--------------L------L |

(Pep9, 247B, aa 381–415)
| | | |
|---|---|---|
| HC-J1 | Seq. ID 9 | VDAETIVSGGQAARAMSGLVSLFTPGAKQNIQLIN |
| HCV-J | Seq. ID 127 | --GH-H-T--RV-SSTQS---WLSQ-PS-K---V- |
| HCV-BK | Seq. ID 128 | --GD-H-T--AQ-KTTNR---M-AS-PS-K----- |

(Peptide 19, 244B, aa 229–272)
| | | |
|---|---|---|
| HC-J1 | Seq. ID 19 | CVREGNVSRCWVAMTPTVATRDGKLPATQLRRHIDLLVGSATLC |
| HCV1 | Seq. ID 129 | ------A------------------------------------- |
| HCV-H | Seq. ID 130 | ------A-------V--------------T--------------- |
| HC-J4 | Seq. ID 131 | ----D-S------L---L-A-NASV-T-TI---V------A-AF- |
| HCV-JH | Seq. ID 132 | ----N-S------L---L-A-NASV-T-T----V------T-AF- |
| HCV-J | Seq. ID 133 | ----S-F------L---L-A-NSSI-T-TI---V------A-A-- |
| HCV-BK | Seq. ID 134 | ------S------L---L-A-NVTI-T-TI---V------A-AF- |
| HCV-J6 | Seq. ID 135 | -EKV--T-----IPVS-N--VQQPGALTQG--T---MV-M----- |
| HCV-J7 | Seq. ID 136 | -ENDNGTL---IQV--N--VKHRGALTHN--T-V-MI-MA--V- |

EXAMPLE 15

Comparison of Immunoreactivity for NS-5 Protein Derived Synthetic Peptides

Wells of 96-well plates were coated for 1 hour at 37° C. with each of the 23 peptides (designated as 259A–259E, culate the relative immunopotency for the other NS-5 peptides, the peptides in series 309–314 were seen to be equal to or more reactive than pep4 and pep5 from Example 4. The extension of pep5 to include an additional 10 residues (259E, i.e. pep12) increased the relative immunopotency from 47.6% to 70.1%.

TABLE 12

| | | Sequence | % IP |
|---|---|---|---|
| 314A(Pep16) | Seq. ID 16 | LRRLHQWISSECTTPCSGSWLRDIWDWICEVLSDFKTWLKAKLMPQLPGIPFVSCQRGYKGVWRVDGIMHTRCHCGAEITGHVKNGTMRI | 16.8 |
| 314B | Seq. ID 95 | GSWLRDIWDWICEVLSDFKTWLKAKLMPQL | 11.6 |
| 314C | Seq. ID 96 | SECTTPCSGSWLRDIWDWICEVLSDFKTWLKAKLMPQL | 14.2 |
| 312A | Seq. ID 97 | LRRLHQWISSECTTPCSGSWLRDIWDWICEVLSDFKTWLKAKLMPQL | 18.1 |
| 312B (Pep15) | Seq. ID 15 | LWRVSAEEYVEIRQVGDFHYTGMTTDNLKCPCQVPSPEFFTELDGVRLHRFAPPCKPLLREEVSFRVGLHEYPVGSQLPCEPEPD | 22.7 |
| 312C | Seq. ID 98 | DFHYTGMTTDNLKCPCQVPSP | 40.4 |
| 311A (Pep14) | Seq. ID 14 | LWRVSAEEYVEIRQVGDFHYTGMTTDNLKCPCQVPSP | 22.3 |
| 311B | Seq. ID 99 | EEYVEIRQVGDFHYTGMTTDNLKCPCQVPSP | 14.5 |
| 311C | Seq. ID 100 | LWRVSAEEYVEIRQVGDFHYVIGMTTDNLKCPCQVPSP | 16.8 |
| | | CKPLLREEVSFRVGLHEYPVGSQLPCEPEPD | |
| | | DGVRLHRFAPPCKPLLREEVSFRVGLHEYPVGSQLPCEPEPD | |
| | | CQVPSPEFFTELDGVRLHRFAPPCKPLLREEVSFRVGLHEYPVGSQLPCEPEPD | |
| 260A | Seq. ID 101 | DPSHTABAAGRRLARGSPPSVASSSASQLSAPSLKATCTANHDSPDAELIEANLLWRQEMGGNITRVESENKVVILDSFDPLVAEEDER | 18.9 |
| 260B | Seq. ID 102 | SSSASQLSAPSLKATCTANHDSP | 8.8 |
| 260C (Pep4) | Seq. ID 4 | DPSHTABAAGRRLARGSPPSVASSSASQLSAPSLKATCTANHDSP | 17.1 |
| 259B | Seq. ID 103 | RRLARGSPPSVASSSASQLSAPSLKATCTANHDSP | 45.4 |
| 259C (Pep5) | Seq. ID 5 | LWRQEMGGNITRVESENKVVILDSFDPLVAEEDER | 47.6 |
| 259D | Seq. ID 104 | DAELIEANLLWRQEMGGNITRVESENKVVILDSFDPLVAEEDER | 63.7 |
| 259E (Pep12) | Seq. ID 12 | ANHDSPDAELIEANLLWRQEMGGNITRVESENKVVILDSFDPLVAEEDER | 70.1 |
| | | KATCTANHDSPDAELIEANLLWRQEMGGNITRVESENKVVILDSFDPLVAEEDER | |
| 310A | Seq. ID 105 | RQEMGGNITRVESENKVVILDSFDPLVAEEDEREISVPAEILRKSRRFAQALPVWARPDYNPPLVETWKKPDYEPPVVHGCPLPPPKSPPVPPPRKKRTSTLST | 65.3 |
| 310B | Seq. ID 106 | SFDPLVAEEDEREISVPAEILRKSRR | 73.1 |
| 310C (Pep13) | Seq. ID 13 | RQEMGGNITRVESENKVVILDSFDPLVAEEDEREISVPAEILRKSRR | 63.7 |
| 309A | Seq. ID 107 | SENKVVILDSFDPLVAEEDEREISVPAEILRKSRR | 62.0 |
| 309B | Seq. ID 108 | YEPPVVHGCPLPPPKSPPVPPPRKKRT | 83.6 |
| 309C | Seq. ID 109 | VETWKKPDYEPPVVHGCPLPPPKSPPVPPPRKKRT | 93.9 |
| 309D (Pep11) | Seq. ID 11 | ARPDYNPPLVETWKKPDYEPPVVHGCPLPPPKSPPVPPPRKKRT | 100.0 |
| 309E | Seq. ID 110 | EILRKSRRFAQALPVWARPDYNPPLVETWKKPDYEPPVVHGCPLPPPKSPPVPPPRKKRT | 97.2 |
| | | AEEDEREISVPAEILRKSRRFAQALPVWARPDYNPPLVETWKKPDYEPPVVHGCPLPPPKSPPVPPPRKKRT | |

EXAMPLE 16

Immunoreactivity of a NS-2 Protein-derived Synthetic Peptide

Wells of 96-well plates were coated for 1 hour at 37° C. with 9 synthetic peptides derived from the NS-2 region of HCV. The results (Table 13) show that peptide 289B (i.e. pep17) was immunoreactive with selected anti-HCV positive samples with elevated ALT levels.

TABLE 13

Absorbance of NS-2 Peptides on Selected Anti-HCV Positive Samples with Elevated ALT Levels

| Sample | 289B |
|---|---|
| 1 | 0.263 |
| 4 | 0.311 |
| 7 | 0.266 |
| 18 | 0.751 |

EXAMPLE 17

Immunoreactivity of NS-3 Protein-derived Synthetic Peptide with Sera from Individuals with Early HCV Infection Wells of 96-well plates were coated for 1 hour at 37° C. with synthetic peptide 315D (i.e. pep18) derived from the NS-3 region of HCV. The results (Table 14) show that peptide 315D was strongly reactive with two serial samples from a plasmapheresis donor with elevated ALT levels.

TABLE 14

Absorbance of NS-3 Peptide on Serial Samples from Plasmapheresis Donor with Elevated ALT Levels

| Sample | 315D |
|---|---|
| A | 1.983 |
| B | 1.890 |

EXAMPLE 18

Detection of Antibodies to HCV NS-1 and ENV Regions by Peptide Based EIA Using Formats 7 and 8

Plasmapheresis samples with elevated ALT levels were analyzed on representative HCV peptide based EIAs according to the present invention with plates coated either with (i) pep1 and pep10C at 10 and 10 µg/mL each (Format 7, NS-1 kit) or (ii) pep7 and pep8 at 10 and 10 µg/mL each (Format 8, ENV kit). The results on HCV positive samples with elevated ALT levels are shown in Table 15, indicating a subpopulation of HCV infected individuals develop specific humoral immune responses directed at unique regions of the NS-1 and ENV proteins.

TABLE 16

Absorbance (492 nm) of Selected Samples with Elevated ALT Levels on Formats 7 and 8

| Sample | Format 7 NS-1 | Format 8 ENV |
|---|---|---|
| 1 | 0.804 | 1.499 |
| 2 | 0.707 | 2.487 |
| 3 | 0.441 | 1.649 |
| 4 | 2.651 | 2.868 |
| 5 | 0.064 | 1.569 |
| 6 | 0.244 | 0.790 |
| 7 | 0.382 | 0.692 |
| 8 | 1.438 | 1.226 |
| 9 | 0.304 | 0.411 |
| 10 | 0.160 | 0.282 |
| 11 | 0.079 | 0.599 |
| 12 | 0.286 | 0.302 |
| 13 | 0.045 | 0.610 |
| 14 | 3.058 | 2.862 |

Cutoff $OD_{492\,nm} = 0.200$

EXAMPLE 19

Synthesis of Substitution Analogues of Octameric HCV Envelope Peptide Antigen as Components of HCV Immunogens/Vaccines Substitution analogues of octameric HCV envelope pep7, pep8 and pep19 with a structure of:

(a) [Cys—Leu—Thr—Ile—Pro—Ala—Ser—Ala—Tyr—Glu—Val—Arg—Asn—Val—Ser—Gly—Ile—Tyr—His—Val—Thr—Asn—Asp—Cys—Ser—Asn—Ser—Ser—Ile—Val—Tyr—Glu—Ala—Ala—Asp—Val—Ile—Met—His—Ala—Pro—Gly—Cys—Val—Pro—Cys—Val—Arg—Glu—Asn—Asn—Ser—Ser—Arg—Cys—]$_8K_4K_2K$ (an analogue of octameric pep7 with sequence taken from HCV-JH);

(b) [Cys—Ile—Thr—Thr—Pro—Val—Ser—Ala—Ala—Glu—Val—Lys—Asn—Ile—Ser—Thr—Gly—Tyr—Met—Val—Thr—Asn—Asp—Cys—Thr—Asn—Asp—Ser—Ile—Thr—Trp—Gln—Leu—Gln—Ala—Ala—Val—Leu—His—Val—Pro—Gly—Cys—Val—Pro—Cys—Glu—Lys—Val—Gly—Asn—Thr—Ser—Arg—Cys—]$_8K_4K_2K$ (an analogue of octameric pep7 with sequence taken from HCV-J6);

(c) [Cys—Val—Thr—Val—Pro—Val—Ser—Ala—Val—Glu—Val—Arg—Asn—Ile—Ser—Ser—Ser—Tyr—Tyr—Ala—Thr—Asn—Asp—Cys—Ser—Asn—Asn—Ser—Ile—Thr—Trp—Gln—Leu—Thr—Asn—Ala—Val—Leu—His—Leu—Pro—Gly—Cys—Val—Pro—Cys—Glu—Asn—Asp—Asn—Gly—Thr—Leu—Arg—Cys—]$_8K_4K_2K$ (an analogue of octameric pep7 with sequence taken from HCV-J6);

(d) [Phe—Thr—Phe—Ser—Pro—Arg—Arg—His—Glu—Thr—Val—Gln—Asp—Cys—Asn—Cys—Ser—Ile—Tyr—Pro—Gly—His—Val—Ser—Gly—His—Arg—Met—Ala—Trp—Asp—Met—Met—Met—Asn—Trp—Ser—Pro—Thr—Ala—]$_8K_4K_2K$ (an analogue of octameric pep8 with sequence taken from HCV-JH);

-continued (e) [Phe—Ile—Val—Ser—Pro—Gln—His—His—His—Phe—Val—Gln—Asp—
Cys—Asn—Cys—Ser—Ile—Tyr—Pro—Gly—Thr—Ile—Thr—Gly—His—
Arg—Met—Ala—Trp—Asp—Met—Met—Met—Asn—Trp—Ser—Pro—Thr—
Ala—]₈K₄K₂K (an analogue of octameric pep8 with sequence taken from HCV-J6);

(f) [Phe—Ile—Ile—Ser—Pro—Glu—Arg—Asn—Phe—Thr—Gln—Glu—Cys—
Asn—Cys—Ser—Ile—Tyr—Gln—Gly—His—Ile—Thr—Gly—His—Arg—
Met—Ala—Trp—Asp—Met—Met—Leu—Asn—Trp—Ser—Pro—Thr—Leu—
]₈K₄K₂K (an analogue of octameric pep8 with sequence taken from HCV-J7);

(g) [Cys—Val—Arg—Glu—Gly—Asn—Val—Ser—Arg—Cys—Trp—Val—Ala—
Met—Thr—Pro—Thr—Val—Ala—Thr—Arg—Asp—Gly—Lys—Leu—Pro—
Ala—Thr—Gln—Leu—Arg—Arg—His—Ile—Asp—Leu—Leu—Val—Gly—
Ser—Ala—Thr—Leu—Cys—]₈K₄K₂K (Octameric pep19)

(h) [Cys—Val—Arg—Glu—Asn—Asn—Ser—Ser—Arg—Cys—Trp—Val—Ala—
Leu—Thr—Pro—Thr—Leu—Ala—Ala—Arg—Asn—Ala—Ser—Val—Pro—
Thr—Thr—Thr—Leu—Arg—Arg—His—Val—Asp—Leu—Leu—Val—Gly—
Thr—Ala—Ala—Phe—Cys—]₈K₄K₂K (an analogue of octameric pep19 with
sequence taken from HCV-JH);

(i) [Cys—Glu—Lys—Val—Gly—Asn—Thr—Ser—Arg—Cys—Trp—Ile—Pro—
Val—Ser—Pro—Asn—Val—Ala—Val—Gln—Gln—Pro—Gly—Ala—Leu—
Thr—Gln—Gly—Leu—Arg—Thr—His—Ile—Asp—Met—Val—Val—Met—
Ser—Ala—Thr—Leu—Cys—]₈K₄K₂K (an analogue of octameric pep19 with
sequence taken from HCV-J6);

(j) [Cys—Glu—Asn—Asp—Asn—Gly—Thr—Leu—Arg—Cys—Trp—Ile—Gln—
Val—Thr—Pro—Asn—Val—Ala—Val—Lys—His—Arg—Gly—Ala—Leu—
Thr—His—Asn—Leu—Arg—Thr—His—Val—Asp—Met—Ile—Val—Met—
Ala—Ala—Thr—Val—Cys—]₈K₄K₂K (an analogue of octameric pep19 with
sequence taken from HCV-J7);

respectively according to a general chemical synthesis procedure described in Example 7 and used as immunogens in our immunization of guinea pigs and chimpanzees.

These octameric peptides are injected as a mixture into healthy, naive animals both intradermally and subcutaneously at a dosage of 25 ug per mixture per kg body weight using 2% alum as an adjuvant. After the initial immunization, these animals are boosted at the same dose once per month for a period of four months. The animals are bled monthly and the collected immune sera are monitored for their anti-HCV envelope/NS-1 immunoreactivity. Six months after the last boost, the immunized chimpanzees are subsequently challenged by experimental inoculation with various dosages (e.g. 50 mL) of a proven infectious Factor VIII concentrate known to contain HCV so as to evaluate the efficacy in using a mixture of these octameric envelope peptides as a vaccine for the prevention of HCV infection, initially by the evaluation of several serological/clinical markers, and subsequently, the observation of the appearance of clinical symptoms of NANBH in these animals.

The present invention has been illustrated in the above examples, which are not to be used to limit the scope of the invention.

We claim:

1. A peptide composition for detecting the presence of antibodies to hepatitis C virus (HCV) in body fluids comprising a peptide having an amino acid sequence $AA_{2273}$-$AA_{2332}$ from HCV Pep11 (SEQ ID NO:11).

1. a segment of the peptide having specific immunoreactivity to antibodies to HCV and containing at least 27 amino acids from the N-terminus at $AA_{2273}$ to the C-terminus;
 2. a conjugate of the peptide; and
 3. a polymer of the above peptide.

2. A peptide composition according to claim 1 wherein the peptide has an amino acid sequence $AA_{2273}$-$AA_{2332}$ of HCV Pep11 (SEQ ID NO:11).

3. A peptide composition comprising a mixture of Peptides VIIIE and pep11 wherein VIIIE is:

Ser—Thr—Ile—Pro—Lys—Pro—Gln—Arg—Lys—Thr—Lys—Arg—Asn—
Thr—Asn—Arg—Arg—Pro—Gln—Asp—Val—Lys—Phe—Pro—Gly—Gly—
Gly—Gln—Ile—Val—Gly—Gly—Val—Tyr—Leu—Leu—Pro—Arg—Arg—
Gly—Pro—Arg—Leu—Gly—Val—Arg—Ala—Thr—Arg—Lys—Thr—Ser—
Glu—Arg—Ser—Gln—Pro—Arg—Gly—Arg—Arg—X  (SEQ ID NO: 20);

and pep11 is $AA_{2273}$-$AA_{2332}$ of HCV Pep11 (SEQ ID NO:11);
wherein X is —OH or NH$_2$, and an analogue of anyone of the above peptides having an amino acid sequence derived from a strain/isolate of HCV in a region corresponding to the peptide and having specific immunoreactivity to antibodies to HCV.

* * * * *